(12) United States Patent
Rodriguez-Boulan et al.

(10) Patent No.: US 10,849,922 B2
(45) Date of Patent: *Dec. 1, 2020

(54) TREATMENTS FOR RETINAL DISORDERS

(71) Applicant: Cornell University, Ithaca, NY (US)

(72) Inventors: Enrique Rodriguez-Boulan, New York, NY (US); Marcelo Nociari, Summit, NJ (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,740

(22) Filed: Oct. 7, 2019

(65) Prior Publication Data
US 2020/0121711 A1 Apr. 23, 2020

Related U.S. Application Data

(63) Continuation of application No. 13/980,687, filed as application No. PCT/US2012/021997 on Jan. 20, 2012, now Pat. No. 10,463,687.

(60) Provisional application No. 61/434,585, filed on Jan. 20, 2011.

(51) Int. Cl.
*A61K 31/724* (2006.01)
*A61K 47/69* (2017.01)
*G01N 33/92* (2006.01)
*B82Y 5/00* (2011.01)

(52) U.S. Cl.
CPC ........ *A61K 31/724* (2013.01); *A61K 47/6951* (2017.08); *B82Y 5/00* (2013.01); *G01N 33/92* (2013.01); *Y10T 436/143333* (2015.01)

(58) Field of Classification Search
CPC .... A61K 31/724; A61K 47/6851; B82Y 5/00; G01N 33/92; Y10T 436/43333
USPC .......................................................... 514/58
See application file for complete search history.

(56) References Cited

U.S. PATENT DOCUMENTS

| | | | |
|---|---|---|---|
| 3,420,788 A | 1/1969 | Solms | |
| 3,426,011 A | 2/1969 | Parmerter | |
| 3,453,257 A | 7/1969 | Parmerter | |
| 3,453,259 A | 7/1969 | Parmerter | |
| 3,459,731 A | 8/1969 | Gramera | |
| 4,737,323 A | 4/1988 | Martin et al. | |
| 5,134,127 A | 7/1992 | Stella et al. | |
| 8,158,609 B1 * | 4/2012 | Marsh | A61K 47/40 514/58 |
| 10,463,687 B2 * | 11/2019 | Rodriguez-Boulan | A61K 47/6951 |
| 2001/0021703 A1 | 9/2001 | Kosak | |
| 2007/0275048 A1 | 11/2007 | Liu et al. | |
| 2010/0069471 A1 | 3/2010 | Manoharan et al. | |
| 2010/0113539 A1 | 5/2010 | Scott et al. | |
| 2014/0038918 A1 | 2/2014 | Rodriguez-Boulan et al. | |

OTHER PUBLICATIONS

Adair-Kirk T.L. et al., "Smoke Particulates Stress Lung Cells", Nature Medicine 14(10):1024-1025 (Oct. 2008).
Armenti S.T. et al., "Quantitative Fundus Autofluorescence for the Evaluation of Retinal Diseases", Journal of Visualized Experiments 109:1-5 (2016).
Audo I. et al., "FAF Imaging for Retinal Diseases", Review of Opthalmology, pp. 1-8 (Aug. 12, 2005).
Berge S.M. et al., "Pharmaceutical Salts", Journal of Pharmaceutical Sciences 66(1):1-19 (Jan. 1977).
Bindewald-Wittich A. et al., "Two-Photon-Excited Fluorescence Imaging of Human RPE Cells With a Femtosecond Ti:Sapphire Laser", Investigative Ophthalmology & Visual Science 47(10):4553-4557 (Oct. 2006).
Bodine K.D. et al., "Synthesis of Readily Modifiable Cyclodextrin Analogues via Cyclodimerization of an Alkynyl-Azido Trisaccharide", J. Am. Chem. Soc. 126(6):1638-1639 (2004).
Burke T.R. et al., "Quantitative Fundus Autofluorescence in Recessive Stargardt Disease", Invest Ophthalmol Vis Sci. 55(5):2841-2852 (May 2014).
Crouch R.K. et al., "A2E and Lipofuscin", Progress in Molecular Biology and Translational Science 134:449-463 (2015).
De S. et al., "Interaction of A2E With Model Membranes. Implications to the Pathogenesis of Age-Related Macular Degeneration", J. Gen. Physiol. 120:147-157 (Aug. 2002).
Delori F.C. et al., "In Vivo Fluorescence of the Ocular Fundus Exhibits Retinal Pigment Epithelium Lipofuscin Characteristics", Investigative Ophthalmology & Visual Science 36(3):718-729 (Mar. 1995).
Delori F.C. et al., "In Vivo Measurement of Lipofuscin in Stargardt's Disease—Fundus flavimaculatus", Investigative Opthalmology and Visual Science 36:2327-2331, Abstract (Oct. 1995).
Di Cagno M.P., "The Potential of Cyclodextrins as Novel Active Pharmaceutical Ingredients: A Short Overview", Molecules 22(1), 14 pages (2016).
Dordunoo S. K., et al., "Preformulation Studies on Solid Dispersions Containing Triamterene or Temezepam in Polyethylene Glycols or Gelucire 44/14 for Liquid Filling of Hard Gelatin Capsules", Drug Development and Industrial Pharmacy 17(12):1685-1713 (1991).
Dostert C. et al., "Innate Immune Activation Through Nalp3 Inflammasome Sensing of Asbestos and Silica" Science 320(5876):674-677 (May 2, 2008).

(Continued)

*Primary Examiner* — Ganapathy Krishnan
(74) *Attorney, Agent, or Firm* — Scully, Scott, Murphy & Presser, P.C.

(57) ABSTRACT

The present invention relates to the use of cyclic oligosaccharides as chemical complexants of lipofuscin bisretinoids (A2E) to prevent and treat eye (i.e., retinal or macular) disease. Monomeric, dimeric, multimeric, or polymeric oligosaccharide rings act as pharmacologic agents to prevent and treat ophthalmologic disorders triggered by the accumulation of lipofuscin in the retinal pigment epithelium (RPE), which occurs as a consequence of either genetic disorders, such as Stargardt Disease (SD) and Best Disease (BD), or aging, such as Age-Related Macular Degeneration (AMD), or other diseases, such as retinitis pigmentosa, and cone-rod dystrophy.

11 Claims, 34 Drawing Sheets

(56) References Cited

OTHER PUBLICATIONS

Eandi C.M. et al., "Acute Central Serous Chorioretinopathy and Fundus Autofluorescence", Retina 25:989-993 (2005).
Fernandes A.F. et al., "Oxidative Inactivation of the Proteasome in Retinal Pigment Epithelial Cells", The Journal of Biological Chemistry 283(30)20745-20753 (Jul. 25, 2008).
Gliem M. et al. "Quantitative Fundus Autofluorescence in Early and Intermediate Age-Related Macular Degeneration", JAMA Ophthalmology 134(7):817-824 (Jul. 2016).
Haralampus-Grynaviski N.M. et al., "Spectroscopic and Morphological Studies of Human Retinal Lipofuscin Granules", PNAS 100(6):3179-3184 (Mar. 18, 2003).
Holz F.G. et al., "Fundus Autofluorescence and Development of Geographic Atrophy in Age-Related Macular Degeneration", Invest Ophthalmol Vis Sci. 42(5):1051-1056 (Apr. 2001).
Irie T. et al., "Hydroxypropylcyclodextrins in Parenteral Use. I: Lipid Dissolution and Effects on Lipid Transfers In Vitro", Journal of Pharmaceutical Sciences 81(6):521-523 (Jun. 1992).
Issa P.C. et al., "Fundus Autofluorescence in the Abca4−/− Mouse Model of Stargardt Disease-Correlation With Accumulation of A2E, Retinal Function, and Histology", Invest Ophthalmol Vis Sci. 54(8):5602-5612 (2013).
Jang Y.P. et al., "Characterization of Peroxy-A2E and Furan-A2E Photooxidation Products and Detection in Human and Mouse Retinal Pigment Epithelial Cell Lipofuscin", Journal of Biological Chemistry 280(48):39732-39739 (Dec. 2, 2005).
Khan K.N. et al., "Differentiating Drusen: Drusen and Drusen-Like Appearances Associated With Ageing, Age-Related Macular Degeneration, Inherited Eye Disease and Other Pathological Processes", Progress in Retinal and Eye Research 53:70-106 (2016).
Khan A.R. et al., "Methods for Selective Modifications of Cyclodextrins", Chemical Reviews 98(5):1977-1996 (1998).
Klymchenko A.S. et al., "2D Analogues of the Inverted Hexagonal Phase Self-Assembled from 4,6-Dialkoxylated Isophthalic Acids at Solid-Liquid Interfaces", Nanoscale 2(9):1773-1780 (2010).
Lakkaraju A. et al., "The Lipofuscin Fluorophore A2E Perturbs Cholesterol Metabolism in Retinal Pigment Epithelial Cells", PNAS 104(26):11026-11031 (Jun. 26, 2007).
Leclercq L., "Interactions Between Cyclodextrins and Cellular Components: Towards Greener Medical Applications?", Journal of Organic Chemistry 12:2644-2662 (2016).
Liu Y. et al., "Cooperative Binding and Multiple Recognition by Bridged Bis(B-Cyclodextrin)s With Functional Linkers", Accounts of Chemical Research 39(10):681-691 (Oct. 2006).
Maeda A. et al., "Retinopathy in Mice Induced by Disrupted All-Trans-Retinal Clearance", The Journal of Biological Chemistry 283(39):26684-26693 (Sep. 26, 2008).
Maggon R. et al., "Best's Vitelliform Macular Dystrophy", Medical Journal Armed Forces India 64(4):379-381 (2008).
Martinon F., "Mechanisms of Uric Acid Crystal-Mediated Autoinflammation", Immunological Reviews 233(1):218-232 (2010).
Martinon F., "Update on Biology: Uric Acid and the Activation of Immune and Inflammatory Cells", Curr Rheumatol Rep 12(2):135-141 (2010).
Martinon F. et al., "The Inflammasomes: Guardians of the Body", Annual Reviews Immunol. 27:229-265 (2009).
Mocanu G. et al., "Cyclodextrin Polymers", Journal of Bioactive and Compatible Polymers 16:315-342 (Jul. 2001).
Ng K-P et al., "Retinal Pigment Epithelium Lipofuscin Proteomics", Molecular & Cellular Proteomics 7(7):1397-1405 (2008).

Nociari M.M. et al., "Lipofuscin Accumulation into and Clearance from Retinal Pigment Epithelium Lysosome: Physiopathology and Emering Therapeutics", Lysosomes-Associated Diseases and Methods to Study Their Function, 28 pages (2017).
Nociari M.M. et al., "Beta Cyclodextrins Bind, Stabilize, and Remove Lipofuscin Bisretinoids from Retinal Pigment Epithelium", PNAS 111(14):E1402-E1408 (Mar. 2014).
Ozmen E.Y. et al., "Synthesis and Characterization of Cyclodextrin-Based Polymers as a Support for Immobilization of Candida Rugosa Lipase", Journal of Molecular Catalysis B: Enzymatic 57:109-114 (2009).
Rabb M.F. et al., "Cone-Rod Dystrophy: A Clinical and Histopathologic Report", Ophthalmology 93(11):1443-1451, Abstract (Nov. 1986).
Ragauskaite L. et al., "Environmental Effects on the Photochemistry of A2-E, a Component of Human Retinal Lipofuscin", Photochemistry and Photobiology 74(3):483-488 (2001).
Rudolf M. et al., "Histologic Basis of Variations in Retinal Pigment Epithelium Autofluorescence in Eyes With Geographic Atrophy", Ophthalmology 120(4):821-828 (Apr. 2013).
Santos-Lozano A. et al., "Niemann-Pick Disease Treatment: a Systematic Review of Clinical Trials", Annals of Translational Medicine 3:22):1-9 (2015).
Schuchman E.H. et al., "Types A and B Niemann-Pick Disease", Mol Genet Metab. 120(1-2):27-33 (2017).
Seong S.Y. et at., "Hydrophobicity: an Ancient Damage-Associated Molecular Pattern that Initiates Innate Immune Responses", Nature Reviews-Immunology 4(6):469-478 (Jun. 2004).
Sheen P-C et al., "Bioavailability of a Poorly Water-Soluble Drug from Tablet and Solid Dispersion in Humans", Journal of Pharmaceutical Sciences 80(7):712-714 (Jul. 1991).
Sohal R.S., "Metabolic Rate, Aging, and Lipofuscin Accumulation", Age Pigments, Chapter 11, Elsevier/North-Holland Biomedical Press, pp. 303-316 (1981).
Sparrow J.R. et al. "Flecks in Recessive Stargardt Disease: Short-Wavelength Autofluorescence, Near-Infrared Autofluorescence, and Optical Coherence Tomography", Invest Ophthalmol Vis Sci. 56(8):5029-5039 (Jul. 2015).
Sparrow J.R., "Bisretinoids of RPE Lipofuscin: Trigger for Complement Activation in Age-Related Macular Degeneration", Inflammation and Retinal Disease: Complement Biology and Pathology, Advances in Experimental Medicine and Biology 703:63-74 (2010).
Sparrow J.R. et al., "RPE Lipofuscin and its Role in Retinal Pathobiology", Experimental Eye Research 80(5):595-606 (2005).
Sparrow J.R. et al., "A2E, a Lipofuscin Fluorophore, in Human Retinal Pigmented Epithelial Cells in Culture", Invet Ophthalmol Vis Sci. 40(12):2988-2995 (1999).
Stella V.J. et al., "Cyclodextrins", Toxicologic Pathology 36(1):30-42 (2008).
Szente L. et al., "Cyclodextrin-Lipid Complexes: Cavity Size Matters", Struct Chem. 28:479-492 (2017).
Szejtli J., "Introduction and General Overview of Cyclodextrin Chemistry", Chem Rev 98(5):1743-1754 (1998).
Trotta F. et al., "Characterization and Applications of New Hyper-Cross-Linked Cyclodextrins", Composite Interfaces 16:39-48 (2009).
Vecsernyés M. et al., "Cyclodextrins, Blood-Brain Barrier, and Treatment of Neurological Diseases", Archives of Medical Research 45:711-729 (2014).
Zarbin M.A. et al., "Pathway-Based Therapies for Age-Related Macular Degeneration: an Integrated Survey of Emerging Treatment Alternatives", Retina 30(9):1350-1367 (2010).
The Merck Manual, 1992, 16th Ed., pp. 2385-2386.

\* cited by examiner

Poly B: soluble polymeric Beta CD

SB276dim

TREATMENTS FOR RETINAL DISORDERS

CROSS REFERENCE TO RELATED APPLICATIONS

This application is a continuation application of U.S. application Ser. No. 13/980,687 filed on Oct. 8, 2013, which is a National Stage Entry of Application No. of PCT/US2012/021997 filed on Jan. 20, 2012, which claims the benefit of priority from U.S. Provisional Application No. 61/434,585, filed on Jan. 20, 2011.

GOVERNMENT SUPPORT

This invention was made with government support under GM079238 awarded by the National Institutes of Health. The government has certain rights in the invention.

FIELD OF THE INVENTION

The present invention relates, generally, to methods for treating retinal diseases and conditions, and more particularly, to the treatment of retinal diseases and conditions caused by accumulation of bisretinoids, such as age-related macular degeneration and related disorders.

BACKGROUND OF THE INVENTION

The human eye is designed so that light traverses the anterior portions (cornea, aqueous humor and lens), the vitreous and the anterior layers of the retina before reaching the outer segments of light-sensitive cells or photoreceptors (PROS), i.e., the rods and cones. FIG. 1A provides a general schematic of the retinal components.

Light not absorbed by the visual pigments in PROS (e.g., rhodopsin in rods, various opsins in cones) is absorbed by the adjacent retinal pigment epithelial cells (RPE), which is highly pigmented, and therefore, functions as a dark chamber. Located at the interphase between photoreceptor (PR) and the choroidal blood vessels, the RPE performs key support functions for PR. These include: (i) providing key blood nutrients through various RPE transporters (e.g., glucose, aminoacids); (ii) maintaining the ionic composition of the subretinal space (space between RPE and PR) through sophisticated transport mechanisms; (iii) participating in the "visual cycle" (FIG. 1B), by re-isomerizing a key lipid, cis-retinal, which intimately associates with rhodopsin and is the acceptor for photons; and (iv) phagocytosis (i.e., "eating up and digestion of") PR outer segments, a key aspect of the renewal of the retina. In the visual cycle, light impinges on cis-retinal and converts it into trans-retinal, which is quickly converted into an alcohol derivative (cis-retinol), which is transported to the RPE for regeneration of cis-retinal. All of these RPE functions are essential for normal vision.

Unlike other epithelial cells, which regenerate themselves continuously through cell division, RPE cells do not divide, and therefore, are more susceptible to accumulation of materials as they age. One RPE cell disposes the debris generated by 30-50 adjacent PR cells. This debris is produced by circadian shedding of PR tips, the oldest part of PROS.

The daily and heavy phagocytic activity of RPE cells results in the accumulation of lipofuscin in their digestive system, i.e., the endo-lysosomal apparatus. Lipofuscin accumulation is a universal and phylogenically conserved marker of aging (Sohal, R. S., Age Pigments, Elsevier Science Ltd., © 1981). All metabolically active post-mitotic cells, including cardiac myocytes, neurons, and RPE cells, show age-related accumulation of lipofuscin within their lysosomal system. For most of these cells, the lipofuscin originates primarily from the incomplete degradation of exhausted organelles (autophagy). Depending upon the tissue analyzed, lipofuscin granules normally have 30-70% of protein content (Sohal, Ibid.). In striking contrast, the lipofuscin deposits of aged RPE cells contain almost no protein (<2%); rather, they are constituted of lipidic pigment derivatives of trans-retinal, generated by the visual cycle (Ng, K. P., et al., *Mol. Cell Proteomics*, 7(7), pp. 1397-405, 2008). The most abundant and toxic lipidic pigments found are the bis-retinoids, primarily A2E, followed by A2E isomers, oxidized derivatives of A2E, A2-dihydropyridine-phosphatidylethanolamine (A2-DHP-PE), and smaller quantities of other Vitamin A conjugates belonging to the all-trans-retinal dimer series (Sparrow, J. R., et al., *Exp. Eye Res.*, 80(5), pp. 595-606, 2005). The non-enzymatic pathway leading to the formation of these bisretinoids has been elucidated. FIG. 1C provides a general overview of the bisretinoid pathways.

A2E-lipofuscin accumulates linearly with age because this material is refractory to lysosomal enzyme degradation. Beyond a certain threshold, A2E-lipofuscin becomes toxic to RPE cells, which eventually results in their malfunction and death. This deterioration process results in the decrease or loss of the ability of RPE cells to support adjacent PR cells. Loss of PR cells resulting from the toxic effects of lipofuscin on RPE cells is considered a central pathogenetic mechanism in genetic and age-related retinal degenerations.

Age-related macular degeneration (AMD) is the most common cause of blindness, affecting 36% of Americans in their eighth decade of life, with a devastating decrease in their quality of life (De, S., et al., *J. Gen. Physiol.*, 120(2): pp. 147-57, 2002). Moreover, clinical evidence shows that photoreceptors overlying bisretinoid-loaded RPE areas (containing mostly A2E) are the most prone to degeneration (Holz, F. G., et al., *Invest. Ophthalmol. Vis. Sci.*, 42(5): p. 1051-6, 2001). Although decades are generally required for the natural accumulation of A2E in RPE, in some human genetic afflictions, like Stargardt Disease (SD) and Best Disease (BD), A2E reaches pathogenic levels typically by about 30 years of age, typically resulting in blindness in the fourth decade of life.

Lipofuscin-containing A2E has been shown harmful to RPE cells (Sparrow, J. R., et al., *Adv. Exp. Med. Biol.*, 703: p. 63-74, 2010; Fernandes, A. F., et al., *J. Biol. Chem.*, 283(30): pp. 20745-53, 2008; Lakkaraju, A., et al., *Proc. Natl. Acad. Sci. U.S.A.*, 104(26): pp. 11026-31, 2007). Three mechanisms have been postulated as contributing to A2E-mediated RPE-toxicity: (1) the A2E's predisposition to oxidation, which can be spontaneous or light-induced and leads to the formation of reactive oxygen species (ROI); (2) A2E's detergent properties, i.e., intercalation of A2E into lysosomal membranes leads to interference of cholesterol extrusion and accumulation of cholesterol, as observed in cholesterol storage diseases such as Niemann Pick; and (3) A2E's tendency to form hydrophobic crystals, which are most likely detected by innate immune receptors and trigger inflammation.

A2E and its derivatives have intrinsic fluorescence and account for most of RPE-lipofuscin (RPE-LF) autofluorescence (Sparrow, J. R., et al., *Invest. Ophthalmol. Vis. Sci.*, 40(12): pp. 2988-95, 1999). The fluorescence emission of A2E is influenced by the polarity of the environment in which the molecule is immersed (Sparrow, et al., 1999, Ibid.; Ragauskaite, L., et al., *Photochem. Photobiol.*, 74(3): p.

483-8, 2001; De, et al., 2002, Ibid.). Thus, in water, A2E maximally emits at 610 nm, but in non-polar solvents, such as n-butyl chloride, A2E typically exhibits a blue-shifted maximum of 585 nm (Sparrow et al., 1999, Ibid.). The emission maxima of A2E inside RPE cells is generally between 565 and 570 nm (Sparrow, et al., 1999, Ibid.; Haralampus-Grynaviski, N. M., et al., *Proc. Natl. Acad. Sci. U.S.A.*, 100(6): p. 3179-84, 2003). This fluorescence spectrum suggests that, when inside a cell, A2E is tightly protected against the solvatochromic shift caused by water molecules (Sparrow, et al., 1999, Ibid.). Moroever, it is known that, with aging, the RPE-LF fluorescence shifts even more toward blue, suggesting that with time A2E deposits may adopt stiffer organization inside these granules (Delori, F. C., et al., *Invest. Ophthalmol. Vis. Sci.*, 36(3): pp. 718-29, 1995).

High-magnification transmission electron-microscopy (TEM) has revealed that A2E deposits are housed within the interior of discrete membrane-bound organelles that are uniformly dense, roughly spherical, and approximately 1 micrometer in diameter (Haralampus-Grynaviski, et al., 2003, Ibid.; Bindewald-Wittich, A., et al., *Invest. Ophthalmol. Vis. Sci.*, 47(10): pp. 4553-7, 2006). Data obtained using atomic force microscopy and purified granules has revealed that the bulk of A2E deposits in RPE cells reside in the lumen of these post-lysosomal bodies, forming an orderly aggregated structure (Ng, et al., 2008, Ibid.; Sparrow, et al., 1999, Ibid.). Because of their ultrastructural appearance, A2E-containing formations are sometimes also referred to as "lipofuscin granules".

Some studies have predicted that positively-charged amphipathic lipids with cone-shaped molecular geometry, like A2E, can self-assemble in water as an inverted hexagonal phase creating large hydrophobic semi-crystaline constructions (Seong, S. Y., et al., *Nat. Rev. Immunol.*, 4(6): pp. 469-78, 2004; Klymchenko, A. S., et al., *Nanoscale*, 2(9): pp. 1773-80, 2010). Significantly, highly repetitive hydrophobic structures are known to be among the strongest inducers of chronic inflammation (Seong, et al., 2004, Ibid.). For example, monosodium urate, silica crystals, and asbestos are known to form hydrophobic crystals that are highly pro-inflammatory (Martinon, F., et al., *Annu. Rev. Immunol.*, 27: pp. 229-65 (2009); Martinon, F., et al., *Immunol. Rev.*, 233(1): pp. 218-32, 2010; *Martinon, F., Curr. Rheumatol. Rep.*, 12(2): pp. 135-41 (2010); Dostert, C., et al., 320 (5876): pp. 674-7, 2008).

Current therapeutic approaches aimed at alleviating vision loss and retinal (for example, macular) diseases associated with A2E accumulation generally rely on retarding A2E formation by drugs or viral-based gene delivery methods. Current drug therapy generally involves decreasing all-trans-retinal formation, which generally causes sight loss, including night blindness, as a side effect (Zarbin, M. A., et al., *Retina*, 30(9): pp. 1350-67, 2010). Current gene therapy approaches generally involve delivering the WT gene to individuals with genetic mutations, but this approach is not applicable to AMD. Significantly, neither of these methodologies has been shown to effectively retard or reverse the accumulation of A2E once such accumulation has occurred.

SUMMARY OF THE INVENTION

The instant application is foremost directed to a method for the treatment or prevention of lipofuscin-associated macular damage that does not rely on decreasing trans-retinal formation or gene therapy approaches of the art. Accordingly, the instant invention provides an alternative and effective method for the treatment of AMD and related diseases and conditions without the known significant drawbacks of the methodologies of the art.

The methodology described herein achieves this improvement by employing cyclic oligosaccharide complexants (i.e., hosts, encapsulants, sequestrants, or binders) of lipofuscin bisretinoid lipids that stabilize and reduce lipofuscin bisretinoid lipid levels in RPE cells with minimal or no disruption in cell vitality. Moreover, the cyclic oligosaccharides described herein advantageously possess little or no toxicity associated with their use.

In the method, a cyclic oligosaccharide, which may be a monomer, dimer, multimer (e.g., trimer, tetramer, pentamer, hexamer, heptamer, octamer), or polymer thereof, is directed to (i.e., targets) RPE cells, where they function as chemical complexants of the main constituents of RPE-lipofuscin, i.e., A2E and iso-A2E and derivatives and modified forms thereof, for the treatment or prevention of lipofuscin-mediated retinal deterioration. Specifically, the cyclic oligosaccharides form guest-host complexes with A2E or a modified form thereof by incorporating A2E or a modified form thereof in the less hydrophilic (i.e., hydrophobic) binding pocket (i.e., cavity) of the cyclic oligosaccharide. As A2E or its modified form is substantially shielded and protected when complexed in the relatively hydrophobic cavity of the cyclic oligosaccharide, the cyclic oligosaccharide substantially diminishes or even completely prevents A2E oxidation. As further discussed below, the use of cyclic oligosaccharides, even at high doses, has herein been found to not compromise the well-being of RPE cells while dissolving A2E crystals and reducing overall A2E levels in RPE cells.

The instant application is also directed to an assay method for identifying a compound that binds to a lipofuscin bisretinoid lipid. Thus, the method can be particularly instrumental in identifying a compound that can treat or prevent lipofuscin-associated macular damage, or a disease or condition associated therewith.

The assay method generally includes the following steps: (i) providing at least two solutions containing a lipofuscin bisretinoid lipid, wherein the at least two solutions are substantially the same in all respects; (ii) adding a candidate compound to one of the solutions; (iii) measuring fluorescence spectra of the two solutions within a wavelength range of 530 nm to 700 nm at an excitation wavelength that causes fluorescence of the lipofuscin bisretinoid lipid within said wavelength range; (iv) determining an area under corresponding spectral curves for each of the two solutions in said wavelength range; and (v) determining the ratio of the area under the spectral curve for the solution holding the candidate compound relative to the area under the spectral curve for the solution not holding the candidate compound. In the assay method, a ratio greater than 1 indicates that the candidate compound has bound with the lipofuscin bisretinoid lipid. Thus, a ratio greater than 1 indicates that the candidate compound has potential as an effective medicinal agent for treating or preventing lipofuscin-associated macular damage or a disease or condition associated therewith.

BRIEF DESCRIPTION OF THE FIGURES

FIG. 3A: Drawing of an exemplary multimeric or polymeric structure of linked cyclic oligosaccharides, wherein C represents one or more type of the cyclic oligosaccharides, L represents a linker, and each X represents a cell-targeting agent, such as M6P or one or more protonable nitrogenated groups similar to, but not limited to those found in lysosomotropic agents (chloroquine, lysotrackers, lysosensors, etc.). The dashed line to X indicates that these groups may or may not be present, and, if present, may be attached to any portion of the group to which they are bound. FIG. 3B: Generalized depictions of a composition having an active portion therein that includes two or more dimers of cyclic oligosaccharide rings (multimer). Dimers can be identical or, alternatively, may be composed of more than one type of cyclic oligosaccharide. R may represent streptavidin, polymers, or multimerizing agents that facilitate the organization of dimers in tandem.

FIG. 7A (top): Fluorescence spectra of these compounds. FIG. 7A (bottom): structure of the soluble polymeric beta-cyclodextrin (Poly B) used. FIG. 7B (top): Chart showing the relative AUC of these CD compounds. FIG. 7B (bottom): Structures of the two dimeric beta-cyclodextrins.

As shown in FIG. 12B, after 48 hours in aqueous phase, A2E is oxidized, whereas when incubated in the presence of increasing levels of beta-cyclodextrin (10-100 mM) oxidation of A2E was not observed.

FIG. 13A: Predicted size (<0.005 um) of A2E molecule based on its molecular weight of 596 (top), and Differential Interference Contrast (DIC) microscopy (bottom), combined with fluorescence microscopy, which shows that A2E aggregates that form in aqueous phase (left panel) and within cells (right panel) are in the micron range size. FIG. 13B: General schematic of experiment demonstrating that A2E aggregates cannot diffuse through transwell chambers with 0.4 μm pores but diffuse through transwell chambers with 3 μm pores. FIG. 13C: Results showing that addition of beta-cyclodextrin to the aqueous phase dissolved the A2E aggregates, thus showing that A2E can diffuse through 0.2 μm pores.

FIG. 15A outlines the experimental conditions. FIG. 15B shows images of the treated and untreated confluent cells under fluorescent and white light conditions. Panel A shows control epithelial cells loaded with A2E (bright fluorescence). Panel C shows polarized epithelium treated with CDs after 24 h. The loss of fluorescent pigments is notable. Panels B and D are images of the same epithelia illuminated with white light to demonstrate that their integrity is not compromised by treatment with CDs.

FIG. 16A depicts the experimental conditions for administering CDs and obtaining fundus images. FIG. 16B shows fundus images obtained from eight month old WT control (A), DKO (B) and CD-treated DKO (C) mice. Note clear dots (drusen) in color fundus of DKO that are reduced by CD treatment (compare A, B and C). Autofluorescence fundus images from WT control (D), DKO (E) and CD-treated DKO (F). The numbers indicate total amount of auto-fluorescence per mouse retina, which is a direct readout of the content of bisretionoids in RPE.

FIG. 17A shows the general in vitro methodology in which eyes from DKO mice were enucleated and dissected to separate cornea, lens, iris and neuroretina from the posterior part of the eye (eyecups). The resulting eyecups were in vitro treated with cyclodextrins for 36 hrs before observing them under the microscope (FIG. 17B).

DETAILED DESCRIPTION OF THE INVENTION

Figure 1A:
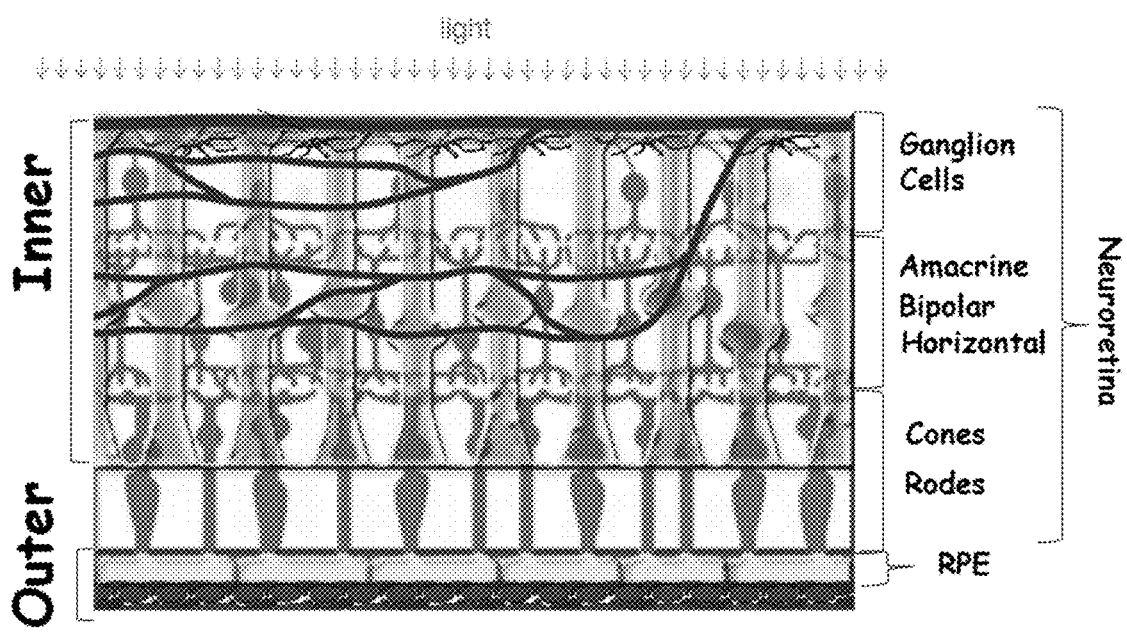
FIG. 1A: A graphical representation of components of the retina.
Figure 1B:
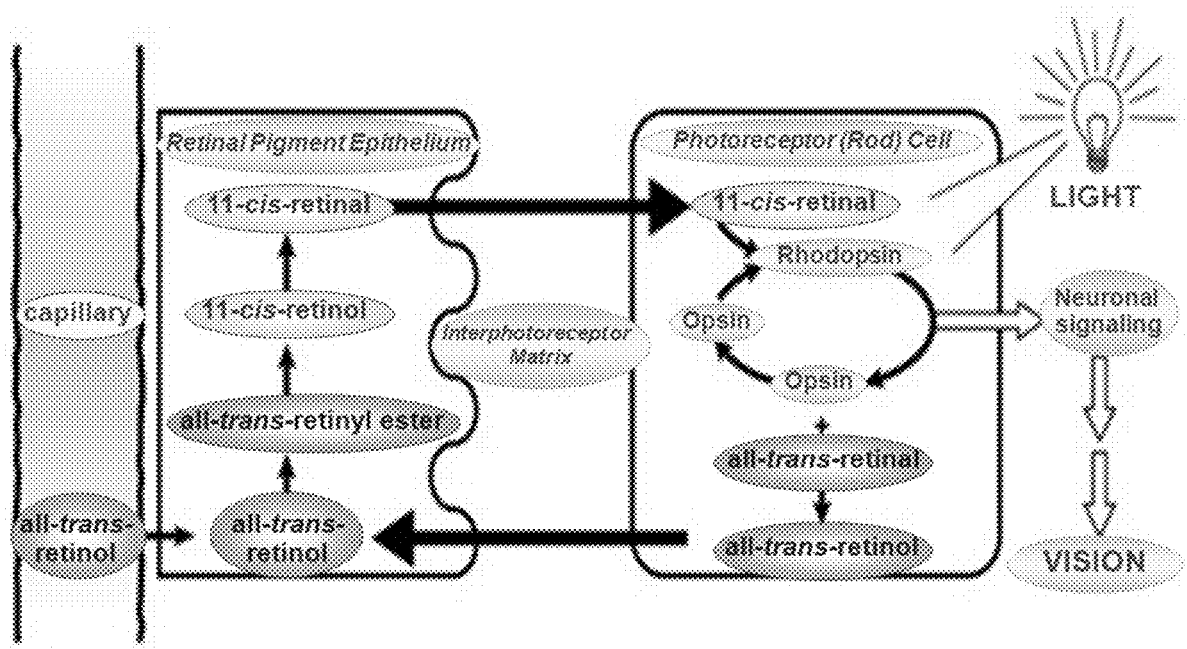
FIG. 1B. A general schematic of the light cycle.
Figure 1C:
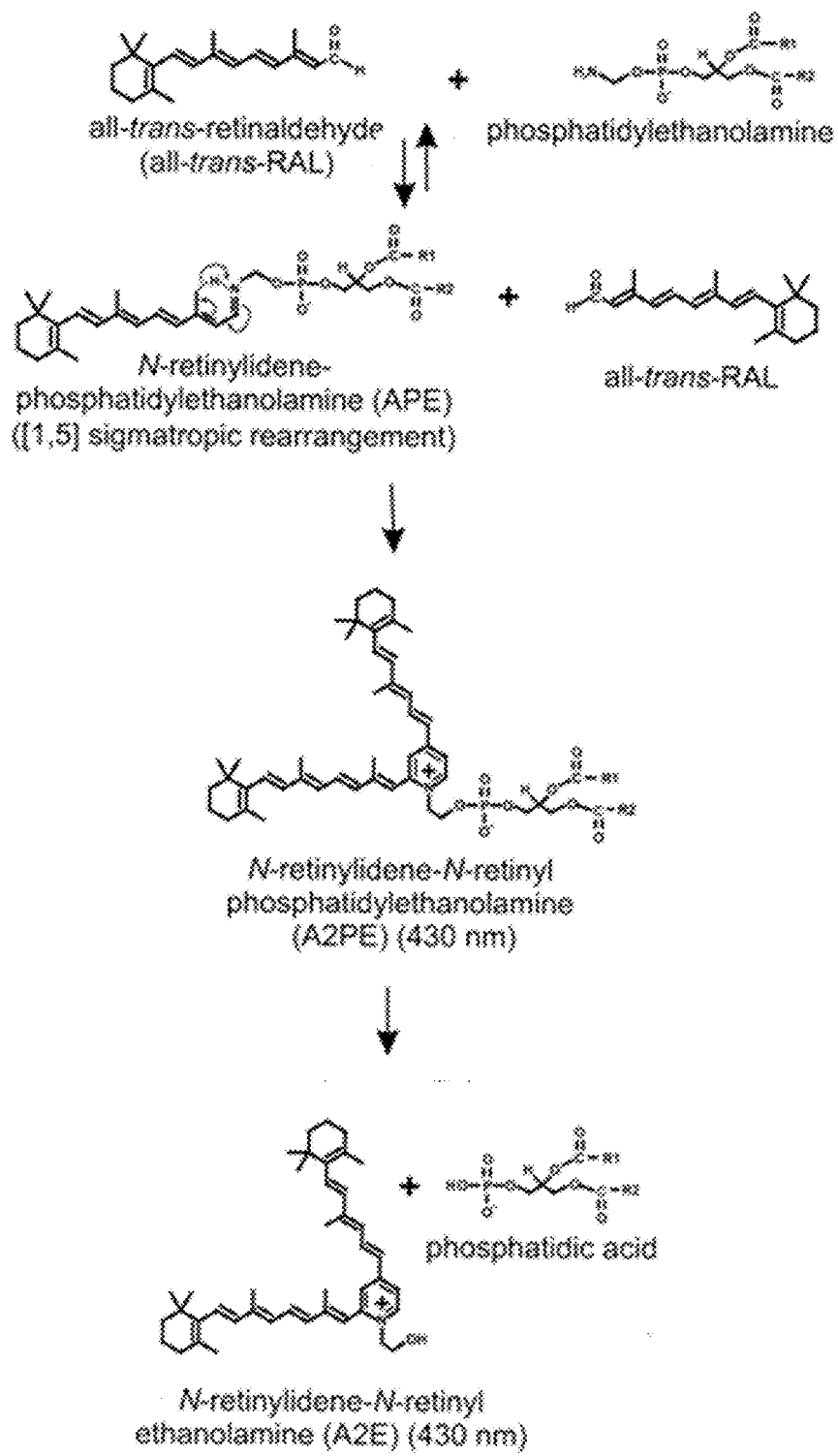
FIG. 1C. A general schematic of the non-enzymatic pathway leading to the formation of bisretinoids.
Figure 2:
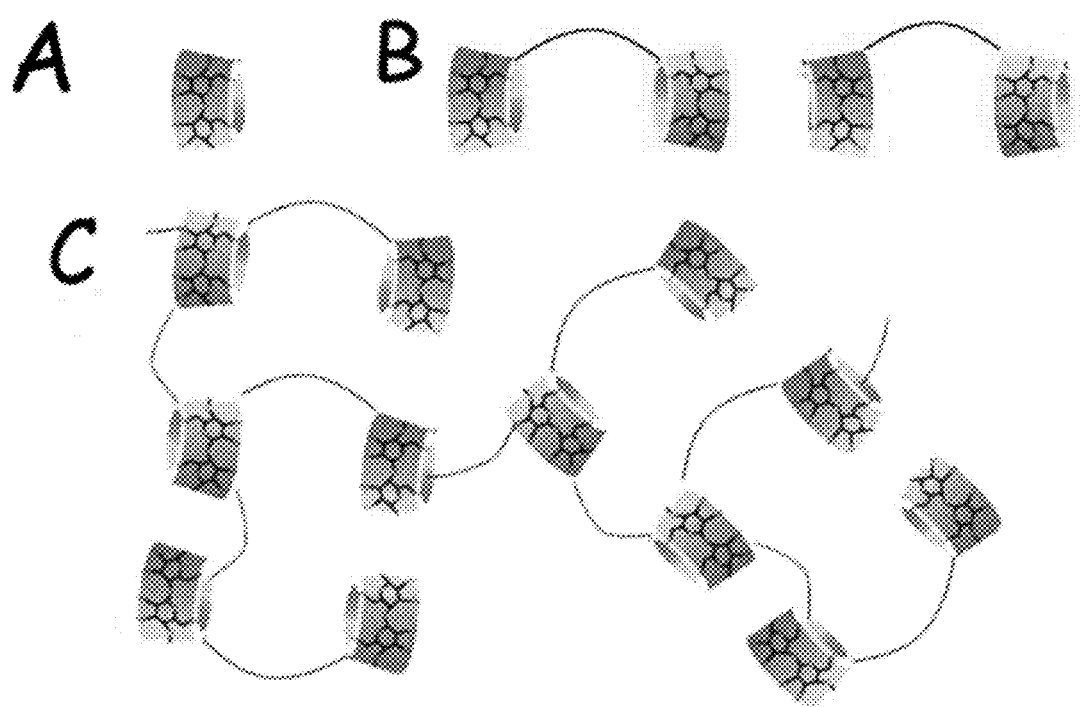
FIG. 2. Drawing showing some examples of different types of molecules containing cyclic oligosaccharides: monomeric (A), dimeric (B), and multimeric (C) cyclic oligosaccharides. The multimeric molecule may contain the same or different cyclic oligosaccharides, and linkages can be formed in a variety ways. Each conic section represents a cyclic oligosaccharide unit and each curved line represents a linking group.

In one aspect, the invention is directed to a method for treating a subject suffering from or at risk of lipofuscin-associated damage or a disease or condition associated therewith. Conditions and diseases treatable by the method described herein include any ophthalmologic or retinal disorder, condition, or disease directly or indirectly caused by the accumulation of lipofuscin in retinal pigment epithelium (RPE) cells, which may be genetic or non-genetic, such as age-related macular degeneration (AMD), Stargardt disease (SD), Best disease (BD), retinitis pigmentosa, and cone-rod dystrophy.

The term "treatment" is intended to encompass any beneficial or ameliorating effect on lipofuscin-associated damage or associated disease or condition directly or indirectly caused by the accumulation of lipofuscin bisretinoid lipid in RPE cells. Thus, the term "treatment" may also include prevention of lipofuscin-associated damage or a disease or condition directly or indirectly associated with lipofuscin-associated damage or the accumulation of lipofuscin in RPE cells in a subject that is at risk of (i.e., not yet suffering from) lipofuscin-associated damage or accumulation, or a disease or condition directly or indirectly associated therewith. The term "treatment" may also include prophylaxis, therapy, and/or cure.

Generally, the treatment considered herein has the effect of stopping, mitigating, or reversing the accumulation of lipofuscin bisretinoid lipid in RPE cells, and likewise, stopping, mitigating, or reversing the lipofuscin-associated damage or associated disease or condition. The method accomplishes this by complexing and removing lipofuscin bisretinoid lipid in RPE cells using cyclic oligosaccharides as complexing hosts (i.e., complexants). The cyclic oligosaccharides considered herein possess a cavity (i.e., binding pocket) suitable for accepting at least one lipofuscin bisretinoid lipid molecule as a guest. The result is a host-guest complex between the host cyclic oligosaccharide and guest lipofuscin bisretinoid lipid molecule. As known in the art, the interaction between host and guest is generally of a non-covalent nature, such as by hydrogen-bonding and/or van der Waals (dispersion) forces. The lipofuscin bisretinoid lipid is generally A2E, an A2E isomer, an oxidized derivative of A2E, A2-dihydropyridine-phosphatidylethanolamine, or an all-tran-sretinal dimer.

In a first embodiment, the subject suffers from lipofuscin-associated damage or a disease or condition directly or indirectly associated therewith, and the method prevents the lipofuscin-associated damage or a disease or condition associated therewith from worsening. In a second embodiment, the subject suffers from lipofuscin-associated damage or a disease or condition directly or indirectly associated therewith, and the method reverses (i.e., lessens or completely removes) the lipofuscin-associated damage or a disease or condition directly or indirectly associated therewith. In a third embodiment, the subject does not yet suffer from lipofuscin-associated damage or a disease or condition directly or indirectly associated therewith, and the method prevents, slows the onset, or lessens the severity of lipofuscin-associated damage or a disease or condition directly or indirectly associated with lipofuscin-associated damage or lipofuscin accumulation in RPE cells. The latter embodiment is particularly directed to a subject who is at risk, as determined by a medical professional, of lipofuscin-associated damage or a disease or condition directly or indirectly associated therewith or with lipofuscin accumulation in RPE cells.

The subject (i.e., patient) receiving the treatment is an animal, generally a mammal, particularly a human. Non-human animals includes all vertebrates, e.g., mammals and non-mammals, such as non-human primates, sheep, dogs, cats, cows, horses, chickens, amphibians, and reptiles. In some embodiments, the subject is livestock, such as cattle, swine, sheep, poultry, and horses, or pets, such as dogs and cats. The subject can be of any gender (i.e., male or female). The subject can also be any age, such as elderly (generally, at least or above 60, 70, or 80 years of age), elderly-to-adult transition age subjects, adults, adult-to-pre-adult transition age subjects, and pre-adults, including adolescents (e.g., 13 and up to 16, 17, 18, or 19 years of age), children (generally, under 13 or before the onset of puberty), and infants. The subject can also be of any ethnic population or genotype. Some examples of human ethnic populations include Caucasians, Asians, Hispanics, Africans, African Americans, Native Americans, Semites, and Pacific Islanders. The methods of the invention may be more appropriate for some ethnic populations, such as Caucasians, especially northern European populations, and Asian populations.

The cyclic oligosaccharide substance (i.e., active substance) being administered targets RPE cells. By "targeting" RPE cells is meant that the compound attaches to RPE cells by a covalent or non-covalent mechanism. In some embodiments, the compound is made to target RPE cells by being administered directly at, into, or in the adjacent vicinity of RPE cells, such as by injection or implantation. In other embodiments, the compound is made to target RPE cells by endowing the compound with a targeting agent that selectively targets RPE cells, and the compound may be administered at, into, or in the adjacent vicinity of RPE cells, or remotely from the RPE cells (e.g., by systemic administration). Without being bound by theory, it is believed that the cyclic oligosaccharide forms a host-guest complex with A2E or other lipofuscin bisretinoid, with the cyclic oligosaccharide as the host and the A2E or other lipofuscin bisretinoid as the guest molecule. The host-guest complex can be considered an organized chemical entity resulting from the association of two or more components held together by non-covalent intermolecular forces.

The active substance used in the method described herein has a composition having an active portion that includes one or more cyclic oligosaccharides. The cyclic oligosaccharide, as defined herein, is a chemical moiety containing at least three monosaccharide units connected directly or via one or more linkers to each other such that the monosaccharide units are arranged in a cyclic pattern that defines a relatively hydrophobic cavity capable of engaging in host-guest complex formation with A2E or related lipofuscin bisretinoid.

The number of monosaccharide units in the cyclic oligosaccharide can be, for example, four, five, six, seven, eight, nine, ten, and higher numbers (e.g., up to 12, 15, 18, or 20 units). The monosaccharide can be, for example, an aldose or a ketose, and, in addition, either a triose, tetrose, pentose, hexose, or heptose. Typically, the monosaccharide considered herein contains at least four, five, six, or seven carbon atoms. Some specific examples of monosaccharides include glucose, fructose, galactose, mannose, ribose, maltose, arabinose, xylose, erythrose, xylulose, and ribulose. In one embodiment, the cyclic oligosaccharide contains only one type of monosaccharide connected in a cyclic pattern. In another embodiment, the cyclic oligosaccharide contains more than one type of monosaccharide (e.g., two, three, or more) connected in a cyclic pattern. The monosaccharide can be in a D- or L-configuration, although the D-configuration is more typical. The monosaccharide units can be connected to each other by either an alpha or beta linkage, or a combination thereof, although an exclusive alpha linkage is more typical.

Examples of cyclic oligosaccharides suitable for use with the invention are the cyclodextrins (α-D-glucopyranoses linked at the positions 1,4 by α-linkages), cyclomannins (α-D-mannopyranose units linked at the positions 1,4 by α-linkages), the cyclogalactins (β-D-galactopyranose units linked at the 1,4 positions by β linkages) and the cycloaltrins (α-D-altropyranose units linked at the 1,4 positions by α linkages). Other examples of cyclic oligosaccharides are those having a heterogeneous monosaccharide composition, i.e., that contain a combination of two or more of the monosaccharides, such as any of those provided above.

In one set of embodiments, at least one of the monosaccharide units is derivatized by containing a modified hydroxyl group in which the hydrogen atom of the hydroxyl group is replaced with a hydrocarbon group or inorganic group. Some suitable types of hydrocarbon groups include those containing at least one, two, three, four, five, or six carbon atoms, and which can be straight-chained or branched, saturated or unsaturated, and cyclic or acyclic. Some particular hydrocarbon groups considered herein include methyl, ethyl, vinyl, n-propyl, allyl, isopropyl, cyclopropyl, n-butyl, sec-butyl, isobutyl, t-butyl, cyclobutyl, 3-butenyl, n-pentyl, isopentyl, neopentyl, cyclopentyl, cyclopentenyl, n-hexyl, isohexyl, cyclohexyl, phenyl, benzyl, naphthyl, anthracenyl, phenanthrenyl, tolyl, and xylyl groups. In one embodiment, the substituting hydrocarbon group contains only carbon and hydrogen atoms. In another embodiment, the substituting hydrocarbon group includes at least one heteroatom (e.g., at least one O, N, S, or halide atom, or combination thereof). Some examples of heteroatom-substituted hydrocarbon groups include acyl groups (e.g., acetyl and propionyl groups), sulfonyl groups (e.g., methylsulfonyl and tosyl groups), alkyleneoxy groups (e.g., ethylenoxy groups), alkylenehydroxy groups (e.g., —CH$_2$CH$_2$CH$_2$OH or —CH$_2$CH$_2$(OH)CH$_3$), alkyleneamino groups (e.g., —CH$_2$NH$_2$, —CH$_2$CH$_2$NH$_2$ or —CH$_2$CH$_2$CH$_2$NH$_2$ groups), alkylenethiol groups (e.g., —CH$_2$CH$_2$CH$_2$SH), amido groups (e.g., amide, N-methylamide, and N,N-dimethylamide groups), which link to the hydroxyl oxygen with the amido carbonyl to form a carbamate linkage, amino acids (e.g., a glycine, leucine, serine, or lysine group), dipeptides, oligopeptides, nucleobases (e.g., adenine, guanine, cytosine, thymine, and uracil groups), nucleosides, nucleotides, saccharides (e.g., monosaccharides, disaccharides, and oligosaccharides), lectins, cofactors, and combinations thereof, such as an alkyleneoxy-linked hydroxy, amino, amido, thiol, amino acid, peptide, or saccharide group. A substituting inorganic group can be, for example, a phosphate, diphosphate, triphosphate, phosphate ester, sulfate, sulfonate, metal ion (e.g., lithium, sodium, potassium, magnesium, or calcium ion), or a phosphate-monosaccharide group. Furthermore, the group can be neutral or charged. The charged group can be cationic (e.g., an ammonium group, such as a quaternary ammonium group) or anionic (e.g., a carboxylate group).

In other embodiments, at least one of the monosaccharide units can be derivatized by having one or more hydroxyl groups therein, themselves, replaced by any of the groups described above, or by other groups, such as an N-bound amino, N-bound amido (e.g., N-bound amide or acetylamide group), or a thiol group. In yet other embodiments, at least one of the monosaccharide units can be derivatized by having one or more hydroxyl groups replaced with a hydrogen atom, thereby resulting in a deoxysaccharide unit.

By methods well-known in the art, several of the groups described above, particularly those containing one or more heteroatoms (e.g., amino, amido, ester, thiol, and aldehydic groups) can be used as reactive groups for attaching the cyclic oligosaccharide to another chemical entity, i.e., to a polysaccharide, another cyclic oligosaccharide, a cell-targeting agent, a fluorophore, or other group, either directly or via a linker to any other these groups. Any of the other chemical entities considered as a part of the composition herein (e.g., cell-targeting agent, fluorophore, or other group) can contain, or be derivatized to contain, any such reactive groups for the purpose of attaching these groups to each other or to the cyclic oligosaccharide.

Particularly considered herein as cyclic oligosaccharides are the cyclodextrins. As is well-known in the art, cyclodextrins are typically composed of five or more glucose (i.e., glucopyranoside) units connected in a ring structure, linked as in amylose by alpha 1-4 (i.e., alpha(1→4)) bonds. The cyclodextrins considered herein can conveniently be represented by the following generic formula:

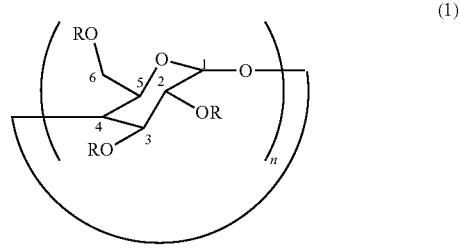

(1)

In generic formula (1) above, the R groups can be independently selected from any of the groups described above, including hydrogen atom, hydrocarbon groups, heteroatom-substituted hydrocarbon groups, inorganic groups, and biochemically-relevant groups. In some embodiments, all of the R groups in the formula are the same, while in other embodiments, at least one of the R groups in the formula is chemically different from other R groups. In further or alternative embodiments, one or more of the OR groups can be replaced by any of the groups described above. In some embodiments, the cyclodextrin (or, more generally, cyclic oligosaccharide) is attached to a polysaccharide, wherein at least one (e.g., one, two, or three) of the R groups can represent either a direct bond or a linker that bonds or links, respectively, the cyclodextrin (or, more generally, cyclic oligosaccharide) to the polysaccharide. When generic formula (1) represents a cyclic oligosaccharide, the shown glucose groups can be generically replaced by one or a combination of any of the monosaccharide groups described above. The subscript n denotes the number of monosaccharide units, and can be any number above 3, but more typically a number of 4, 5, 6, 7, 8, 9, or 10, or a particular range therein. The arc shown in generic formula (1) denotes a cyclic arrangement of monosaccharide units.

As a consequence of the chair conformation of the sugar units, all secondary RO— groups (at C-2, C-3) are located on one side of the ring (large rim), while all the primary RO— groups at C-6 are situated toward the exterior on the other side (large rim). As a result, the external faces are hydrophilic, making the cyclodextrins water-soluble. In contrast, the internal portions (i.e., cavities) of the cyclodextrins are much less hydrophilic (i.e., relatively hydrophobic), since they contain the hydrogen of atoms C-3 and C-5, and ether groups.

The diameter of the internal cavity of the cyclic oligosaccharide depends on the number of sugar (e.g., D-glucopyranose) units it contains. The average interior diameters for α-, β- and γcyclodextrins are typically about 0.66, 0.70, and 0.86 nm, respectively.

Some particular cyclodextrin structures are shown in the following sub-generic formulas:

(2)

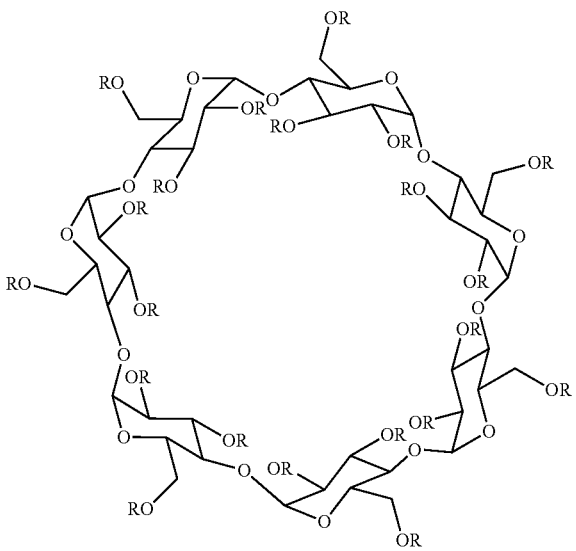

(3)

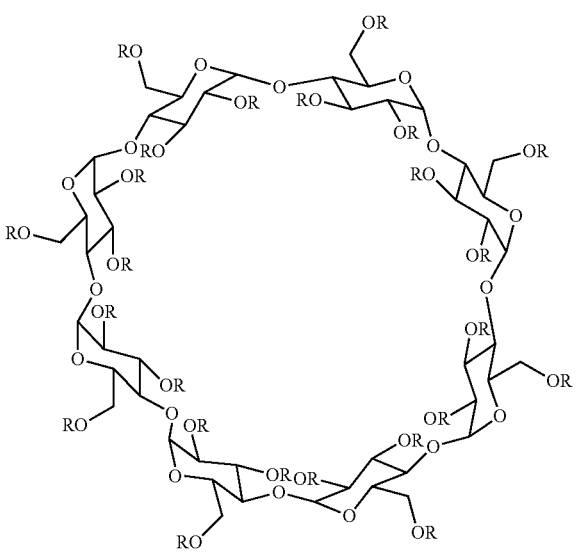

(4)

In formulas (2), (3), and (4), R is as defined above for generic formula (1). Furthermore, any of formulas (2), (3), and (4) can generically represent any cyclic oligosaccharide with the indicated number of sugar units, by replacing one or more of the shown glucose groups with one or a combination of any of the monosaccharide groups described above.

The physico-chemical properties of the cyclodextrin derivatives depend strongly on the kind and the degree of substitution. For example, their solubility in water ranges from insoluble, i.e., for triacetyl-beta-cyclodextrin, to 147% soluble (w/v), i.e., for G-2-beta-cyclodextrin. In addition, cyclodextrins can be soluble in different types of organic solvents. For purposes of the instant invention, the cyclic oligosaccharide or dimeric, trimer, higher multimeric, or polymeric form thereof is preferably substantially or completely soluble in water (i.e., at least 50%, 60%, 70%, 80%, 90%, or 100% w/v).

The synthesis of cyclic oligosaccharides is well known in the art, and numerous types are commercially available.

Chemical modification of cyclodextrins can be made directly on the native (alpha, beta, gamma) cyclodextrin rings by reacting a chemical reagent (nucleophiles or electrophiles) with a properly functionalised cyclodextrin (Adair-Kirk, T. L., et al., *Nat. Med.,* 14(10): pp. 1024-5, 2008; Khan, A. R., et al., *Chem. Rev.,* 98(5): pp. 1977-1996, 1998). To date, more than 1,500 cyclodextrin derivatives have been made by chemical modification of native cyclodextrins. Cyclodextrins can also be prepared by de novo synthesis, starting with glucopyranose-linked oligopyranosides. Such a synthesis can be accomplished by using various chemical reagents or biological enzymes, such as cyclodextrin transglycosylase. An overview of chemically modified cyclodextrins as drug carriers in drug delivery systems is described, for example, in Stella, V. J., et al., *Toxicol. Pathol.,* 36(1): pp. 30-42, 2008, the disclosure of which is herein incorporated by reference in its entirety. U.S. Pat. Nos. 3,453,259 and 3,459,731 describe electroneutral cyclodextrins, the disclosures of which are herein incorporated by reference in its entirety. Other derivatives include cyclodextrins with cationic properties, as disclosed in U.S. Pat. No. 3,453,257; insoluble crosslinked cyclodextrins, as disclosed in U.S. Pat. No. 3,420,788; and cyclodextrins with anionic properties, as disclosed in U.S. Pat. No. 3,426,011, the disclosures of which are all hereby incorporated by reference in their entirety. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin, as disclosed, for example, in U.S. Pat. No. 3,426,011, supra. Sulfoalkyl ether cyclodextrin derivatives have also been described, e.g., in U.S. Pat. No. 5,134,127, the disclosure of which is hereby incorporated by reference in its entirety. In some embodiments, the cyclic oligosaccharide can have two or more of the monosaccharide units replaced by triazole rings, which can be synthetized by the Azide-alkyne Huisgen cycloaddition reaction (Bodine, K. D., et al., *J. Am. Chem. Soc.,* 126(6): pp. 1638-9, 2004).

Figures 8A, 8B:
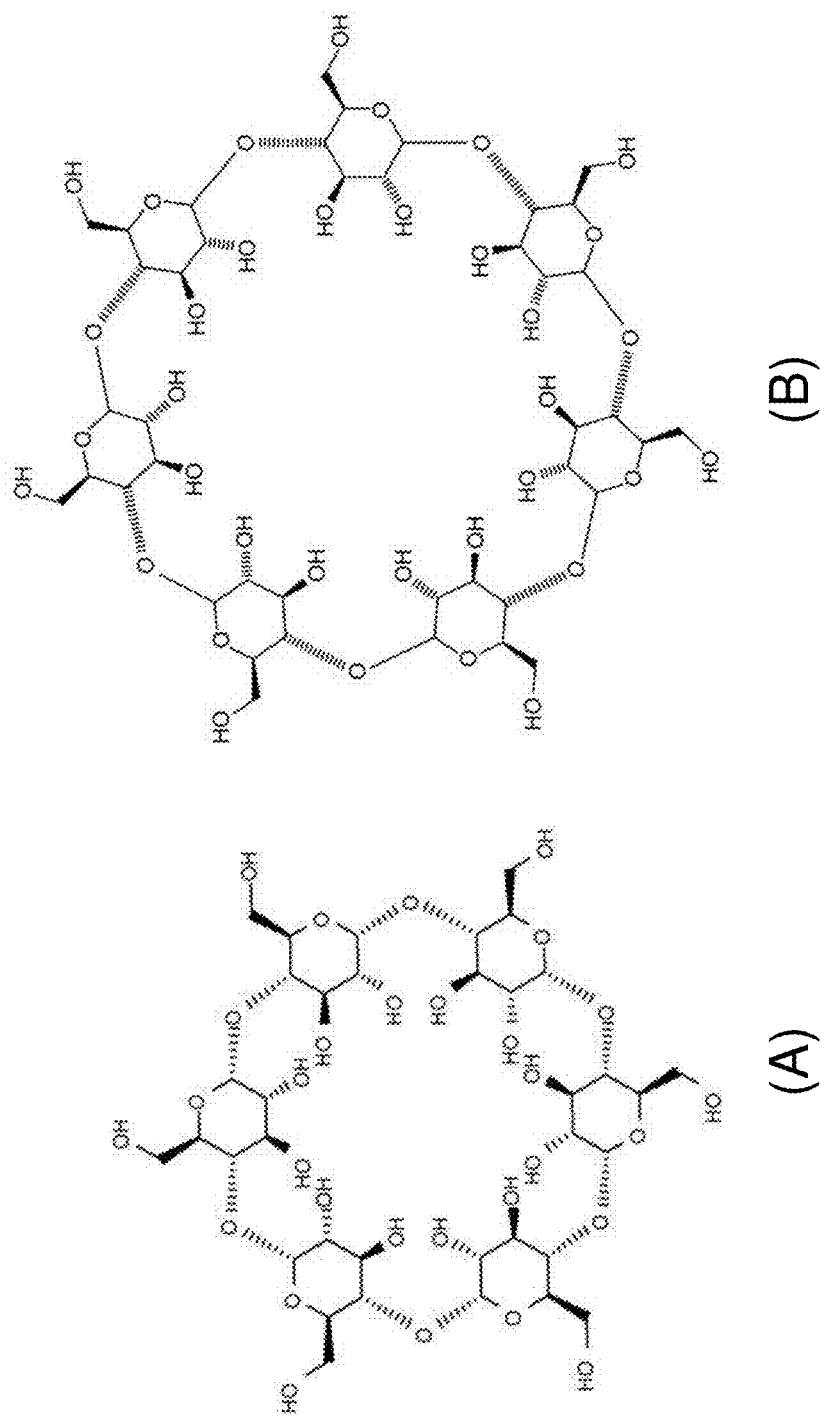
FIGS. 8A-8D. Drawings depicting: alpha-cyclodextrin (FIG. 8A), beta-cyclodextrin (FIG. 8B), gamma-cyclodextrin (FIG. 8C) screened for interaction with A2E, as well as an exemplary structure (FIG. 8D) of the multimeric cyclodextrins that interacted most strongly with A2E. CD in FIG. 8D is preferably either a beta- or gamma-cyclodextrin.
Figure 8C:
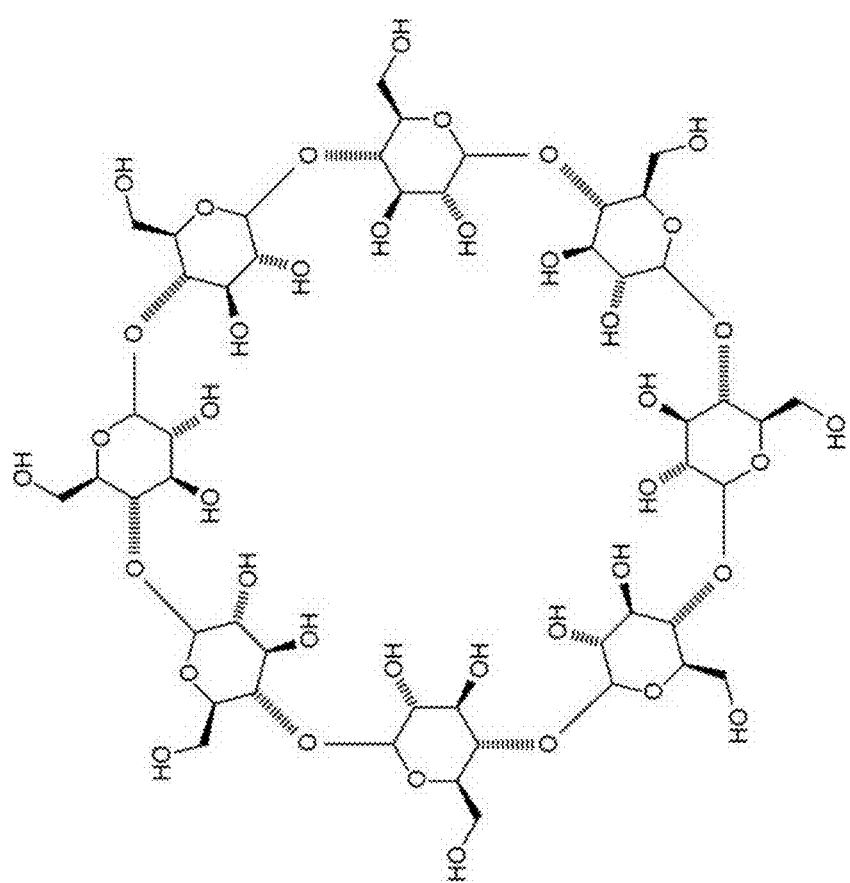
Figure 8D:
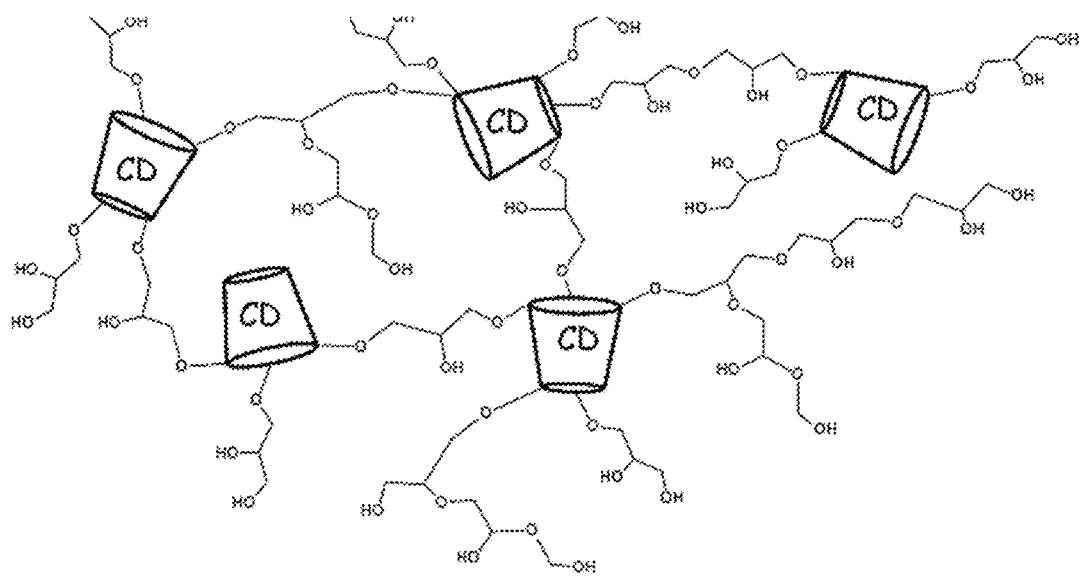
Figure 10:
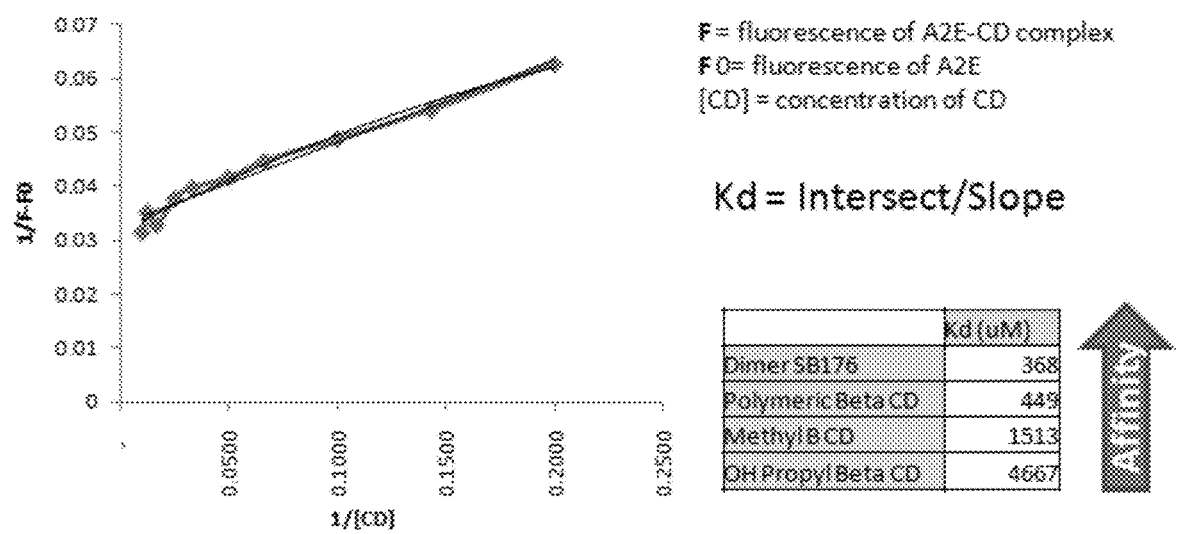
FIG. 10. Measurement of the affinity of cyclodextrins for A2E using the Benesi-Hildendrand method. The method utilized to measure the affinity of cyclodextrins for A2E was also used comparatively to measure their affinity for DHE, a fluorescent analog of cholesterol. The $K_d$s of lead compounds shown in FIG. 7 are displayed in the table in the lower right.
Figure 11:
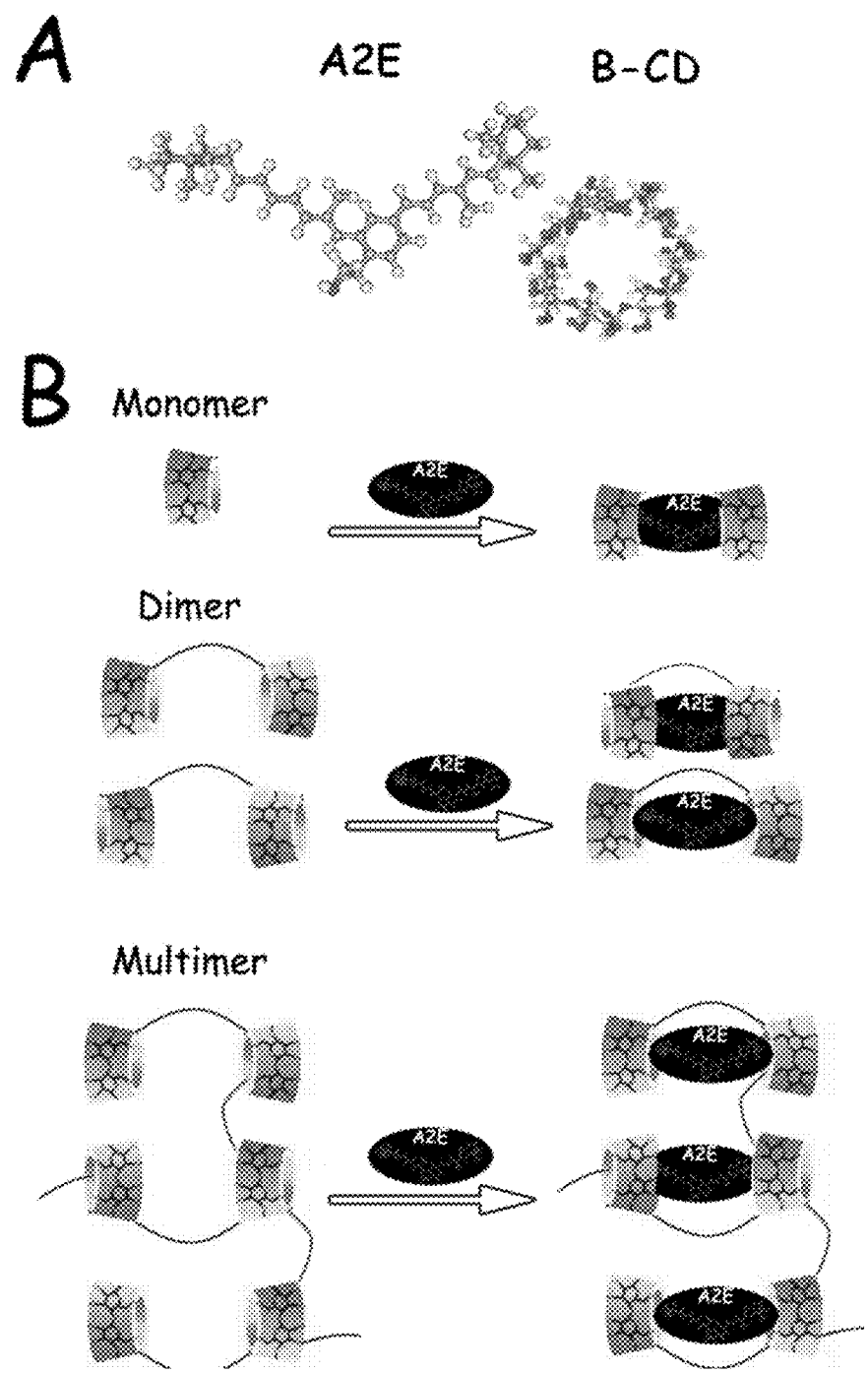
FIG. 11. In silico modeling structures of A2E and beta-cyclodextrin using PyMol software (top), and possible modes in which a cyclodextrin monomer, dimer, or multimer may bind with A2E (bottom). The foregoing analysis predicts higher stability of A2E cyclodextrin complexes when two or more oligosaccharide rings interact with A2E.

Although the cyclic oligosaccharide can be used in monomeric form, in some embodiments, dimerization, trimerization, or higher multimerization, or even polymerization, increases their ability to form more stable complexes with A2E, as shown, for example, in FIG. 10. Typically, dimeric, trimeric, and higher multimeric cyclic oligosaccharides contain linkers that function as bridges between cyclic oligosaccharide units, as shown, for example, in FIG. 8D.

In some embodiments, at least two or more cyclic oligosaccharides are bound to each other (i.e., interconnected) via one or more linkers. Methods for functionalizing a cyclic oligosaccharide with a linking group are well-known in the art. Reference is made, for example, to (a) Mocanu G. et al., "Cyclodextrin polymers," *J. Bioact. Compat. Pol.,* 2001; 16:315-342; (b) Liu Y., et al., "Cooperative binding and multiple recognition by bridged bis(b-cyclodextrin)s with functional linkers", *Acc. Chem. Res.,* 2006; 39:681-691; (c) Ozmen E. Y., et al., "Synthesis and characterization of cyclodextrin-based polymers as a support for immobilization of *Candida rugosa* lipase," *J. Mol. Catal.* B-Enzym., 2009; 57:109-114; (d) Trotta F. et al., "Characterization and applications of new hyper-cross-linked cyclodextrins," *Compos. Interface,* 2009; 16:39-48, the disclosures of which are herein incorporated by reference in their entirety. For example, a linker group containing a portion reactive to a hydroxyl group (e.g., a carboxyl group, preferably activated by a carbodiimide) can be reacted with the cyclodextrin to form a covalent bond thereto. Alternatively, one or more hydroxyl groups of the cyclodextrin can be activated by known methods (e.g., tosylation) to react with a reactive group (e.g., amino group) on the linker.

Since the linker attaches at least two chemical entities to each other, the linker generally contains two reactive portions made to react and bond with each chemical entity. In one embodiment, a double-reactive linker is first attached to a cyclic oligosaccharide (e.g., cyclodextrin) to produce a linker-cyclodextrin compound that is isolated, and then the remaining reactive portion of the linker in the linker-cyclodextrin compound is subsequently reacted with a second linker or molecule (e.g., a second cyclodextrin or a polysaccharide). In the foregoing embodiment, the second reactive portion of the linker is generally protected during reaction of the first reactive group, or alternatively, protection is not necessary in an embodiment where the first and second reactive portions of the linker react with the two molecules differently. Particularly by the latter embodiment, a double-reactive linker may be reacted with both molecules simultaneously to link them together. In other embodiments, the linker can have additional reactive groups in order to link to other molecules, such as another cyclodextrin unit, polysaccharide, or a cell-targeting or fluorophore.

Numerous double-reactive linkers are known in the art. Such linkers can be used for linking any of a variety of groups together when the groups possess, or have been functionalized to possess, groups that can react and link with the reactive linker. Some groups capable of reacting with double-reactive linkers include amino, thiol, hydroxyl, carboxyl, ester, and alkyl halide groups. For example, amino-amino coupling reagents can be employed to link a cyclic oligosaccharide with a polysaccharide (or, for example, any of these groups with a fluorophore or with each other) when each of the groups to be linked possess at least one amino group. Some examples of amino-amino coupling reagents include diisocyanates, alkyl dihalides, dialdehydes, disuccinimidyl suberate (DSS), disuccinimidyl tartrate (DST), and disulfosuccinimidyl tartrate (sulfo-DST), all of which are commercially available. In other embodiments, amino-thiol coupling agents can be employed to link a thiol group of one molecule with an amino group of another molecule. Some examples of amino-thiol coupling reagents include succinimidyl 4-(N-maleimidomethyl)-cyclohexane-1-carboxylate (SMCC), and sulfosuccinimidyl 4-(N-maleimidomethyl)-cyclohexane-1-carboxylate (sulfo-SMCC). In yet other embodiments, thiol-thiol coupling agents can be employed to link groups bearing at least one thiol group.

In some embodiments, one or more linkers attach together two or more cyclic oligosaccharides, and one or more other linkers attach a cell-targeting agent with one or more of the cyclic oligosaccharides. In other embodiments, a linker that attaches cyclic oligosaccharides with each other also links at least one of the cyclic oligosaccharides with a cell-targeting agent. In further embodiments to any of the foregoing embodiments, a separate linker may be employed to link a fluorophore or other functional group with a cyclic oligosaccharide, or alternatively, any of the linkers described above may also be covalently attached to a fluorophore or other functional entity. The other functional entity can be, for example, a drug or prodrug that would be hydrolyzed and/or otherwise released upon reaching the targeted cell. In some embodiments, such a drug or prodrug is excluded from the cyclic oligosaccharide. In any of the exemplary embodiments provided above, the linker may in addition or alternatively link a cyclic oligosaccharide to a polysaccharide unit, and/or link a targeting agent, fluorophore, or other functional entity to a polysaccharide unit that functions as a pendant group or linker in a cyclic oligosaccharide.

In some embodiments, the linker is as small as a single atom (e.g., an —O—, —CH$_2$—, or —NH— linkage), or two or three atoms in length (e.g., an amido, ureido, carbamato, ester, carbonate, sulfone, ethylene, or trimethylene linkage). In other embodiments, the linker provides more freedom of movement by being at least four, five, six, seven, or eight atom lengths, and up to, for example, 10, 12, 14, 16, 18, 20, 22, 24, 26, 28, or 30 atom lengths.

In one embodiment, the linker is a hydrocarbon linker, e.g., as derived from any of the hydrocarbon groups described above by removal of two or more hydrogen atoms therefrom (thus resulting in two or more linking bonds therein). Some examples of hydrocarbon linkers include methylene (—CH$_2$—), ethylene (—CH$_2$CH$_2$—), trimethylene (—CH$_2$CH$_2$CH$_2$—), tetramethylene, pentamethylene, hexamethylene, o-, m-, and p-phenylene, and vinylene.

The hydrocarbon linker may or may not also include heteroatoms. Furthermore, the heteroatoms may or may not be linking atoms. In a particular embodiment, the hydrocarbon linker contains one, two, three, or more amino groups. Some examples of amino-containing linkers include 1,2-ethylenediamine, 1,3-trimethylenediamine, 1,4-tetramethylenediamine, 1,5-pentamethylenediamine, 1,6-hexamethylenediamine, diethylenetriamine, triethylenetetramine, and diaminobenzene linkers. In another particular embodiment, the hydrocarbon linker contains one, two, three, or more oxygen-linking (i.e., —O—) atoms or hydroxy groups. Some examples of such linkers include ethylene glycol, diethylene glycol, triethylene glycol, 2-hydroxypropane, 2,3-dihydroxybutane, dihydroxybenzene, and the polyethylene glycol (i.e., PEG) linkers. In other particular embodiments, the linkers include one, two, three, or more carbonyl groups. Some examples of such linkers include methyl dicarbonyl, ethylene-1,2-dicarbonyl, propylene-1,3-dicarbonyl, and the like.

The linker can also be or include a biological group, such as, for example, a nucleobase, nucleoside, nucleotide, dinucleotide, trinucleotide, tetranucleotide, a higher oligonucleotide, amino acid, dipeptide, tripeptide, tetrapeptide, pentapeptide, hexapeptide, a higher oligopeptide, saccharide, disaccharide, trisaccharide, tetrasaccharide, a higher oligosaccharide, lipid, or fatty acid.

In particular embodiments, the linker is a rigid linker. A rigid linker may be beneficial in some embodiments by reducing the degree of freedom of a linked molecule, or forcing at least two linked groups to remain at fixed distances from each other or from another molecule. Some examples of rigid linkers are those containing aromatic or heteroaromatic rings, such as linkers that include benzene, naphthalene, styrene, divinylbenzene, biphenyl, triphenyl, or other aromatic rings or polycyclic ring systems.

In a particular set of embodiments, the linker has a structure represented by the following generic formula:

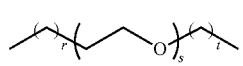

(5)

In formula (5) above, subscripts r, s, and t can independently be 0 or an integer of at least 1, provided that at least one of r, s, and t is not 0. Generally, each end of the linker generally also includes a heteroatom-containing group through which a covalent bond is formed between the linker and groups that are linked. As discussed earlier, such heteroatom-containing groups include, for example, oxo (—O—), amino (e.g., —NH—, or —N(CH$_3$)—), amido (e.g., —C(O)NH— or —C(O)N(CH$_3$)—), ester, ureido, carbonato, sulfanoto, and phosphonato groups. In different embodiments, r, s, and t are independently selected from 0, or an integer of 1, 2, 3, 4, 5, 6, 7, 8, 9, 10, 11, 12, 13, 14, 15, or 16, or selected to be within a range therein, provided that at least one of r, s, and t is not 0. In one set of embodiments, r and t are 0, and s represents any of the foregoing non-zero numbers or possible ranges therein. In another set of embodiments, r is 0, while s and t independently represent any of the foregoing non-zero numbers or possible ranges therein. In another set of embodiments, s is zero while at least one of r and t represents any of the foregoing non-zero numbers or possible ranges (thereby resulting in an alkylene structure for formula 5). In another set of embodiments, r, s, and t independently represent any of the foregoing non-zero numbers or possible ranges therein. In particular embodiments, r and t are independently 1, 2, 3, or 4, or a subset therein, while s is selected from any of the foregoing non-zero numbers or possible ranges therein.

In some embodiments, the linker is a polysaccharide. As defined herein, a polysaccharide is a chemical moiety containing a multiplicity (e.g., at least 10, and more typically at least 100) of monosaccharide units connected to each other in a linear and/or branched (i.e., non-cyclic) arrangement. In one embodiment, the polysaccharide is a homopolysaccharide by having all of the monosaccharide units as the same type (e.g., all glucose units). In another embodiment, the polysaccharide is a heteropolysaccharide by having different types of monosaccharide units. The polysaccharide considered herein possesses, for example, at least 10, 20, 50, 100, 200, 500, 1000, 5000, 10000, 50000, 100000, 150000, 200000, or higher number of units, or alternatively, molecular weights (or average molecular weights) of at least 100, 200, 500, 1000, 5000, 10000, 20000, 30000, 40000, 50000, 60000, 70000, 80000, 90000, 100000, 150000, 200000, or 500000 Daltons (Da), or the polysaccharide possesses a number of units or molecular weight within a range bounded by any of the foregoing exemplary values. One or more of the monosaccharide units of the polysaccharide can be derivatized in the same manner as described above for the cyclic oligosaccharide. In a particular embodiment, the polysaccharide is functionalized with one, two, three, or higher multiplicity of amino groups. Such a polysaccharide is denoted herein as an "amino polysaccharide".

Particularly considered herein as linkers are those polysaccharides constructed solely of glucose units (i.e., a glucan polysaccharide). The glucan polysaccharide can be an alpha-glucan or beta-glucan polysaccharide, although the glucan polysaccharide is more commonly an alpha-glucan polysaccharide. A particular class of alpha-glucan polysaccharide considered herein is dextran. As known in the art, a dextran generally consists predominantly of glucose molecules linked predominantly or exclusively by alpha-1,6-glycosidic linkages. Depending on the type of dextran used, the dextran can contain any of a broad range of branching. The branching generally results from alpha-1,4 glycosidic linkages, and in some cases, alpha-1,2 and alpha-1,3 glycosidic linkages. Other types of alpha-glucan polysaccharide considered herein are the starches (e.g., amylose and amylopectin), glycogen, and pullulan. Some particular classes of beta-glucan polysaccharides considered herein include cellulose, hemicellulose, cellodextrin, chrysolaminarin, lentinan, and zymosan. In some embodiments, at least a portion of the glucose units can be derivatized, such as found in chitin (i.e., a polymer of N-acetylglucosamine). Other derivatized glycans include the glycosaminoglycans, such as chondroitin sulfate, dermatan sulfate, heparin, heparan sulfate, hyaluronic acid, and keratan sulfate.

Other classes of polysaccharides considered herein are the fructans and galactans. Some examples of fructans include the inulins, fructooligosaccharides, and Levan polysaccharide (a homopolysaccharide of fructose with varying degrees of branching). An example of a galactan is the class of galactooligosaccharides.

A particular example of a heteropolysaccharide considered herein is the class of arabinoxylans, which are copolymers of arabinose and xylose. Another heteropolysaccharide considered herein is agarose.

In one set of embodiments, the polysaccharide consists solely of monosaccharide units. In another set of embodiments, the polysaccharide can also include a non-saccharide moiety. For example, the polysaccharide can be a glycoprotein or proteoglycan by containing a proteinaceous component, or the polysaccharide can be a lipopolysaccharide by containing a lipid component.

In some embodiments, the cyclic oligosaccharide (or a dimeric, trimeric, multimeric, or polymeric form thereof) is covalently bound to one or more polysaccharide units. The polysaccharide units may be attached to the cyclic oligosaccharide as a pendant group (i.e., non-linker) or as a linker. In different embodiments, at least one, two, three, four, five, six, and up to, for example, 10, 15, 20, or 30 cyclic oligosaccharides are bound to a polysaccharide unit. The cyclic oligosaccharide can be directly bound or linked via a linker to the polysaccharide by any one or more suitable atoms present on the cyclic oligosaccharide. For example, in different embodiments, the cyclic oligosaccharide can be bound to the polysaccharide by one or more of the carbon atoms of the cyclic oligosaccharide, e.g., by replacement of one of the hydroxyl groups of the cyclic oligosaccharide by a binding atom of the polysaccharide or by a binding atom of a linker group linked to the polysaccharide. Alternatively, the cyclic oligosaccharide can be bound to the polysaccharide by one or more of its hydroxyl groups (i.e., oxygen atoms), or the cyclic oligosaccharide can be bound to the polysaccharide by one or more heteroatom-containing groups present on the cyclic oligosaccharide. In the same manner, the polysaccharide can be directly bound or linked via a linker to the cyclic oligosaccharide by any one or more suitable atoms present on the polysaccharide.

In particular embodiments, at least one cell-targeting agent is attached to the cyclic oligosaccharide, either as an integral moiety of the cyclic oligosaccharide, or bound directly to the cyclic oligosaccharide or indirectly via a linker. In one set of embodiments, the cell-targeting agent is embedded within the structure of the cyclic oligosaccharide, e.g., as cyclomannins or cyclic oligosaccharides containing one or more mannoses with phosphate groups introduced at position 6 of mannose rings. A generalized structure depicting the foregoing embodiment is provided by the following representation:

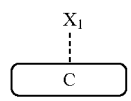

(6)

In the above representation, C represents a cyclic oligosaccharide. In particular embodiments, at least one of $X_1$ represents a cell-targeting agent, such as M6P. Each of $X_1$ can also represent a multiplicity (e.g., two, three, or more) of any of the foregoing groups. The dashed line to $X_1$ indicates that these groups may or may not be present, and, if present, may be attached to any portion of the group to which they are bound. The representation in formula (6) is meant to be non-limiting by depicting a minimum set of features that can be expanded upon in numerous ways. For example, additional embedded cyclic oligosaccharides may be included, or additional C or other groups (e.g., one or more pendant or linking polysaccharide groups) may be bound to C.

In another set of embodiments, two cyclic oligosaccharides (C) are connected by a linker (L). A generalized structure depicting the foregoing embodiment is provided by the following representation:

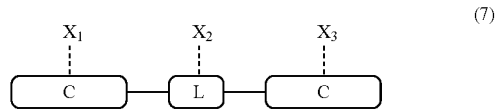

(7)

In the above representation, each C may be identical or different. In particular embodiments, at least one of $X_1$, $X_2$, and $X_3$ represents a cell-targeting agent. One or more of $X_1$, $X_2$, and $X_3$ can alternatively, or in addition (i.e., optionally) represent a fluorophore, or other functional moiety. Each of $X_1$, $X_2$, and $X_3$ can also represent a multiplicity (e.g., two, three, or more) of any of the foregoing groups. The dashed lines to each of $X_1$, $X_2$, and $X_3$ indicate that these groups may or may not be present, and, if present, may be attached to any portion of the group to which they are bound. The continuous line between L and C represents at least one direct bond. The representation in formula (7) is meant to be non-limiting by depicting a minimum set of features that can be expanded upon in numerous ways. For example, an additional P group may be bound to $X_2$ and/or $X_3$, or an additional C group may be bound to $X_1$, $X_2$, and/or $X_3$.

In another set of embodiments, two cyclic oligosaccharides rings are pendant to at least one (L) linker chain. A generalized structure depicting the foregoing embodiment is provided by the following representation:

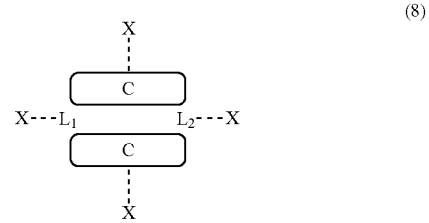

(8)

The above representation corresponds to a subset of dimers of cyclic oligosaccharide rings defined above. C may represent more than one type of cyclic oligosaccharides bound to each other either directly or via one or more linkers $L_1$, $L_2$. $L_1$ represents one or more linkers of one or more than one type. $L_2$ represents none or one linker. $L_1$ and $L_2$ can be the same or different. In particular embodiments, X represents a cell-targeting agent as defined above. One or more of X can be present in the cyclic oligomer and/or in the linker.

Alternatively, or in addition (i.e., optionally) X represents a fluorophore, or other functional moiety. In this embodiment, X is not considered as another L group. Each of X can also represent a multiplicity (e.g., two, three, or more) of any of the foregoing groups. The dashed lines to each X indicate that these groups may or may not be present, and, if present, may be attached to any portion of the group to which they are bound. The contact between L and C represents at least one direct bond. The representation in formula (8) is meant to be non-limiting by depicting a minimum set of features that can be expanded upon in numerous ways. The representation in formula (8) is meant to be non-limiting by depicting a minimum set of features that can be expanded upon in numerous ways. For example, additional embedded cyclic oligosaccharides may be included, or multiple L groups may be used to be bind C cyclic units.

Figure 3A:
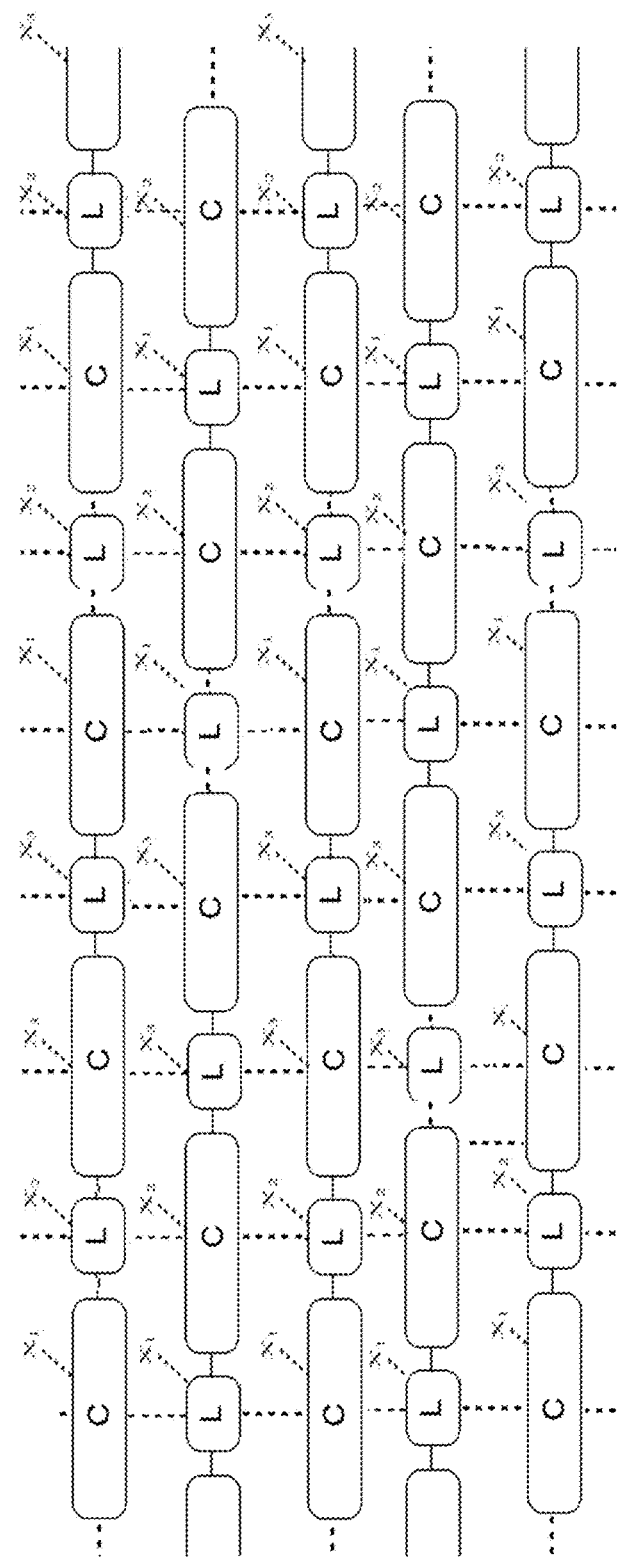
FIGS. 3A-3C.

In another set of embodiments, the active composition has an active portion that includes three or more cyclic oligosaccharides (multimer). A generalized structure depicting the foregoing embodiment is provided in FIG. 3A. In FIG. 3A, C represents a cyclic oligosaccharide and L represents a linker. In particular embodiments, at least one C contains attached or embedded cell-targeting sequences, such as Mannose-6-P, or in the case of mannose-containing cyclic oligosaccharides, a phosphate group at position 6 of a mannose ring. Each of the solid lines connecting C with L represents at least one direct bond or linker. The dashed lines connecting C to L indicate that these links may or may not be present, and, if present, may be attached to any portion of the group to which they are bound. The representation in FIG. 3A is meant to be non-limiting by depicting a minimum set of features that can be expanded upon in numerous ways. For example, additional embedded cyclic oligosaccharides may be included, or multiple L groups may be used to link two C units. The linker group (L) can be, for example, acryloyl, phenylacetylene, polyphenylene, or ethynylene poly(maleic anhydride) polyallylamine, poly(ethyleneimine) dendrimers, chitosane, and alginate. In a particular embodiment, FIG. 3A represents epichlorohydrin linear multimers threaded on PEG (molecular tubes). The cyclic oligosaccharide multimers can be synthesized by, for example: (1) radical polymerization of monofunctional CD monomers, (2) polymer-analogous reaction of polymers with cyclic oligosaccharides, or (3) partial crosslinking of cyclic oligosaccharides.

Figure 3B:
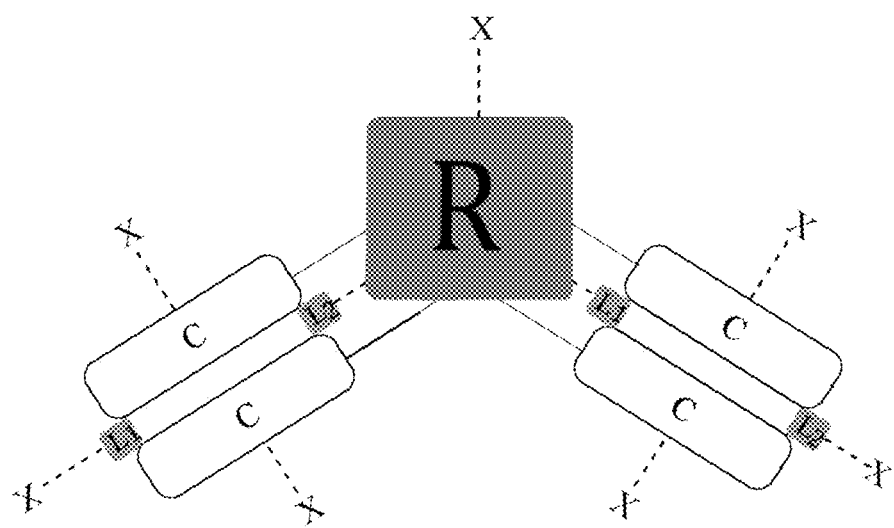
Figure 3C:
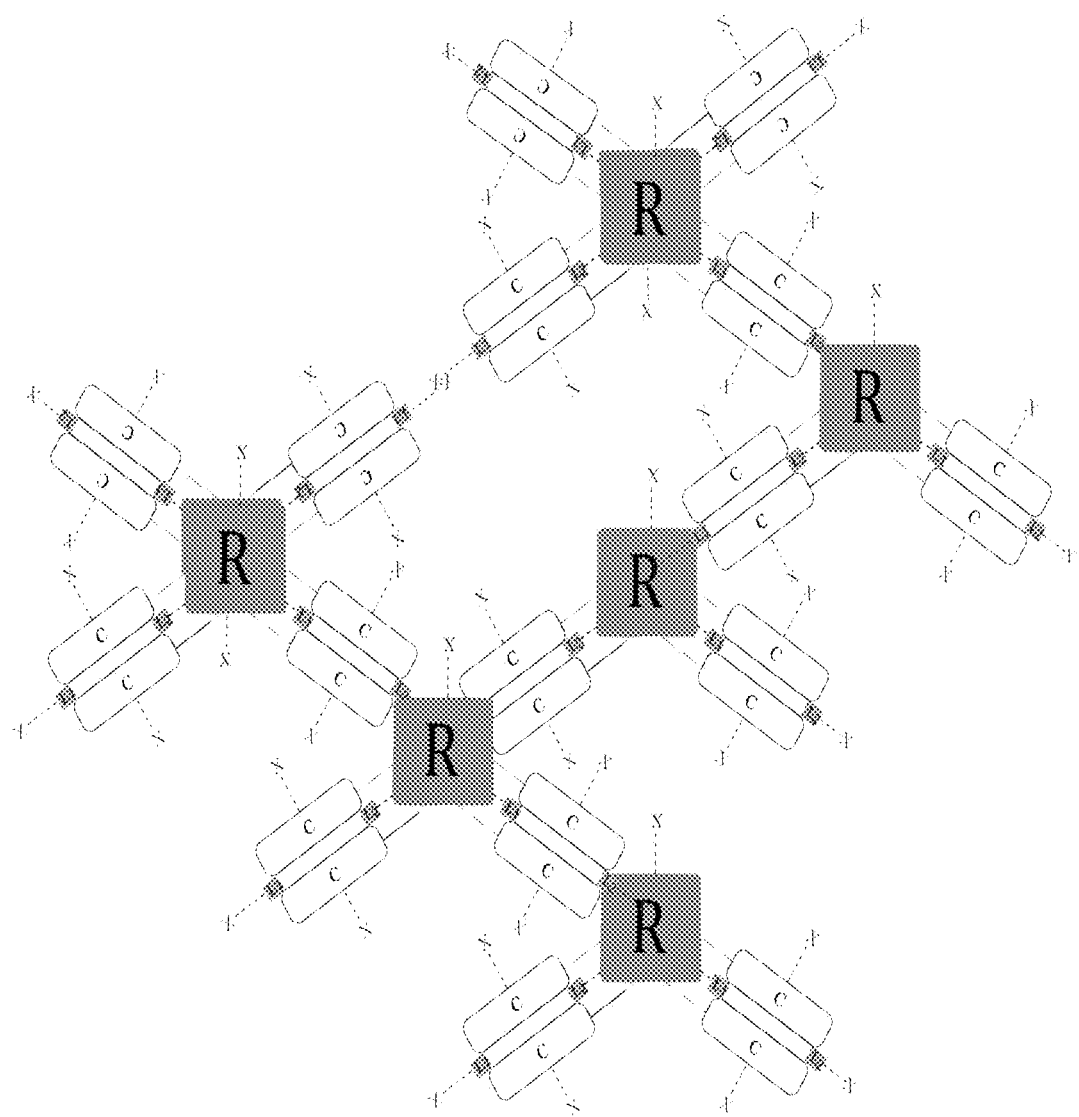

In another set of embodiments, the invention is directed to a composition having an active portion therein that includes two or more dimers of cyclic oligosaccharide rings (multimer). Some generalized structures depicting the foregoing embodiments are provided in FIGS. 3B and 3C. Dimers can be identical or, alternatively, may be composed of more than one type of cyclic oligosaccharide. R may represent streptavidin, polymers or multimerizing agents that facilitate the organization of dimers in tandems. For example, R can be dextran, acryloyl, phenylacetylene, polyphenylene, or ethynylene poly(maleic anhydride) polyallylamine, poly(ethyleneimine) dendrimers, chitosane, and alginate, epichlorohydrin linear chains threaded on PEG (molecular tubes). Multimers are generally synthesized from cyclic oligosaccharides monomers or dimers by one of the three methods (1) radical polymerization, (2) polymer-analogous reaction, or (3) by partial crosslinking. In particular embodiments, the linker L2 may not be present and optionally L1 can be the same as R. The angle between dimers can be any. However, in some embodiments, an approximate 101° angle is preferred for it is believed to further increase the selective complexation of A2E and related bisretinoids. The binding to R can occur via one or both cyclic oligosaccharides (C), and/or through the linker L1 or L2. The dashed lines indicate that these links may or may not be present, and, if present, may be attached to any portion of the group to which they are bound. Additionally, X can be attached to C, L1, L2 and or R. X represents embedded cell-targeting sequences as described above. The representations in FIGS. 3B and 3C are meant to be non-limiting by depicting a minimum set of features that can be expanded upon in numerous ways. For example, additional embedded cyclic oligosaccharides may be included, or multiple L groups may be used to bind C cyclic units.

In some embodiments, any one or more of the above-described generic classes or specific types of cyclic oligosaccharides is excluded from the method of treatment described herein. For example, in some embodiments, cyclic oligosaccharides containing six or less ring sugar units, such as the alpha-cyclodextrins, are excluded. In other embodiments, monomethylated, dimethylated, trimethylated, or hydroxyalkylated (e.g., 2-hydroxyethylated, 2-hydroxypropylated, or 3-hydroxypropylated) cyclic oligosaccharides (e.g., cyclodextrins) are excluded. In other embodiments, charged (e.g., positively- or negatively-charged) cyclic oligosaccharides (e.g., cyclodextrins) are excluded, while in other embodiments, such charged cyclic oligosaccharides are included. In more specific embodiments, one or more of the following cyclodextrins may be excluded: trimethyl-beta-cyclodextrin, 2-hydroxyethyl-beta-cyclodextrin, 2-hydroxypropyl-beta-cyclodextrin, 3-hydroxypropyl-beta-cyclodextrin, and beta-cyclodextrin sulfobutylether sodium or potassium salt.

The cell-targeting agent (i.e., "targeting agent") is any chemical entity that has the ability to bind to (i.e., "target") a RPE cell. The cell-targeting agent may target any part of the RPE cell, e.g., cell membrane, organelle (e.g., lysosome or endosome), or cytoplasmic molecule. In one embodiment, the cell-targeting agent targets a component of a RPE cell in a selective manner. By selectively targeting a component of an RPE cell, the cell-targeting agent can, for example, selectively target certain components of cells over other types of cellular components. In other embodiments, the targeting agent targets cellular components non-selectively, e.g., by targeting cellular components found in most or all cells.

In various embodiments, the targeting agent can be, or include, for example, a peptide, dipeptide, tripeptide (e.g., glutathione), tetrapeptide, pentapeptide, hexapeptide, higher oligopeptide, protein, monosaccharide, disaccharide, trisaccharide, tetrasaccharide, higher oligosaccharide, polysaccharide (e.g., a carbohydrate), nucleobase, nucleoside (e.g., adenosine, cytidine, uridine, guanosine, thymidine, inosine, and S-Adenosyl methionine), nucleotide (i.e., mono-, di-, or tri-phosphate forms), dinucleotide, trinucleotide, tetranucleotide, higher oligonucleotide, nucleic acid, cofactor (e.g., TPP, FAD, NAD, coenzyme A, biotin, lipoamide, metal ions (e.g., Mg2+), metal-containing clusters (e.g., the iron-sulfur clusters), or a non-biological (i.e., synthetic) targeting group. Some particular types of proteins include enzymes, hormones, antibodies (e.g., monoclonal antibodies), lectins, and steroids.

Antibodies for use as targeting molecules are generally specific for one or more cell surface antigens. In a particular embodiment, the antigen is a receptor. The antibody can be a whole antibody, or alternatively, a fragment of an antibody that retains the recognition portion (i.e., hypervariable region) of the antibody. Some examples of antibody fragments include Fab, Fc, and F(ab')$_2$. In particular embodiments, particularly for the purpose of facilitating crosslinking of the antibody to the composition described herein, the antibody or antibody fragment can be chemically reduced to derivatize the antibody or antibody fragment with sulfhydryl groups.

In particular embodiments, the targeting agent is a ligand of an internalized receptor of the target cell. For example, the targeting agent can be a targeting signal for acid hydrolase precursor proteins that transport various materials to lysosomes. One such targeting agent of particular interest is mannose-6-phosphate (M6P), which is recognized by mannose 6-phosphate receptor (MPR) proteins in the trans-Golgi. Endosomes are known to be involved in transporting M6P-labeled substances to lysosomes.

In another embodiment, the targeting molecule is a peptide containing an RGD sequence, or variants thereof, that bind RGD receptors on the surface of many types of cells. Other ligands include, for example, transferrin, insulin, amylin, and the like. Receptor internalization is preferred to facilitate intracellular delivery of the inventive composition described herein.

In one set of embodiments, one cell-targeting molecule or group, or several (e.g., two, three, or more) of the same type of cell-targeting molecule or group are attached to the cyclic oligosaccharide or on a linker or pendant group thereon. In other embodiments, two or more different types of targeting molecules are attached to the cyclic oligosaccharide or on a linker or pendant group thereon. At least one possible advantage in using several cell-targeting molecules is that uptake of the cyclic oligosaccharide into RPE cells may be increased relative to use of a single cell-targeting molecule.

In some embodiments, a fluorophore may be attached to the cyclic oligosaccharide composition described above. Incorporation of one or more fluorophores can have several purposes. In some embodiments, one or more fluorophores are included in order to quantify cellular uptake and retention of the cyclic oligosaccharide composition (e.g., by a fluorescence spectroscopic method).

As used herein, a "fluorophore" refers to any species with the ability to fluoresce (i.e., that possesses a fluorescent property). For example, in one embodiment, the fluorophore is an organic fluorophore. The organic fluorophore can be, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). In the particular case of unsaturated fluorophores, the fluorophore contains one, two, three, or more carbon-carbon and/or carbon-nitrogen double and/or triple bonds. In a particular embodiment, the fluorophore contains at least two (e.g., two, three, four, five, or more) conjugated double bonds aside from any aromatic group that may be in the fluorophore. In other embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms or heteroatom-containing groups.

In other embodiments, the organic fluorophore is a xanthene derivative (e.g., fluorescein, rhodamine, Oregon green, eosin, and Texas Red), cyanine or its derivatives or subclasses (e.g., streptocyanines, hemicyanines, closed chain cyanines, phycocyanins, allophycocyanins, indocarbocyanines, oxacarbocyanines, thiacarbocyanines, merocyanins, and phthalocyanines), naphthalene derivatives (e.g., dansyl and prodan derivatives), coumarin and its derivatives, oxadiazole and its derivatives (e.g., pyridyloxazoles, nitrobenzoxadiazoles, and benzoxadiazoles), pyrene and its derivatives, oxazine and its derivatives (e.g., Nile Red, Nile Blue, and cresyl violet), acridine derivatives (e.g., proflavin, acridine orange, and acridine yellow), arylmethine derivatives (e.g., auramine, crystal violet, and malachite green), and tetrapyrrole derivatives (e.g., porphyrins and bilirubins). Some particular families of dyes considered herein are the Cy® family of dyes, the Alexa® family of dyes, the ATTO® family of dyes, and the Dy® family of dyes. The ATTO® dyes, in particular, can have several structural motifs, including, coumarin-based, rhodamine-based, carbopyronin-based, and oxazine-based structural motifs.

The fluorophore can be attached to the active portion (e.g., to the cyclic oligosaccharide, polysaccharide pendant group, a linker, or other group) by any of the linking methodologies known in the art. For example, a commercial mono-reactive fluorophore (e.g., NHS-Cy5) or bis-reactive fluorophore (e.g., bis-NHS-Cy5 or bis-maleimide-Cy5) can be used to link the fluorophore to one or more molecules containing appropriate reactive groups (e.g., amino, thiol, hydroxy, aldehydic, or ketonic groups). Alternatively, the active portion of the inventive composition can be derivatized with one, two, or more such reactive groups, and these reactive portions reacted with a fluorophore containing appropriate reactive groups (e.g., an amino-containing fluorophore).

In the method of treatment described herein, the hydrophobic (binding) cavity of the cyclic oligosaccharide must be available to complex A2E or other lipofuscin bisretinoid lipid when the cyclic oligosaccharide reaches the RPE cells. Preferably, in order to ensure this, the cyclic oligosaccharide is not complexed with a guest molecule when administered, i.e., the cyclic oligosaccharide possesses an empty hydrophobic cavity, and is thereby not functioning as a carrier when administered. In preferred embodiments, the cyclic oligosaccharide is devoid of a lipophilic compound functioning as a guest, particularly those that covalently react with RAL, or more preferably, the cyclic oligosaccharide is devoid of any guest compound altogether.

The cyclic oligosaccharide can be administered by any route that permits the cyclic oligosaccharide to contact RPE cells. The administration can be, for example, ocular, parenteral (e.g., subcutaneous, intramuscular, or intravenous), topical, transdermal, intravitreous, retro-orbital, subretinal, subscleral, oral, sublingual, or buccal modes of administration. Some of the foregoing exemplary modes of administration can be achieved by injection. However, in some embodiments, injection is avoided by use of a slow-release implant in the vicinity of the retina (e.g., subscleral route) or by administering drops to the conjuctiva.

The cyclic oligosaccharide is administered in a therapeutically-effective amount (i.e., therapeutically-effective dosage). The term "therapeutically-effective amount" or "therapeutically-effective dosage," as used herein, corresponds to an amount of active agent effective for providing any of the desired therapeutic effects described above, preferably without a substantial toxic effect to the subject.

In some embodiments, the active compound is administered, at least initially, at levels lower than that required in order to achieve a desired therapeutic effect, and the dose gradually or suddenly increased until a desired effect is achieved. In other embodiments, the active compound is administered, at least initially, at levels higher than that required in order to accelerate a desired therapeutic effect, and the dose gradually or suddenly moderated until a desired effect is achieved.

The selected dosage level will depend upon several factors, as determined by a medical practitioner. Some of these factors include the type of disease or condition being treated, the stage or severity of the condition or disease, the efficacy of the active compound being used and its bioavailability profile, as well as the specifics (e.g., genotype and phenotype) of the subject being treated, e.g., age, sex, weight, and overall condition.

Particularly for systemic modes of administration, the dosage can be, for example, in the range of about 0.01, 0.1, 0.5, 1, 5, or 10 mg per kg of body weight per day to about 20, 50, 100, 500, or 1000 mg per kilogram of body weight per day, or bi-daily, or twice, three, four, or more times a day. Particularly in embodiments where the active substance is administered non-systemically directly at the retina, the dosage can disregard body weight, and can be in smaller amounts (e.g., 1-1000 µg per dose). In some embodiments, the daily dose of the active compound is the lowest dose effective to produce a therapeutic effect. In some embodiments, the active compound is not administered in discrete dosages, but in a continuous mode, such as provided by a slow release implant or intravenous line.

Typically, in order for the cyclic oligosaccharide to be administratable to a subject, the cyclic oligosaccharide is formulated together with one or more pharmaceutically acceptable carriers (additives) and/or diluents, as well known in the art of pharmaceutical compositions. The pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) sublingually; (5) ocularly; (6) transdermally; or (7) nasally.

The phrase "pharmaceutically acceptable" is used herein to refer to those compounds, materials, compositions, and/or dosage forms that are, within the scope of sound medical judgment, suitable for entering a living organism or living biological tissue, preferably without significant toxicity, irritation, or allergic response.

The phrase "pharmaceutically-acceptable carrier," as used herein, generally refers to a pharmaceutically-acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body. Each carrier must be "acceptable" in the sense of being compatible with other ingredients of the formulation and not injurious to the patient. Examples of suitable aqueous and non-aqueous carriers that may be employed in the pharmaceutical compositions of the invention include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

Other examples of materials that can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The active agent can also be in the form of a pharmaceutically-acceptable salt. The term "pharmaceutically-acceptable salt," as used herein, refers to the relatively non-toxic, inorganic or organic addition salts of compounds of the present invention.

In one embodiment, the active agent may contain one or more basic functional groups, such as amino or alkylamino, and thereby, can form pharmaceutically-acceptable salts by reaction with a pharmaceutically-acceptable acid. These salts can be prepared in situ in the administration vehicle or the dosage form manufacturing process, or by separately reacting a purified compound of the invention in its free base form with a suitable organic or inorganic acid, and isolating the salt thus formed during subsequent purification. Some representative salts include those generated by reaction of the free base with hydrobromic, hydrochloric, sulfuric, sulfamic, bisulfuric, phosphoric, nitric, acetic, propionic, benzoic, 2-acetoxybenzoic, malic, glycolic, valeric, oleic, palmitic, stearic, lauric, benzoic, lactic, toluenesulfonic, methansulfonic, ethanedisulfonic, citric, ascorbic, maleic, oxalic, fumaric, phenylacetic, isothionic, succinic, tartaric, glutamic, salicylic, sulfanilic, napthylic, lactobionic, gluconic, laurylsulfonic acids, and the like. (Berge et al. (1977) "Pharmaceutical Salts", *J. Pharm. Sci.* 66:1-19).

In another embodiment, the active agent may contain one or more acidic functional groups, and thereby, can form pharmaceutically-acceptable salts by reaction with a pharmaceutically-acceptable base. These salts can likewise be prepared in situ in the administration vehicle or the dosage form manufacturing process, or by separately reacting the purified compound in its free acid form (e.g., hydroxyl or carboxyl) with a suitable base, and isolating the salt thus formed during subsequent purification. Some representative salts include those generated by reaction of the free acid with a metal hydroxide, metal alkoxide, ammonium hydroxide, or an amine, such as ammonia or a pharmaceutically-acceptable organic primary, secondary or tertiary amine. Some representative alkali or alkaline earth salts include lithium, sodium, potassium, calcium, magnesium, and aluminum salts. Some representative organic amines useful for the formation of base addition salts include ethylamine, diethylamine, ethylenediamine, ethanolamine, diethanolamine, piperazine and the like. (See, for example, Berge et al., supra).

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition. Some examples of pharmaceutically-acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Pharmaceutical formulations of the present invention may be prepared by any of the methods known in the pharmaceutical arts. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, the amount of active compound will be in the range of about 0.1 to 99 percent, more typically, about 5 to 70 percent, and more typically, about 10 to 30 percent.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. The active compound may also be administered as a bolus, electuary, or paste.

Methods of preparing these formulations or compositions generally include the step of admixing a compound of the present invention with the carrier, and optionally, one or more auxiliary agents. In the case of a solid dosage form (e.g., capsules, tablets, pills, powders, granules, trouches, and the like), the active compound can be admixed with a finely divided solid carrier, and typically, shaped, such as by pelletizing, tableting, granulating, powderizing, or coating. Generally, the solid carrier may include, for example, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more auxiliary ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent.

The tablets, and other solid dosage forms of the active agent, such as capsules, pills and granules, may optionally be scored or prepared with coatings and shells, such as enteric coatings and other coatings well known in the pharmaceutical-formulating art. The dosage form may also be formulated so as to provide slow or controlled release of the active ingredient therein using, for example, hydroxypropylmethyl cellulose in varying proportions to provide the desired release profile, other polymer matrices, liposomes and/or microspheres. The dosage form may alternatively be formulated for rapid release, e.g., freeze-dried.

Generally, the dosage form is required to be sterile. For this purpose, the dosage form may be sterilized by, for example, filtration through a bacteria-retaining filter, or by incorporating sterilizing agents in the form of sterile solid compositions which can be dissolved in sterile water, or some other sterile injectable medium immediately before use. The pharmaceutical compositions may also contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms are typically a pharmaceutically acceptable emulsion, microemulsion, solution, suspension, syrup, or elixir of the active agent. In addition to the active ingredient, the liquid dosage form may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Dosage forms specifically intended for topical or transdermal administration can be in the form of, for example, a powder, spray, ointment, paste, cream, lotion, gel, solution, or patch. Ophthalmic formulations, such as eye ointments, powders, solutions, and the like, are also contemplated herein. The active compound may be mixed under sterile conditions with a pharmaceutically-acceptable carrier, and with any preservatives, buffers, or propellants that may be required. The topical or transdermal dosage form may contain, in addition to an active compound of this invention, one or more excipients, such as those selected from animal and vegetable fats, oils, waxes, paraffins, starch, tragacanth, cellulose derivatives, polyethylene glycols, silicones, bentonites, silicic acid, talc and zinc oxide, and mixtures thereof. Sprays may also contain customary propellants, such as chlorofluorohydrocarbons and volatile unsubstituted hydrocarbons, such as butane and propane.

For purposes of this invention, transdermal patches may provide the advantage of permitting controlled delivery of a compound of the present invention into the body. Such dosage forms can be made by dissolving or dispersing the compound in a suitable medium. Absorption enhancers can also be included to increase the flux of the compound across the skin. The rate of such flux can be controlled by either providing a rate-controlling membrane or dispersing the compound in a polymer matrix or gel.

Pharmaceutical compositions of this invention suitable for parenteral administration generally include one or more compounds of the invention in combination with one or more pharmaceutically-acceptable sterile isotonic aqueous or nonaqueous solutions, dispersions, suspensions or emulsions, or sterile powders that may be reconstituted into sterile injectable solutions or dispersions prior to use, which may contain sugars, alcohols, antioxidants, buffers, bacteriostats, or solutes that render the formulation isotonic with the blood of the intended recipient.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms can be made by forming microencapsule matrices of the active compound in a biodegradable polymer, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions that are compatible with body tissue.

The pharmaceutical composition may also be in the form of a microemulsion. In the form of a microemulsion, bioavailability of the active agent may be improved. Reference is made to Dordunoo, S. K., et al., *Drug Development and Industrial Pharmacy*, 17(12), 1685-1713, 1991, and Sheen, P. C., et al., *J. Pharm. Sci.*, 80(7), 712-714, 1991, the contents of which are herein incorporated by reference in their entirety.

The pharmaceutical composition may also contain micelles formed from a compound of the present invention and at least one amphiphilic carrier, in which the micelles have an average diameter of less than about 100 nm. In some embodiments, the micelles have an average diameter less than about 50 nm, or an average diameter less than about 30 nm, or an average diameter less than about 20 nm.

While any suitable amphiphilic carrier is considered herein, the amphiphilic carrier is generally one that has been granted Generally-Recognized-as-Safe (GRAS) status, and that can both solubilize the compound of the present invention and microemulsify it at a later stage when the solution comes into a contact with a complex water phase (such as one found in the living biological tissue). Usually, amphiphilic ingredients that satisfy these requirements have HLB (hydrophilic to lipophilic balance) values of 2-20, and their structures contain straight chain aliphatic radicals in the range of C-6 to C-20. Some examples of amphiphilic agents include polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series). Commercially available amphiphilic carriers are particularly contemplated, including the Gelucire®-series, Labrafil®, Labrasol®, or Lauroglycol®, PEG-mono-oleate, PEG-di-oleate, PEG-mono-laurate and di-laurate, Lecithin, Polysorbate 80.

Hydrophilic polymers suitable for use in the pharmaceutical composition are generally those that are readily water-soluble, can be covalently attached to a vesicle-forming lipid, and that are tolerated in vivo without substantial toxic effects (i.e., are biocompatible). Suitable polymers include, for example, polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethylene glycol having a molecular weight of from about 100 to about 5,000 daltons, and more preferably having a molecular weight of from about 300 to about 5,000 daltons, or a molecular weight of 750 daltons, i.e., PEG(750). Polymers may also be defined by the number of monomers therein. A preferred embodiment of the present invention utilizes polymers of at least about three monomers, such PEG polymers consisting of at least three monomers, or approximately 150 daltons. Other hydrophilic polymers that may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, the pharmaceutical composition includes a biocompatible polymer selected from polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly (ortho)esters, poly(butic acid), poly(valeric acid), poly (lactide-co-caprolactone), polysaccharides, proteins, polyhyaluronic acids, polycyanoacrylates, and blends, mixtures, and copolymers thereof.

The pharmaceutical composition may also be in liposomal form. Liposomes contain at least one lipid bilayer membrane enclosing an aqueous internal compartment. Liposomes may be characterized by membrane type and by size. Small unilamellar vesicles (SUVs) have a single membrane and typically range from 0.02 to 0.05 µm in diameter; large unilamellar vesicles (LUVS) are typically larger than 0.05 µm Oligolamellar large vesicles and multilamellar vesicles have multiple, usually concentric, membrane layers, and are typically larger than 0.1 µm. The liposomes may also contain several smaller vesicles contained within a larger vesicle, i.e., multivesicular vesicles.

In some embodiments, the pharmaceutical composition includes liposomes containing a compound of the present invention, where the liposome membrane is formulated to provide an increased carrying capacity. Alternatively or in addition, the compound of the present invention may be contained within, or adsorbed onto, the liposome bilayer of the liposome. In some embodiments, the active agent may be aggregated with a lipid surfactant and carried within the liposome's internal space. In such cases, the liposome membrane is preferably formulated to resist the disruptive effects of the active agent-surfactant aggregate. In a particular embodiment, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are preferably in solubilized form. Aggregates of surfactant and active agent (such as emulsions or micelles containing the active agent of interest) may be entrapped within the interior space of liposomes according to the present invention. A surfactant typically serves to disperse and solubilize the active agent. The surfactant may be selected from any suitable aliphatic, cycloaliphatic or aromatic surfactant, including but not limited to biocompatible lysophosphatidylcholines (LPCs) of varying chain lengths, e.g., from about 14 to 20 carbons). Polymer-derivatized lipids, such as PEG-lipids, may also be utilized for micelle formation as they will act to inhibit micelle/membrane fusion, and as the addition of a polymer to surfactant molecules decreases the critical micelle concentration (CMC) of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques known in the art, such as described in, for example, U.S. Pat. No. 4,235,871 and International Published Application WO 96/14057, the contents of which are incorporated herein by reference in their entirety. For example, liposomes may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art. By another methodology, the active agent is first dispersed by sonication in a lysophosphatidylcholine or other low critical micelle concentration (CMC) surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques well known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size. The pore size of the membrane will correspond roughly with the largest sizes of liposomes produced by extrusion through the membrane (U.S. Pat. No. 4,737, 323, the contents of which are herein incorporated by reference in their entirety).

The release characteristics of a formulation of the present invention depend on several factors, including, for example, the type and thickness of the encapsulating material, the concentration of encapsulated drug, and the presence of release modifiers. If desired, the release can be manipulated to be pH dependent, such as by using a pH-sensitive coating that releases only at a low pH, as in the stomach, or releases at a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore-forming agents, which can increase water uptake or release of drug by diffusion from the capsule. Excipients that modify the solubility of the drug can also be used to control the release rate. Agents that enhance degradation of the matrix or release from the matrix can also be incorporated. The agents can be added to the drug, added as a separate phase (i.e., as particulates), or can be co-dissolved in the polymer phase depending on the compound. In all cases, the amount is preferably between 0.1 and thirty percent (w/w polymer). Some types of degradation enhancers include inorganic salts, such as ammonium sulfate and ammonium chloride; organic acids, such as citric acid, benzoic acid, and ascorbic acid; inorganic bases, such as sodium carbonate, potassium carbonate, calcium carbonate, zinc carbonate, and zinc hydroxide; organic bases, such as protamine sulfate, spermine, choline, ethanolamine, diethanolamine, and triethanolamine; and surfactants, such as a Tween™ or Pluronic™ commercial surfactant. Pore-forming agents that add microstructure to the matrices (i.e., water-soluble compounds, such as inorganic salts and sugars) are generally included as particulates.

Uptake can also be manipulated by altering residence time of the particles in the body. This can be achieved by, for example, coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

In another aspect, the invention provides an assay method for identifying a compound that binds to a lipofuscin bisretinoid lipid (e.g., A2E or derivative thereof). The method makes use of the known fluorescing ability of lipofuscin bisretinoid lipids, and the sensitivity of their fluorescing characteristics (e.g., emission wavelength) on the immediate environment. By virtue of this sensitivity, a lipofuscin bisretinoid lipid that is not bound or complexed to a particular substance (i.e., candidate compound) will show a different emission wavelength under the same conditions to the same lipofuscin bisretinoid lipid bound or complexed to the substance.

In the assay method, at least two solutions containing a lipofuscin bisretinoid lipid are first provided, and the at least two solutions should be substantially the same in all respects, such as in the type of lipofuscin bisretinoid lipid, the concentration of lipofuscin bisretinoid lipid, and the solvent composition. A candidate compound is then added to at least one of the solutions. Fluorescence spectra of the two solutions (i.e., a first solution not containing the candidate compound and a second solution containing the candidate compound) is then measured at an excitation wavelength (e.g., 434 nm or other suitable excitation wavelength) that causes fluorescence of the lipofuscin bisretinoid lipid in the range of 530 nm and 700 nm, or any suitable sub-range therein. An area under the curve (AUC) is then determined for corresponding spectral curves of the first and second solutions within the range of 530 nm and 700 nm or a sub-range therein. The corresponding spectral curves should be in the same wavelength range. A ratio of the AUC of the second solution (containing the candidate compound) over the AUC of the first solution (not containing the candidate compound) is then calculated. A ratio greater than 1 indicates that the candidate compound has bound to or complexed with the lipofuscin bisretinoid lipid, and a ratio of 1 or less indicates that the candidate compound has not bound to or complexed with (e.g., by host-guest complexation) the lipofuscin bisretinoid lipid. The candidate compound can be any compound for which lipofuscin bisretinoid lipid binding activity is to be confirmed. In particular embodiments, the candidate compound is a cyclic oligosaccharide, or more particularly, a cyclodextrin.

In some embodiments, the assay method described above is practiced in a high-throughput screening (HTS) mode. Methods and details for practicing a HTS process are well known in the art, particularly in the pharmaceutical arts, as particularly used for accelerating drug discovery. The HTS process generally employs an assay plate, typically a microtiter plate, containing a multiplicity of wells in which the assay reactions are conducted. In the HTS process, numerous reactions and measurements can be made at once, or efficiently over a short period of time. The HTS process is often automated in one or more aspects.

Other means for identifying or optimizing compounds for encapsulating or having an increased affinity for lipofuscin bisretinoid lipid (e.g., A2E) are considered herein. For example, either coupled with the fluorometric assay above or as an independent endeavor, a molecular fitting study can be undertaken to determine structural features needed to optimize encapsulation or binding affinity of A2E. This may involve molecular modeling to understand in better detail the interaction of the lipofuscin bisretinoid lipid with the hydrophobic core of the cyclic oligosaccharide. The interaction between a potential chemical host (complexant) and A2E may also be analyzed by a physical method, such as nuclear magnetic resonance spectroscopy (NMR) or microcalorimetry.

Examples have been set forth below for the purpose of illustration and to describe the best mode of the invention at the present time. However, the scope of this invention is not to be in any way limited by the examples set forth herein.

Example 1

Assay for Molecules with Ability to Encapsulate A2E

Figure 4:
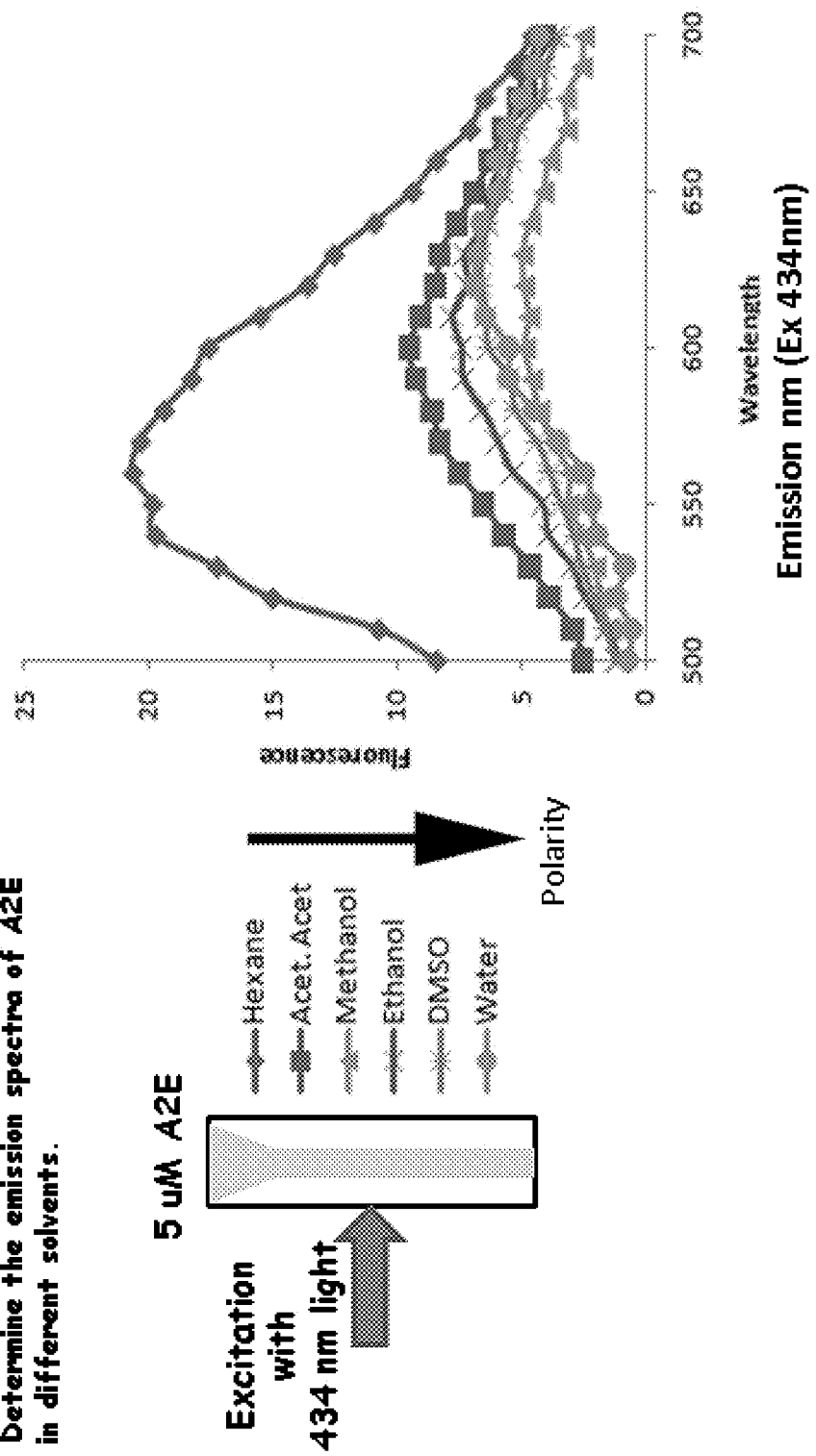
FIG. 4. Schematic showing general methodology used for measuring A2E fluorescence emission when A2E is dissolved in different solvents having different solvent polarities (left), and graph showing corresponding A2E fluorescence changes according to solvent polarity (right).

As shown in FIG. 4, A2E fluorescence changes according to the polarity of its environment. Based on this principle, a screening method was herein developed to identify molecules with the ability to encapsulate A2E.

Figure 5:
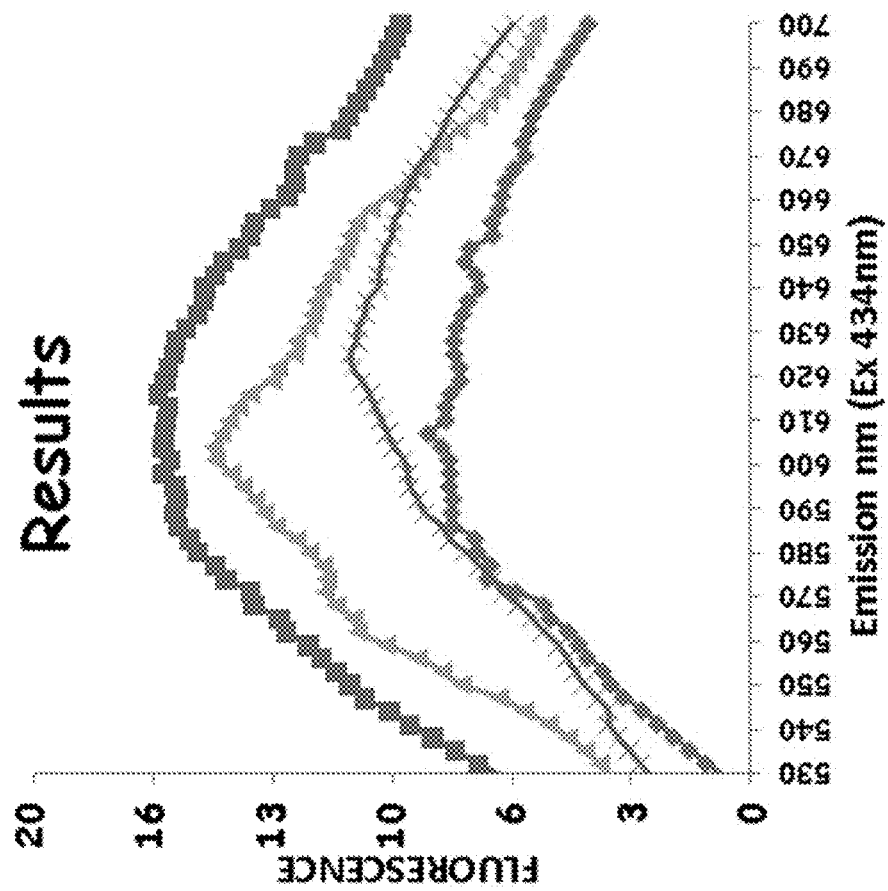
FIG. 5. Schematic showing general methodology used for measuring A2E fluorescence emission when A2E is combined with different cyclodextrins, i.e., alpha-cyclodextrin, beta-cyclodextrin, and gamma-cyclodextrin at 10 mM cyclodextrin concentrations (left), and graph (right) showing corresponding A2E fluorescence changes in the presence or absence of these cyclodextrins.
Figure 5:
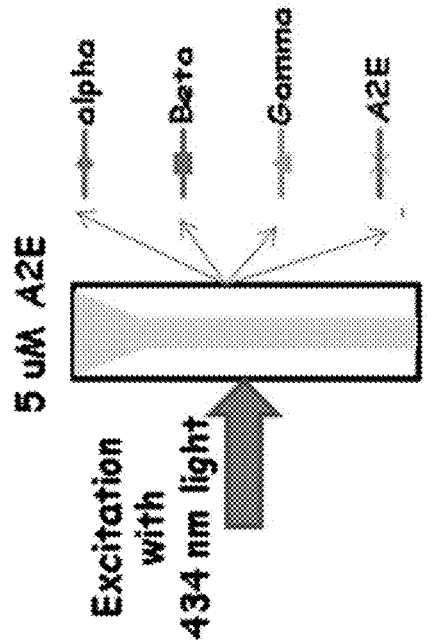

As shown in FIG. 5, A2E fluorescence changes when incubated with beta-cyclodextrins and gamma-cyclodextrins, but does not change when incubated with the alpha-cyclodextrins tested. This result indicates that the smaller interior cavity of alpha-cyclodextrins is either significantly hindered in hosting or complexing A2E or may not be capable of accommodating A2E altogether. The results also indicate that the larger cavities of beta- and gamma-cyclodextrins are much more suited for forming a host-guest complex with A2E.

As shown in FIG. 5, A2E was in a final concentration of 5 μM in 200 μl aliquots of 10 mM cyclic oligosaccharide solutions in quadruplicate. The fluorescence spectra were immediately determined (although it was stable for several days) between 530 and 700 nm using a 434 nm excitation wavelength. For inter-assay reproducibility, a sample of A2E (5 μM) in ethanol was run in each assay to normalize and compare solvatochromic shifts obtained on different days. The area under the resulting spectral fluorescence curve was determined with statistical software (Prism4, GraphPad). If the ratio of the area under the curve (AUC) for a tested compound over the AUC for A2E alone in the same aqueous phase is higher than 1, then it indicates that the cyclic oligosaccharide is encapsulating A2E. As the AUC ratios reflect the ability to form better inclusion complexes with A2E, this method easily reveals if a given compound is superior to one already developed, thus allowing identification of new active agents. No interaction will be considered when the area under the curve (AUC) is equal to 1. Based on the data collected with this method, mathematical models can be developed to determine the inclusion complex formation constants and stoichiometric constants. The assay method is valuable as a rapid screening method to characterize inclusion complexes between A2E and cyclic oligosaccharides and can be easily adapted for high-throughput screening (HTS). The method can be extended for the screening of compounds able to host or bind to other fluorescent molecules.

A library of cyclodextrins, as listed in Table 1 below, was investigated using this assay method.

TABLE 1

Library of cyclodextrin candidate compounds

| Compound # | Cyclodextrin | Structure |
|---|---|---|
| 1 | α-cyclodextrin (α-CD)<br>Sigma-Aldrich # C4680<br>Synonym: α-Schardinger dextrin, Cyclohexaamylose, Cyclomaltohexaose<br>Linear Formula: C36H60O30<br>Molecular Weight: 972.84<br>CAS Number: 10016-20-3 | (structure shown) |
| 2 | Carboxymethyl α-cyclodextrin<br>Sigma-Aldrich # ELDEXACID-kit<br>CYCLOLAB Ltd.# CY-E-1006.0 | R = H or H$_2$C(=O)OH (ratio = 19:2), n=6 |
| 3 | Carboxyethyl α-cyclodextrin<br>Sigma-Aldrich # ELDEXACID-kit<br>CYCLOLAB Ltd.# CY-E-1012.0 | R = H or H$_5$C$_2$C(=O)OH (ratio = 19:2), n=6 |
| 4 | β-cyclodextrin (β-CD)<br>Sigma-Aldrich # C4805<br>Synonym: Caraway, Cycloheptaamylose, Cyclomaltoheptaose, Schardinger β-Dextrin<br>Linear Formula: C42H70O35<br>Molecular Weight: 1134.98<br>CAS Number: 7585-39-9 | (structure shown), subscript 7 |
| 5 | Methyl-β-cyclodextrin<br>Sigma Aldrich # 332615<br>CAS Number: 128446-36-6<br>average Mn 1310 (Aldrich) | R = H or CH$_3$, subscript 7 |

TABLE 1-continued

Library of cyclodextrin candidate compounds

| Compound # | Cyclodextrin | Structure |
|---|---|---|
| 6 | Heptakis(2,3,6-tri-O-methyl)-β-cyclodextrin<br>Sigma-Aldrich # 51707<br>Synonym: 2,3,6-Tri-O-methyl-β-cyclodextrin, Trimethyl-β-cyclodextrin<br>Linear Formula: C63H112O35<br>Molecular Weight: 1429.54<br>CAS Number: 55216-11-0 | 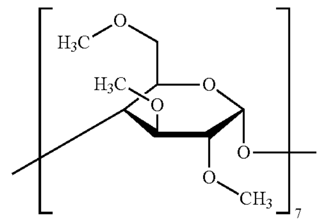 |
| 7 | (2-Hydroxypropyl)-β-cyclodextrin<br>Sigma-Aldrich 332593<br>CAS Number: 128446-35-5 | R = H or (2-hydroxypropyl) |
| 8 | Succinyl-β-cyclodextrin<br>Sigma Aldrich # 85990<br>MDL number: MFCD00800297<br>PubChem Substance ID: 24888494 | 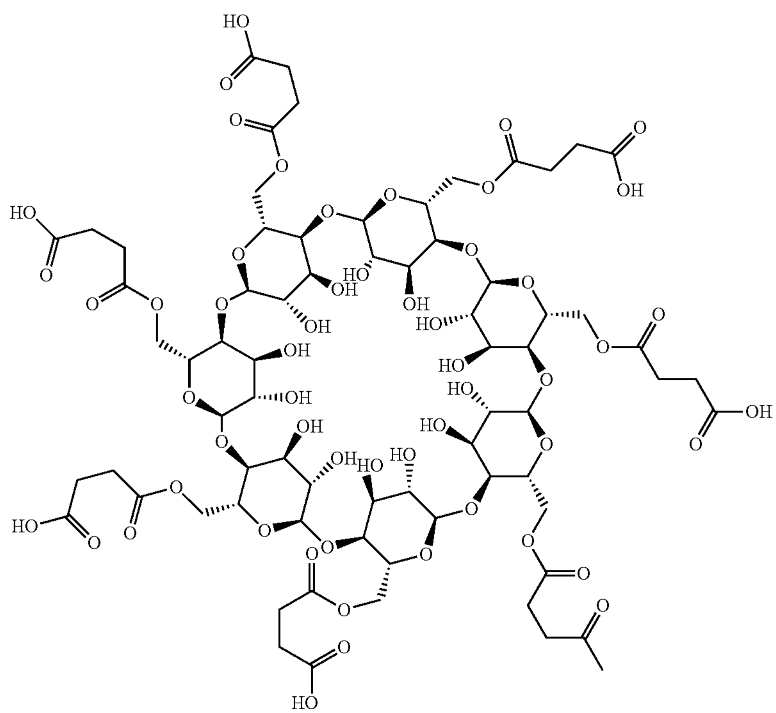 [SMILES: CC(=O)CCC(=O)OC[C@H]1O[C@@H]2O[C@H]3[C@@H](O)[C@H](O)[C@@H](O[C@H]4[C@@H](O)[C@H](O)[C@@H](O[C@H]5[C@@H](O)[C@H](O)[C@@H](O[C@H]6[C@@H](O)[C@H](O)[C@@H](O[C@H]7[C@@H](O)[C@H](O)[C@@H](O[C@H]8[C@@H](O)[C@H](O)[C@@H](O[C@H]1[C@@H](O)[C@@H]2O)O[C@@H]8COC(=O)CCC(=O)O)O[C@@H]7COC(=O)CCC(=O)O)O[C@@H]6COC(=O)CCC(=O)O)O[C@@H]5COC(=O)CCC(=O)O)O[C@@H]4COC(=O)CCC(=O)O)O[C@@H]3COC(=O)CCC(=O)O] |

TABLE 1-continued

Library of cyclodextrin candidate compounds

| Compound # | Cyclodextrin | Structure |
|---|---|---|
| 9 | β-Cyclodextrin polymer, soluble<br>Sigma Aldrich # C2485<br>Molecular wt distribution: 2,000 to 15,000 | 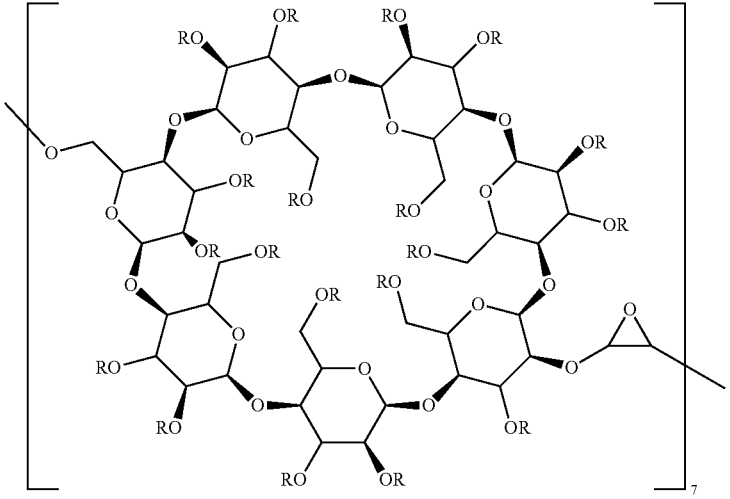 |
| 10 | Poly-beta-cyclodextrin crosslinked with epichlorohydrin TCI # P0977 | 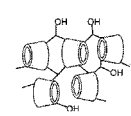 |
| 11 | Quaternary β-cyclodextrin<br>Sigma Aldrich # (Supelco) 33805 | 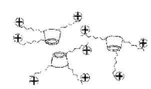 |
| 12 | Triacetyl-β-cyclodextrin<br>Sigma Aldrich # 332623<br>Synonym: β-Cyclodextrin heneicosaacetate<br>Linear Formula: C84H112O56<br>Molecular Weight: 2017.75<br>CAS Number: 23739-88-0 | 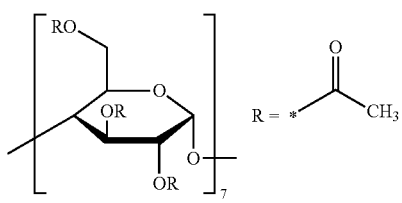 |
| 13 | 6-O-α-Maltosyl-β-cyclodextrin hydrate<br>Sigma Aldrich # M9672<br>Linear Formula: C54H90O45<br>Molecular Weight: 1459.27<br>CAS Number: 104723-60-6 | 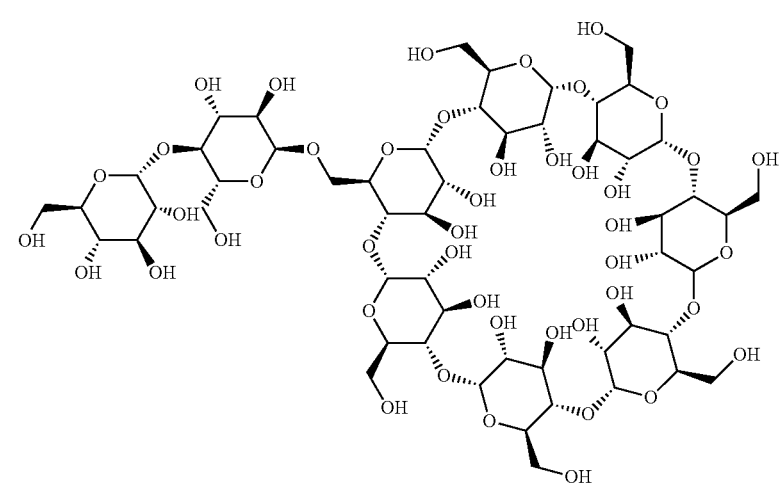 [SMILES: OC[C@H]1O[C@H](O[C@H]2[C@H](O)[C@@H](O)[C@@H](OC[C@H]3O[C@@H]4O[C@H]5[C@H](O)[C@@H](O)[C@@H](O[C@H]6[C@H](O)[C@@H](O)[C@@H](O[C@H]7[C@H](O)[C@@H](O)C(O[C@H]8[C@H](O)[C@@H](O)[C@@H](O[C@H]9[C@H](O)[C@@H](O)[C@@H](O[C@H]%10[C@H](O)[C@@H](O)[C@@H](O[C@H]3[C@H](O)[C@H]4O)O[C@@H]%10CO)O[C@@H]9CO)O[C@@H]8CO)O[C@@H]7CO)O[C@@H]6CO)O[C@@H]5CO)O[C@@H]2CO)[C@H](O)[C@@H](O)[C@@H]1O] |

TABLE 1-continued

Library of cyclodextrin candidate compounds

| Compound # | Cyclodextrin | Structure |
|---|---|---|
| 14 | Heptakis(2,6-di-O-methyl)-β-cyclodextrin<br>Sigma-Aldrich # H0513<br>Synonym: 2,6-Di-O-methyl-β-cyclodextrin, Dimethyl β-cyclodextrin<br>Linear Formula: C56H98O35<br>Molecular Weight: 1331.36<br>CAS Number: 51166-71-3 | 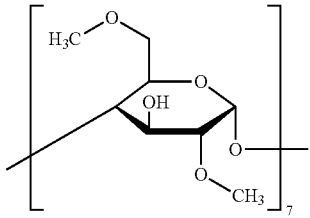 |
| 15 | Carboxymethyl-β-cyclodextrin<br>Sigma-Aldrich # ELDEXACID-Kit<br>CYCLOLAB Ltd.# CY-E-2006.0 | 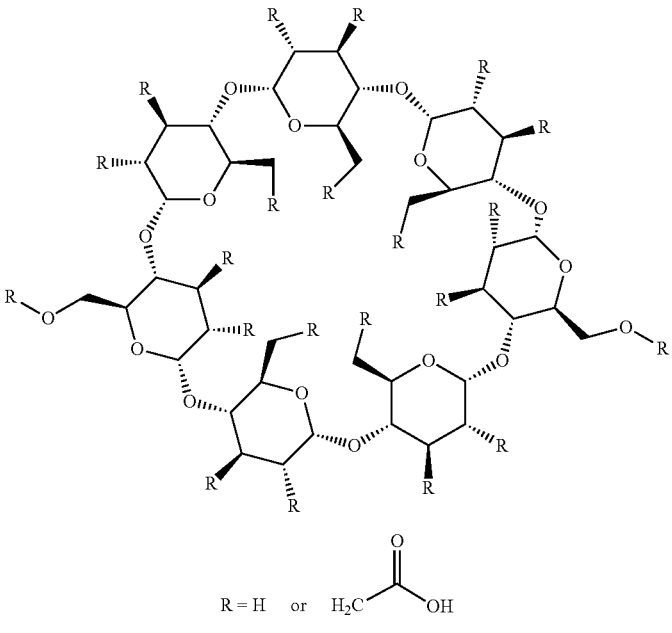<br>R = H or H$_2$C-COOH |
| 16 | Carboxyethyl β-cyclodextrin<br>Sigma-Aldrich # ELDEXACID-kit<br>CYCLOLAB Ltd.# CY-E-2012.0 | 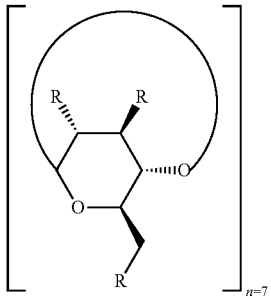<br>R = H or H$_5$C$_2$-COOH<br>(ratio = 19:2) |

TABLE 1-continued

Library of cyclodextrin candidate compounds

| Compound # | Cyclodextrin | Structure |
|---|---|---|
| 17 | γ-cyclodextrin (γ-CD)<br>Sigma-Aldrich # C4892<br>Synonym: Cyclomaltooctaose,<br>Cyclooctaamylose,<br>Schardinger γ-Dextrin<br>Linear Formula: C48H80O40<br>Molecular Weight: 1297.12<br>CAS Number: 17465-86-0 | 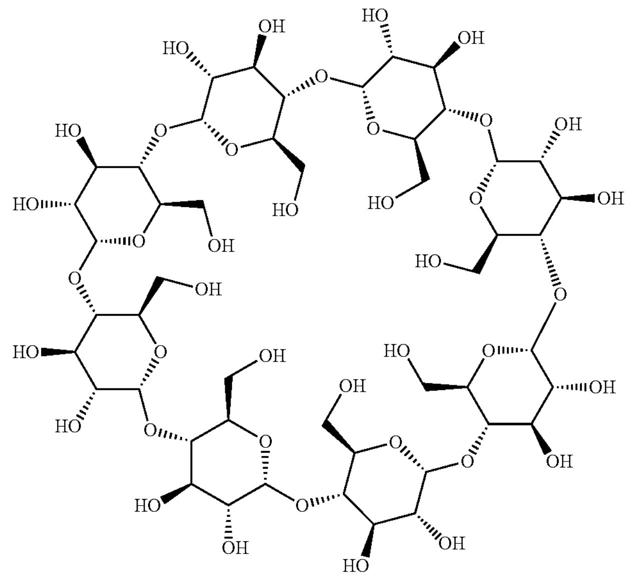 [SMILES: OC[C@H]1O[C@@H]2O[C@H]3[C@H](O)[C@@H](O)[C@@H](O[C@H]4[C@H](O)[C@@H](O)[C@@H](O[C@H]5[C@H](O)[C@@H](O)[C@@H](O[C@H]6[C@H](O)[C@@H](O)[C@@H](O[C@H]7[C@H](O)[C@@H](O)[C@@H](O[C@H]8[C@H](O)[C@@H](O)[C@@H](O[C@H]9[C@H](O)[C@@H](O)[C@@H](O[C@H]1[C@H](O)[C@H]2O)O[C@@H]9CO)O[C@@H]8CO)O[C@@H]7CO)O[C@@H]6CO)O[C@@H]5CO)O[C@@H]4CO)O[C@@H]3CO] |
| 18 | γ-Cyclodextrin polymer, soluble<br>Sigma Aldrich # C2860 | 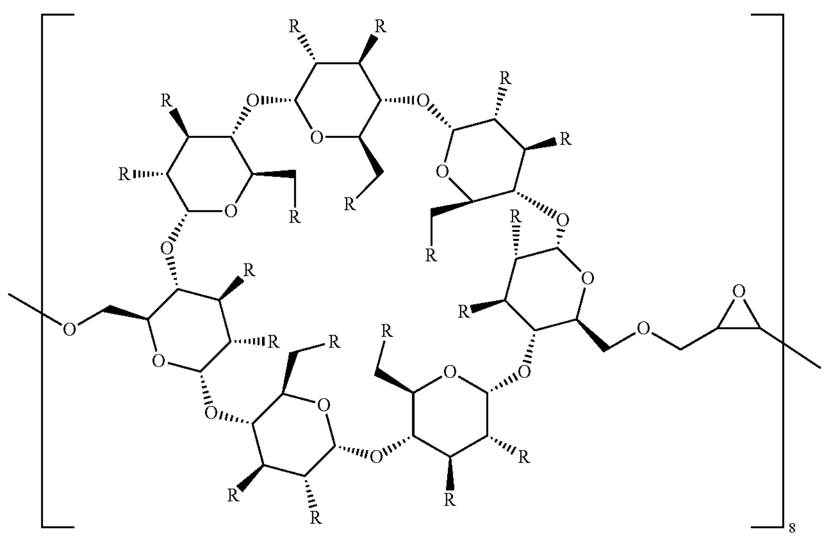 |
| 19 | γ-Cyclodextrin phosphate sodium salt<br>Sigma-Aldrich (FLUKA) # 90727<br>CAS Number: 199684-62-3 | 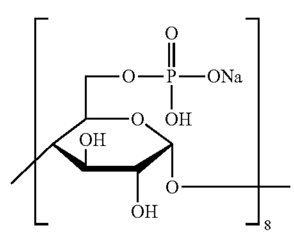 |
| 20 | (2-Hydroxypropyl)-γ-cyclodextrin<br>Sigma-Aldrich # H125<br>Synonym: HGC<br>CAS Number: 128446-34-4 | R = H or $CH_3$-containing group |

TABLE 1-continued

Library of cyclodextrin candidate compounds

| Compound # | Cyclodextrin | Structure |
|---|---|---|
| 21 | Carboxymethyl γ-cyclodextrin<br>Sigma-Aldrich #<br>ELDEXACID-kit<br>CYCLOLAB Ltd.# CY-E-3006.0 | (structure, n=8) |

Figure 6:
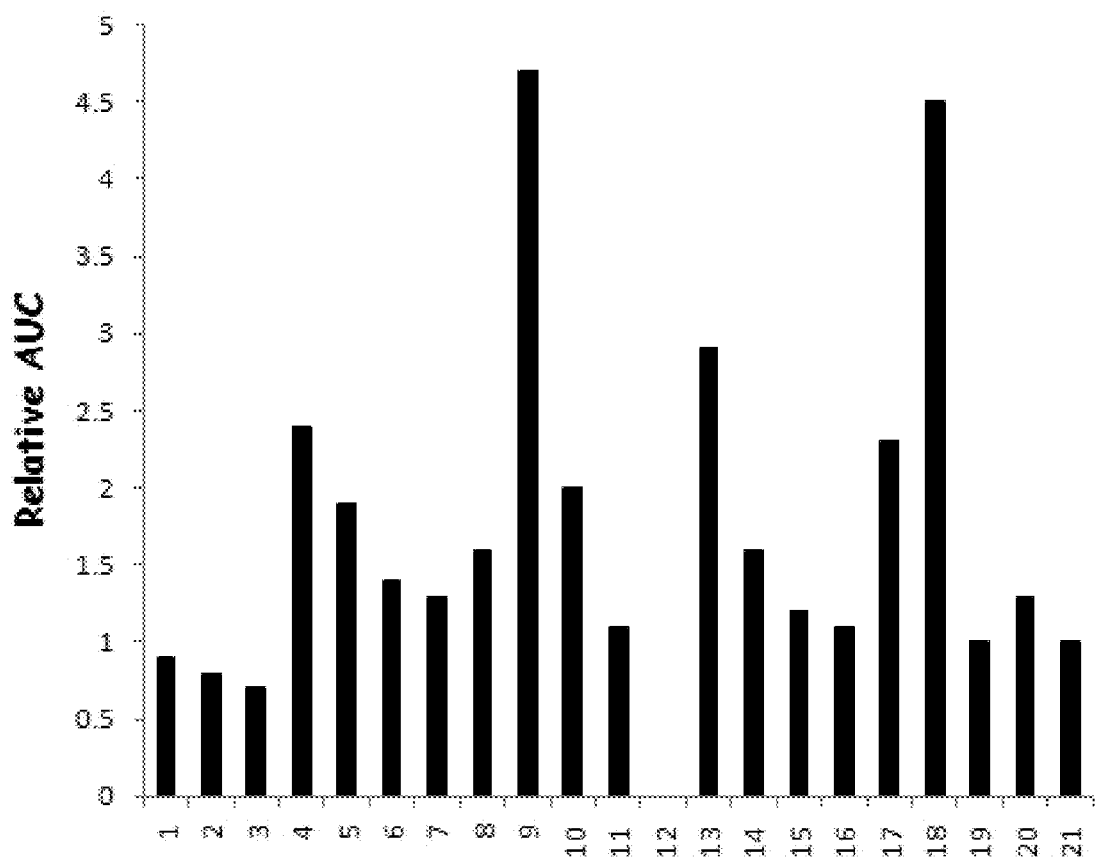
FIG. 6. Bar chart comparing the area under curve (AUC) for spectral fluorescence curves found for each of 21 cyclodextrins listed in Table 1 using the same kind of methodology outlined in FIG. 5. The numbers in the x-axis correspond to the compound numbers listed in Table 1. A relative AUC value greater than 1 indicates binding of the cyclodextrin to A2E, which is an indicator of positive efficacy of the cyclodextrin for removing A2E from RPE cells.
Figure 7A:
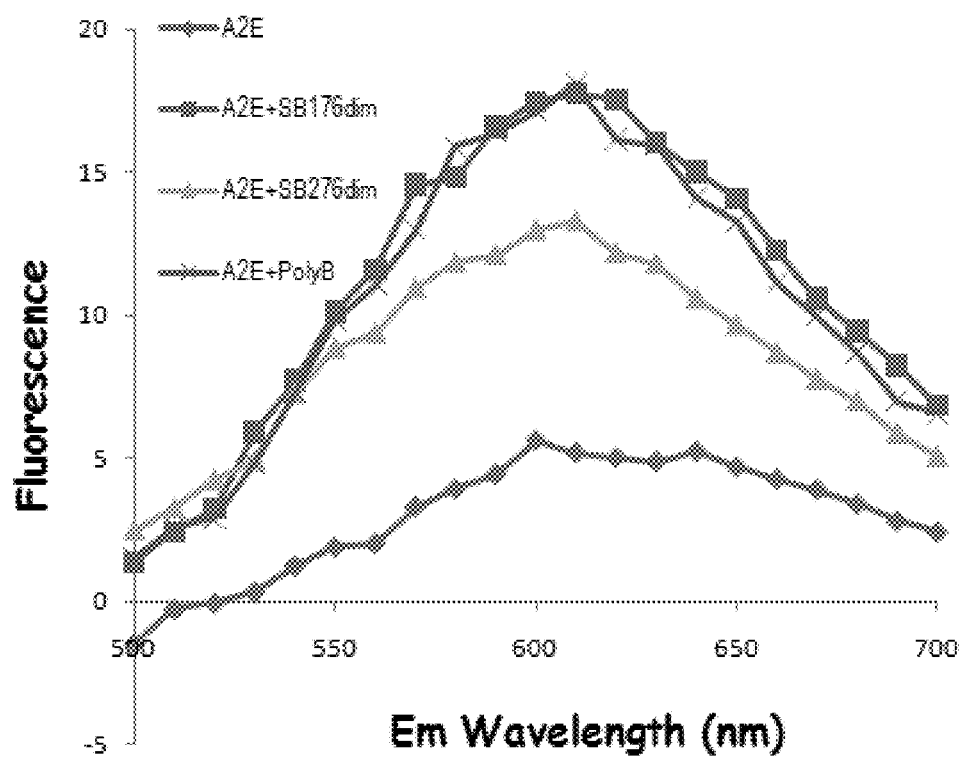
FIGS. 7A, 7B. Results for three of the leading cyclodextrins (CDs) identified to form complexes with A2E.
Figure 7A:
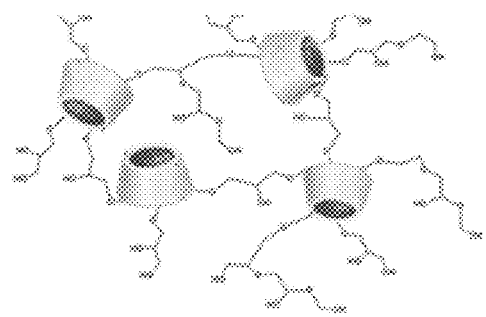
Figure 7B:
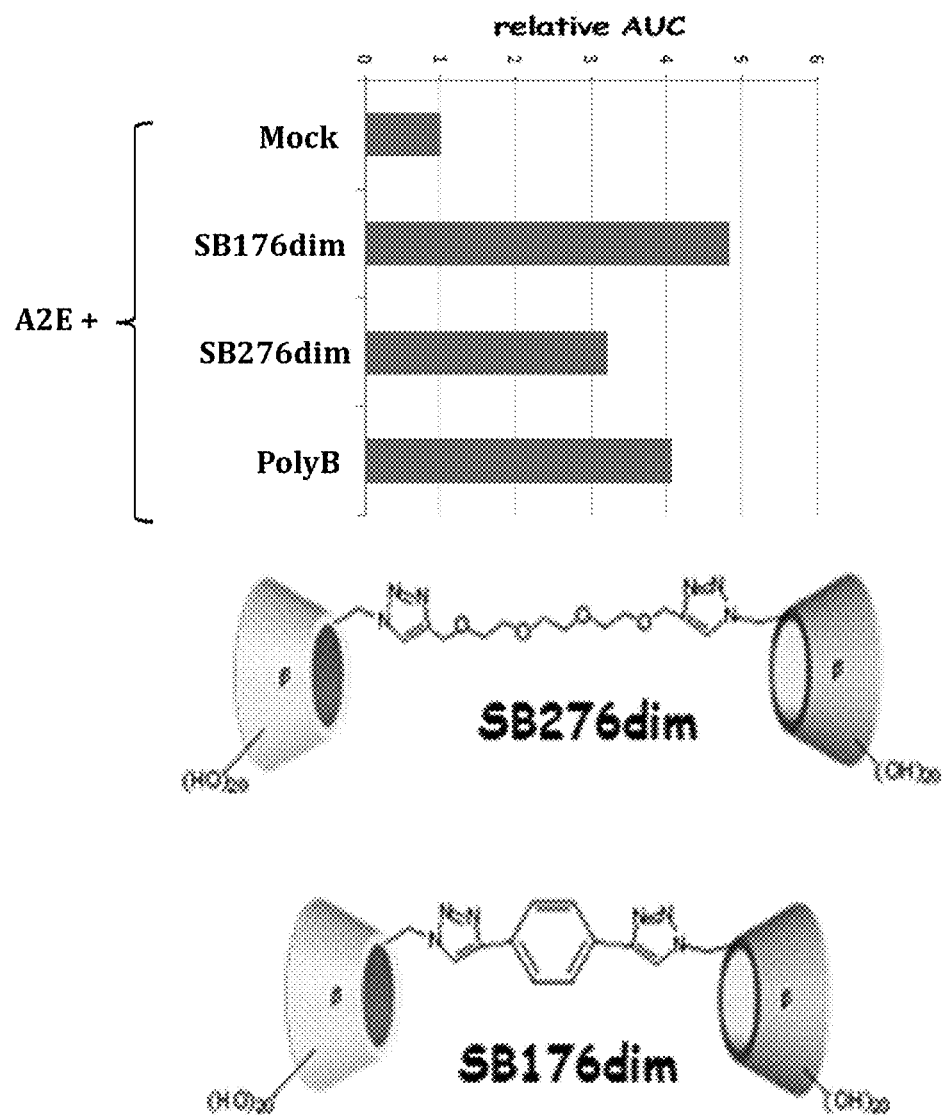
Figure 7C:
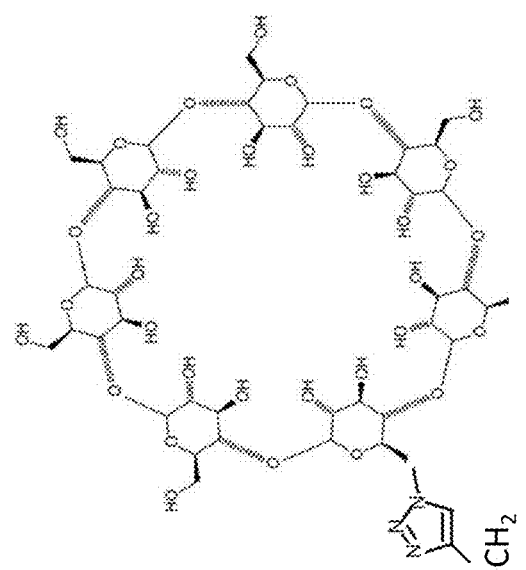
FIG. 7C: Detailed structure for CD identified as SB276dim.
Figure 7C:
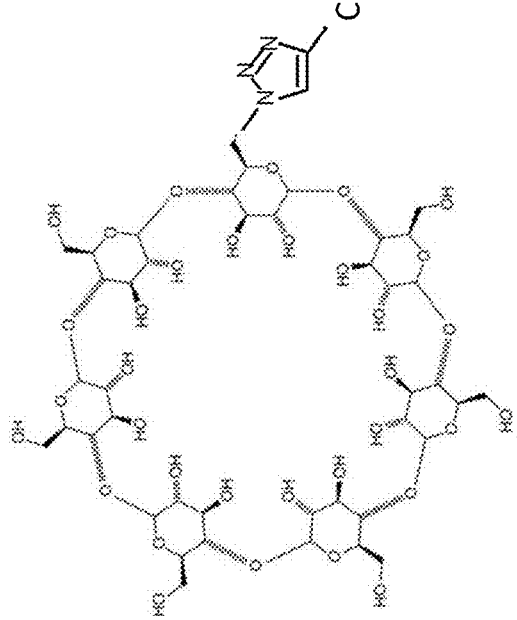
Figure 7D:
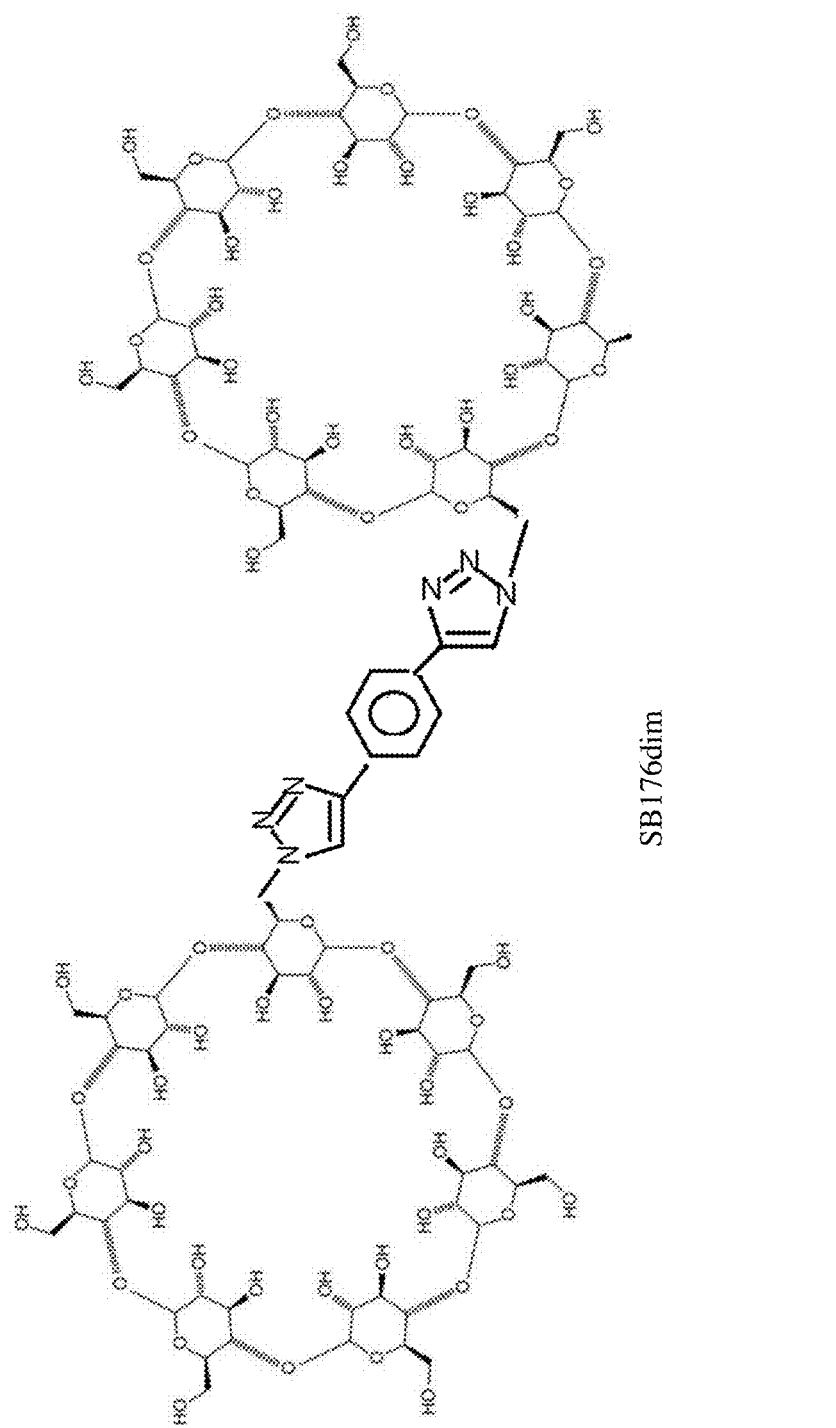
FIG. 7D: Detailed structure for CD identified as SB176dim.

FIG. 6 shows a graphical plot of the AUC calculated for each of the 21 cyclodextrin candidate compounds. The graphical plots shown in FIGS. 6 and 7 show that some of the cyclodextrins are active or highly active (i.e., by exhibiting a AUC ratio greater than 1), whereas other cyclodextrins are not sufficiently active (i.e., by exhibiting a AUC ratio of or less than 1).

Example 2

Comparison of Cyclodextrin Binding to A2E and to DHE

Figure 9A:
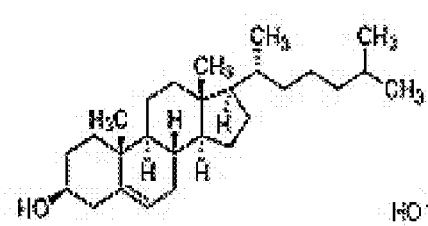
FIG. 9A. Structures of cholesterol and dehydroergosterol (DHE) (top), and fluorescence emission results of method utilized to measure the affinity of cyclodextrins for A2E as compared with results measuring the affinity of the cyclodextrins to the fluorescent cholesterol analog DHE (bottom).
Figure 9A:
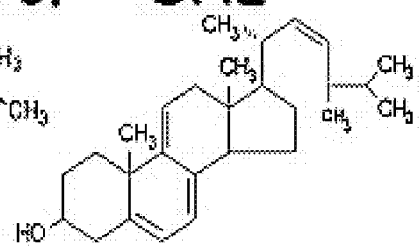
Figure 9A:
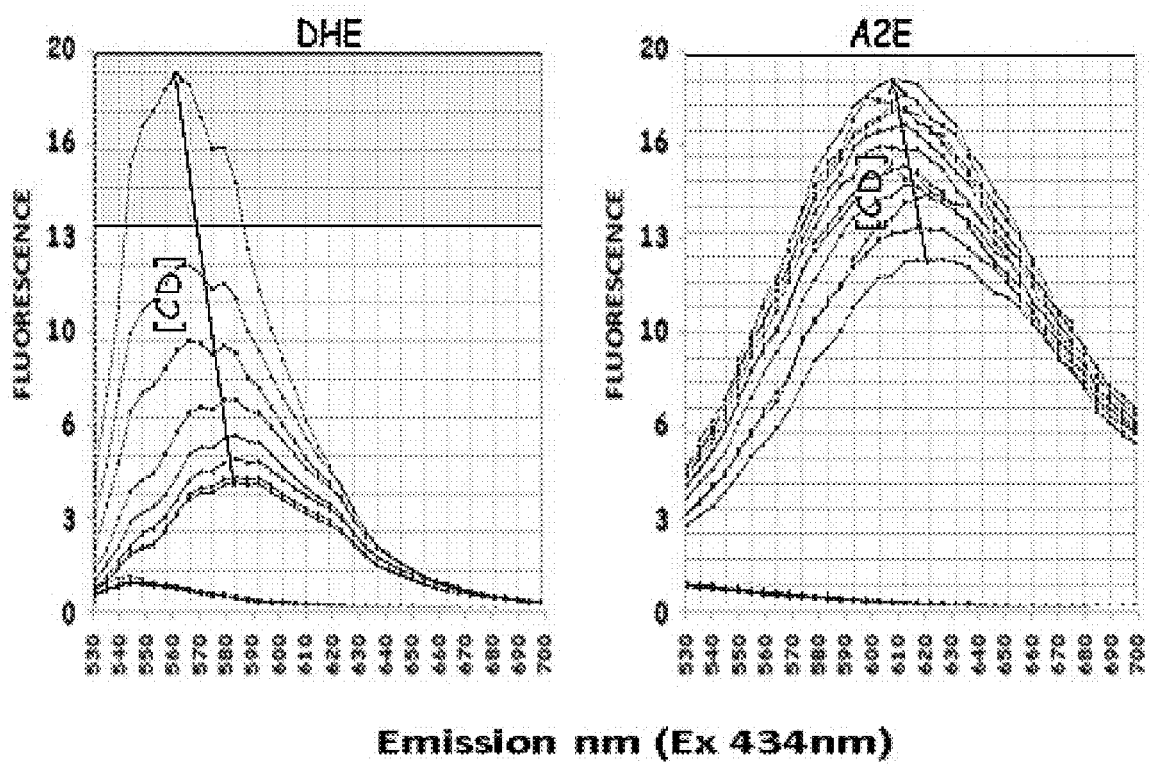
Figure 9B:
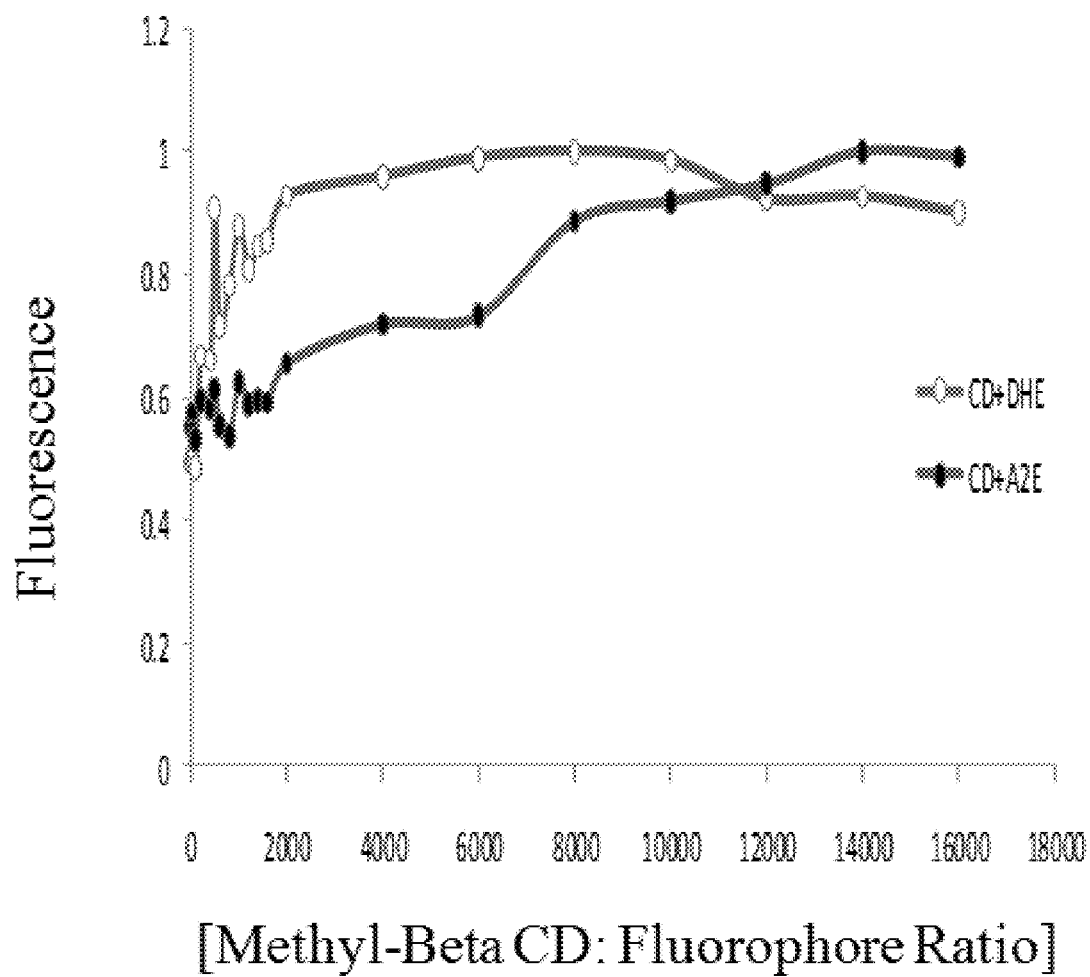
FIG. 9B. Chart plotting the fluorescence emission results of FIG. 9A as a function of CD:fluorophore ratio.

The binding of A2E and DHE (fluorescent cholesterol analog to cyclodextrins) has been herein investigated by using the assay method described above. FIG. 9A shows fluorescence spectra changes of DHE and A2E as a function of added β-CD concentration derivative. Such changes are indicative of the penetration of DHE or A2E into the hydrophobic β-CD cavities resulting in the formation of DHE-β-CD and A2E-β-CD inclusion complexes. FIG. 9B shows the fluorescence of DHE and A2E at different CD:fluorescent guest ratios. The determination of affinity constants and stoichiometry for new inclusion complexes can be complex, particularly when the molecular ratio host:guest is bigger than 1. For cholesterol, however, the affinity constants, stoichiometry, molecular structure, and applications of many of its inclusion complexes with cyclic oligosaccharides have been well established. In this context, the side-by-side comparison of A2E and cholesterol complex formation with the same cyclic oligosaccharide serves as an immediate reference to evaluate the quality of the inclusion complex with A2E, as well as help in the determination of its affinity constant, stoichiometry, and structure.

Example 3

Computer Modeling of Interaction Between Cyclodextrins and A2E

Molecular Mechanics (MM+) was used to investigate the process of inclusion of A2E into the β-CD cavity, and the stability of the inclusion complexes formed were ascertained by their energy of formation values. Theoretical studies were conducted on the parent β-CD and A2E only. In the study, it was assumed that the basic closed structure of β-CD is maintained in A2E-CD. Schroedinger Suite™ was used to build the structure of A2E and β-CD molecules. A2E β-CD was built on-screen using molecular design software/Pymol, and β-CD monomer was downloaded as PDB coordinates. The structures of A2E-β-CD complexes were considered in the gaseous state and the molecular mechanics program MM+ implemented in the software package was used to minimize them. No cut-offs were used and geometry optimization was made to an energy convergence of 0.01 kcal/A per mol with the Polak-Ribiere conjugate gradient algorithm.

Docking calculations were performed in vacuo to locate the low energy structures for the A2E-β-CD complexes. Two principal relative arrangements of A2E and β-CD were considered. In one case, the A2E molecule was allowed to approach the β-CD cavity from the wider rim, which contains the secondary hydroxyl groups, while in the other, it was made to approach the β-CD cavity from the primary hydroxyl rim. The initial A2E configuration was parallel to the β-CD hydroxyl rim at a distance of about 2 Å from the rim. A2E was then manually rotated by steps of 45° and an optimization was set to start after each rotation. Each of these stochastically-generated low-energy structures were then grouped so as to identify the path of entry of A2E into the β-CD cavity and the nature of complex formed with β-CD. This work provides the basis for a preferred embodiment in which the cyclic oligosaccharide is multimeric.

Example 4

A2E Oxidation Assay

Figure 12A:
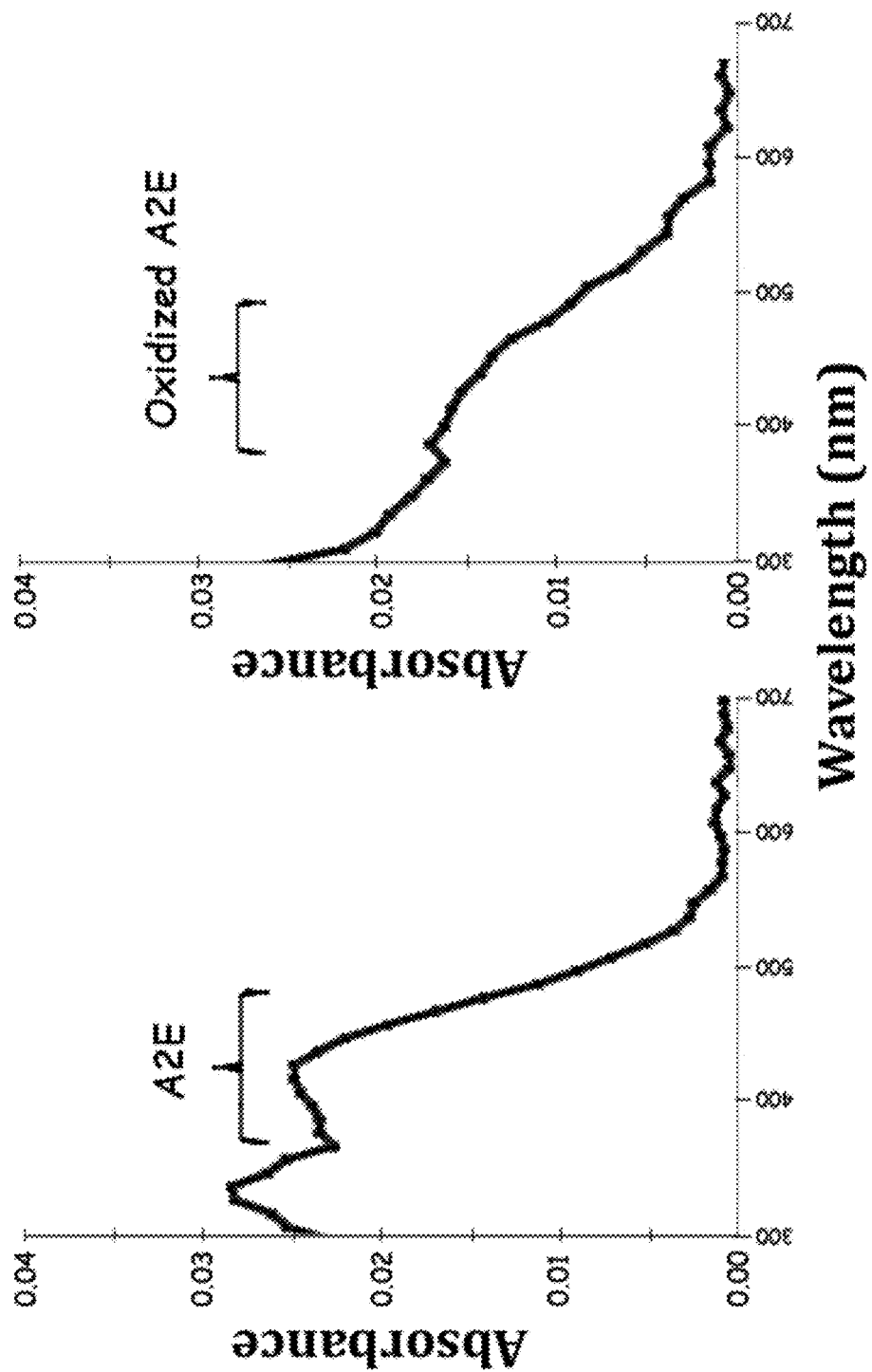
FIGS. 12A, 12B. Absorption spectra of normal and oxidized A2E (FIG. 12A), and absorption spectra of A2E under oxidizing conditions in the presence or absence of beta-cyclodextrin (FIG. 12B).
Figure 12B:
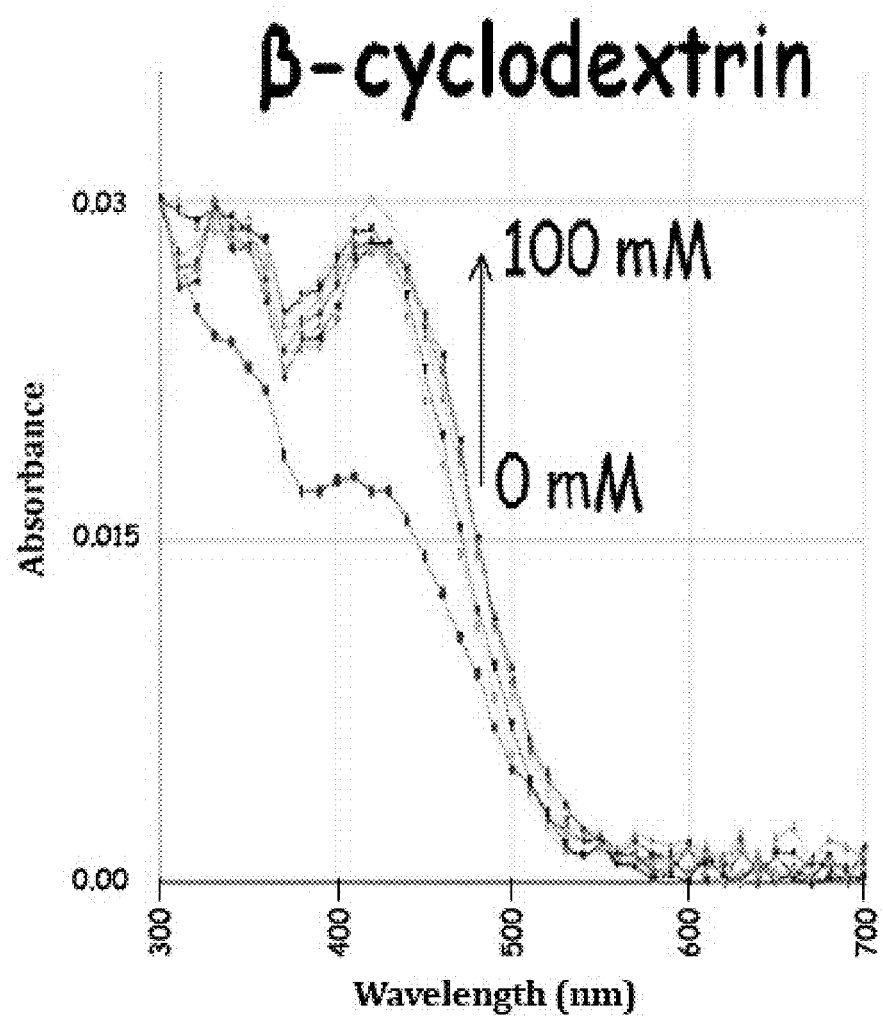
Figure 13A:
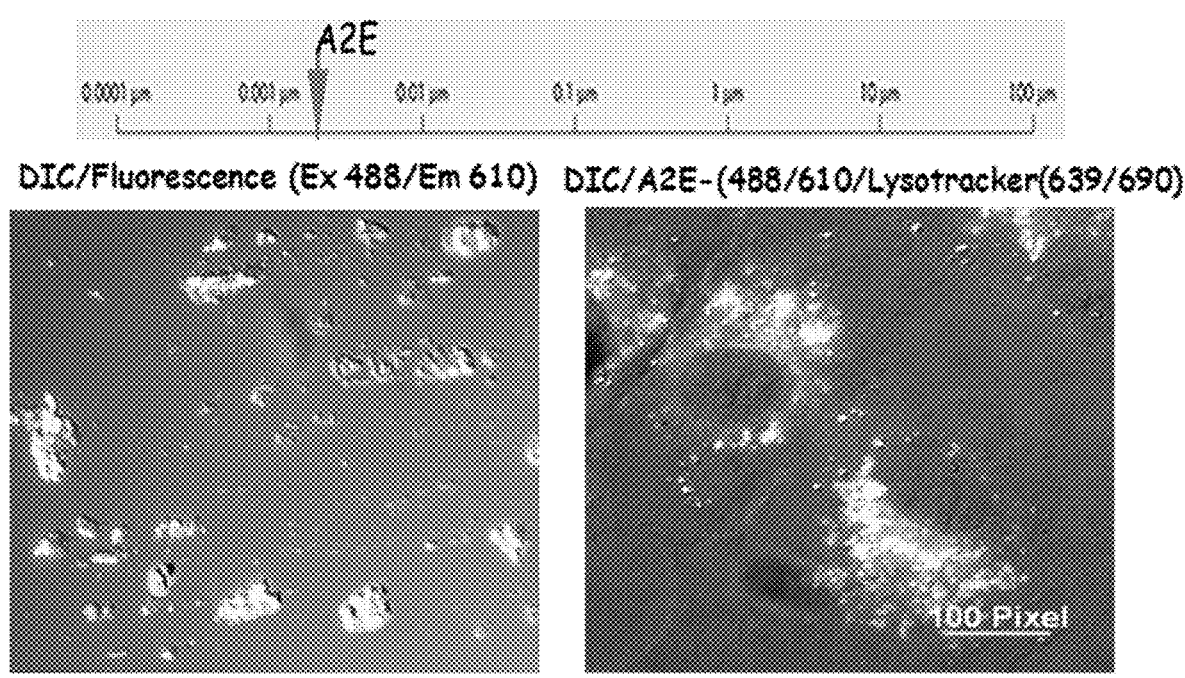
FIGS. 13A-13C. Results showing that cyclic oligosaccharides dissolve A2E aggregates that form in aqueous phase.
Figure 13B:
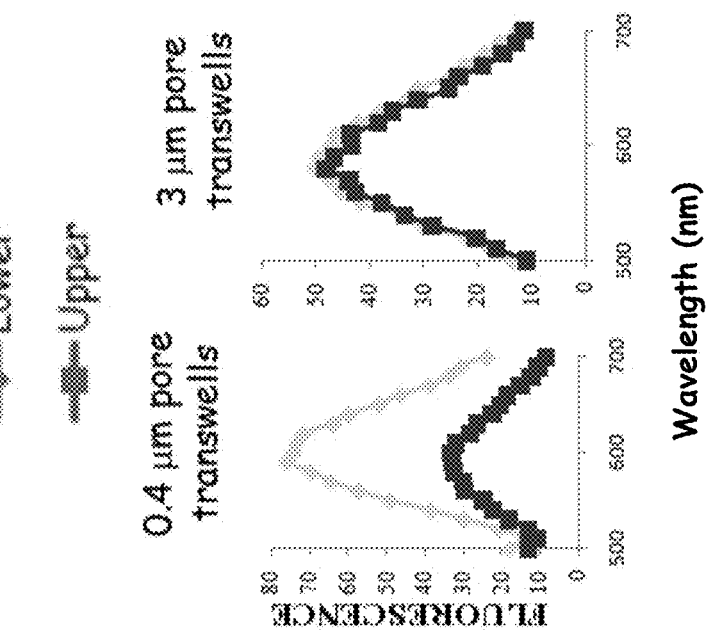
Figure 13B:
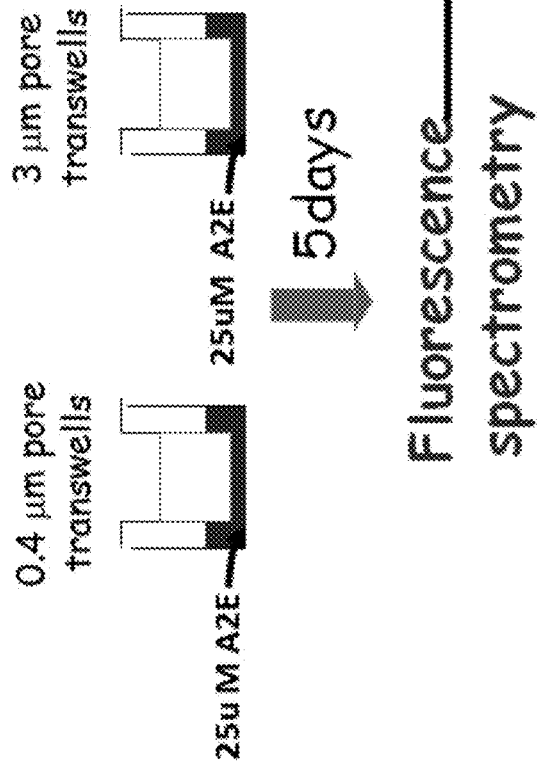
Figure 13C:
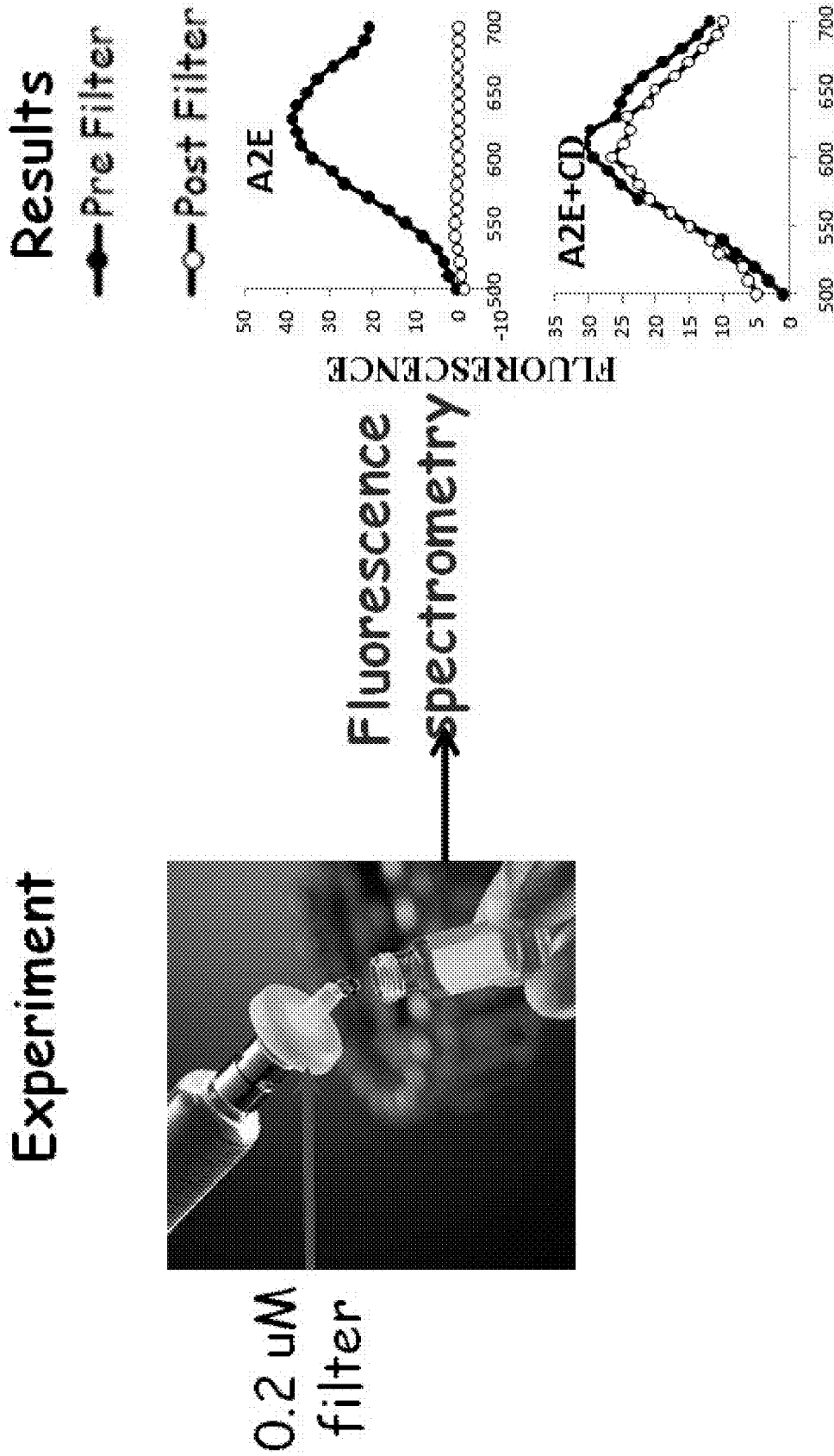

Solutions containing increasing amounts of Poly Beta-CD (0 mM to 100 mM) were prepared in water, and A2E was added to a final concentration of 5 μM. The solutions were incubated at RT in the dark. 48 hrs later, the UV-visible absorption spectra between 300 and 700 nm was analyzed to determine the oxidative status of A2E. The UV-visible spectrum of A2E exhibits two major absorbance bands at 337 nm and 438 nm. These bands can be assigned to the shorter (S) and longer (L) arms of A2E, respectively. Oxidation of a carbon-carbon double bond is accompanied by a hypsochromic shift. A hypsochromic shift in band S corresponds with oxidation on the short arm; a blue-shift in band L reflects oxidation on the long arm; hypsochromic shifts in both peaks indicates oxidation on both side arms (Jang Y. P. et al., *J. Biol. Chem.*, 2005, 280(48):39732-9). The results shown in FIG. 12A indicate that under this aqueous environment A2E oxidizes. However, the results shown in FIG. 12B also demonstrate that the formation of the inclusion complex with CDs protect against this event.

Example 5

A2E Aggregation Assay

A2E aggregates are believed to have a role in RPE cell death. This study investigated whether cyclic oligosaccharides dissolve A2E aggregates that form in aqueous phase. The following can be deduced from FIG. 13:

A) Predicted size (<0.005 um) of A2E molecule based on its molecular weight (596).

B) Differential Interference Contrast (DIC) microscopy, combined with fluorescence microscopy, shows that A2E aggregates to form crystals of several microns in size when in aqueous phase, both in cell free and (left panel) and within RPE cells (right panel). A2E was added to the cells at 25 µM final concentration for three days.

C) Transwell with 0.4 µm and 3 µm pores were inserted in 12-well plates, and A2E was added to the media in only one side of the membrane. After three days, the liquid in each chamber was harvested and analyzed with a spectrofluorometer to detect the presence of A2E. Only inserts with 3 µm pores allowed A2E to diffuse through.

D) Using similar principles, it was demonstrated that A2E in 25 µM aqueous solutions cannot pass through 0.2 µm pore filters. In contrast, addition of cyclodextrins to the A2E aqueous solution dissolved the A2E aggregates, thereby allowing A2E to diffuse through 0.2 µm pores. The presence of A2E on each side was established by fluorescence scanning between 530-700 nm using 434 nm as the excitation wavelength.

Example 6

Cell Assay of Cyclodextrin Efficacy

Figures 14A, 14B, 14C, 14D:
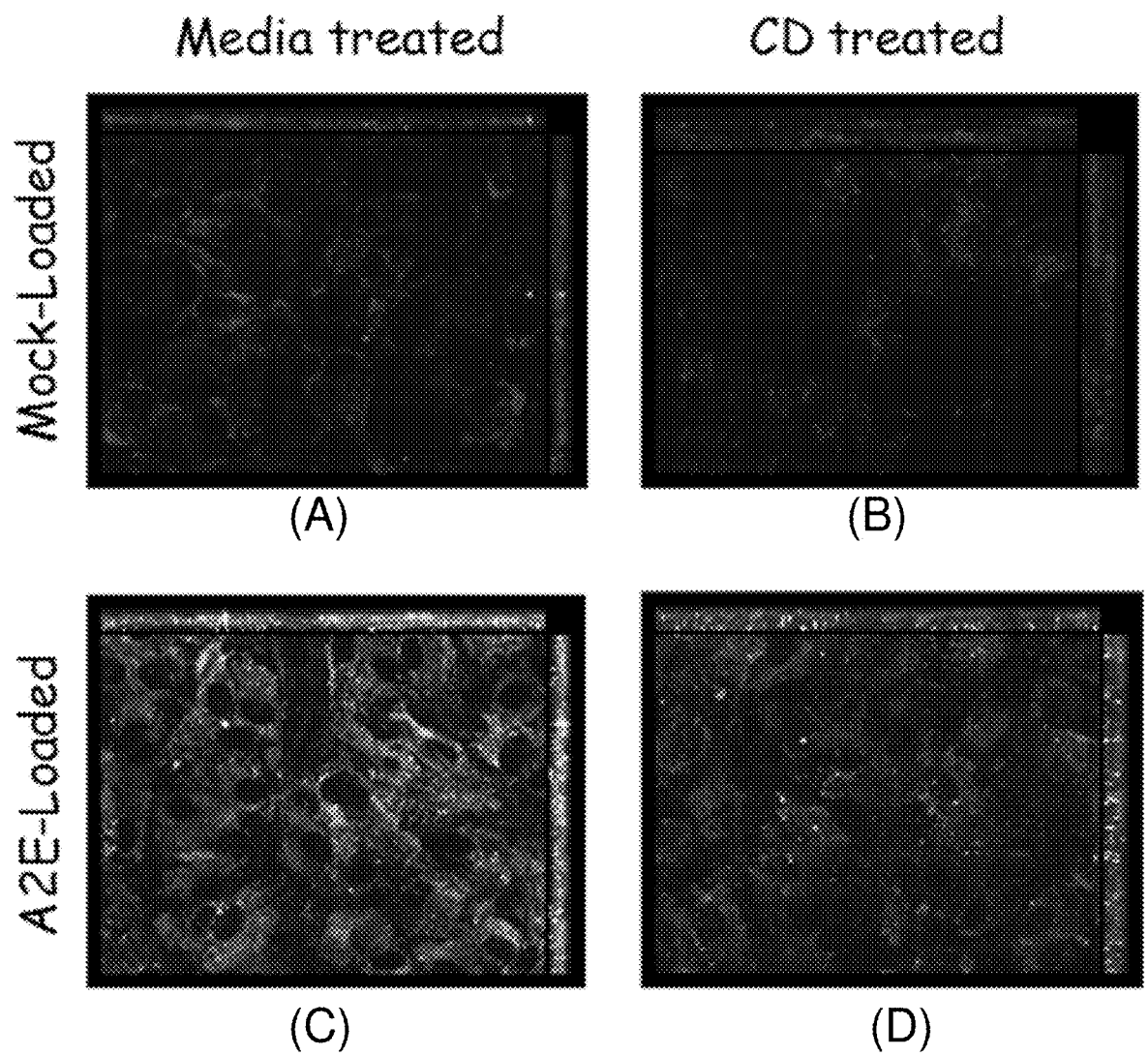
FIGS. 14A-14D. Micrographs showing that multimeric beta-cyclodextrins can reduce the levels of A2E in RPE cells. ARPE-19 cells were loaded with A2E for 48 hrs, and washed and treated with 1 mM cyclodextrin for 72 hours. A2E fluorescence was pictured in an spinning disk microscope using adequate filter sets. Micrographs for mock-loaded and media-treated (FIG. 14A), mock-loaded and CD-treated (FIG. 14B), A2E-loaded and media-treated (FIG. 14C), and A2E-loaded and CD-treated (FIG. 14D).
Figure 15A:
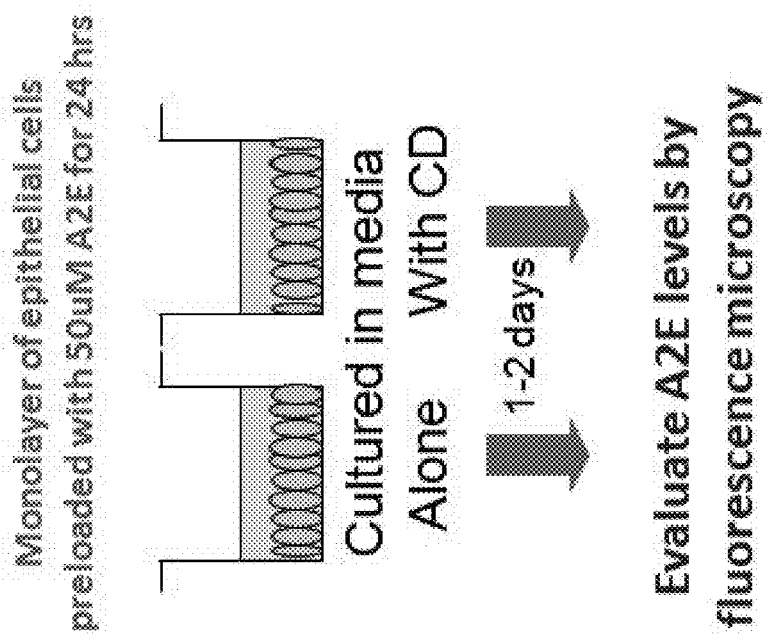
FIGS. 15A, 15B. CDs can reduce A2E levels in highly confluent, well polarized, epithelia.

The aim of this study was to determine whether cyclic oligosaccharides clear RPE cells from bisretinoids by encapsulating A2E. Briefly, ARPE-19 cells, a human retinal-pigmented epithelial cell line, were grown in media containing A2E (25 µM final) for three days. Subsequently, the cells were washed twice and incubated for three days in media containing 1 mM poly BetaCD and 10% FMS. After three more days, the content of A2E was compared by microscopy between A2E-loaded cells, treated and non-treated with cyclodextrin (CD). As shown in FIGS. 14 and 15, administration of cyclic oligosaccharides causes a significant reduction in bisretinoids RPE cell content.

Figure 15B:
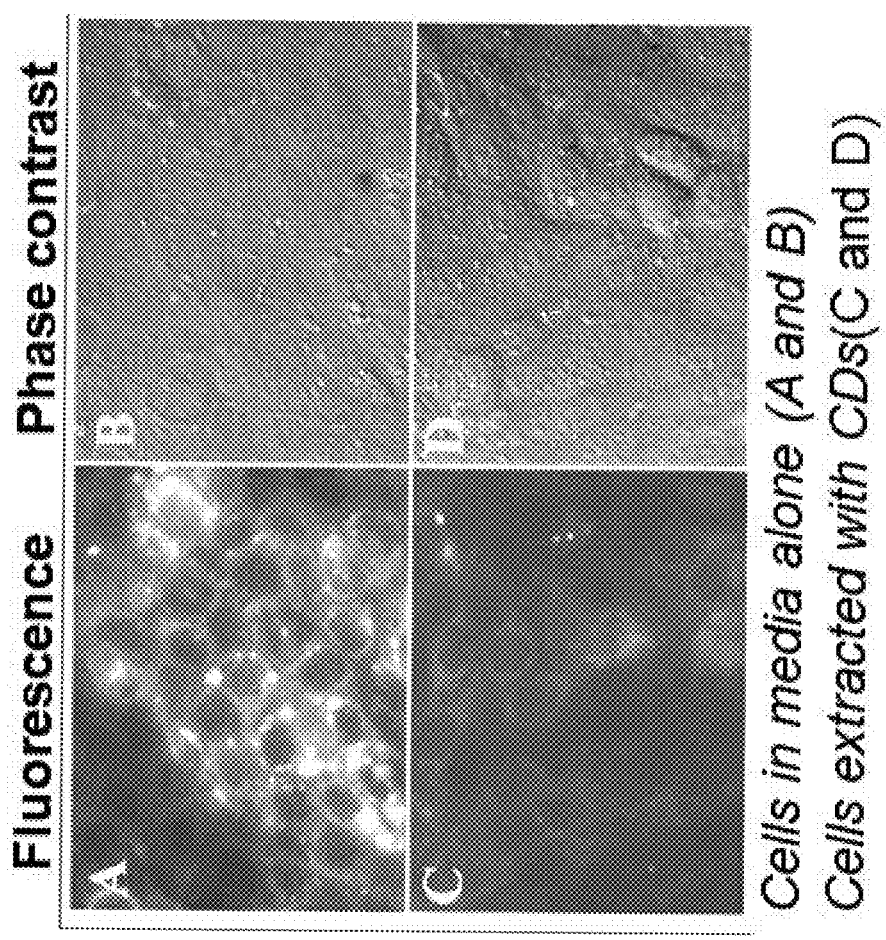

FIG. 15 shows that CDs can reduce A2E levels in highly confluent, well polarized, epithelia. In FIG. 15B, Panel A shows control epithelial cells loaded with A2E (bright fluorescence). Panel C shows polarized epithelium extracted with CDs after 24 hours. The loss of fluorescent pigments is notable. Panels B and D are images of the same epithelia illuminated with white light to demonstrate that their integrity is not compromised by treatment with CDs.

An excellent animal model to study retinal degeneration in response to accumulation of bisretinoids is the recently developed RDH8/ABCA4-double knockout (DKO) mice, which exhibit accelerated A2E build up and display progressive retinal degeneration and blindness, with typical signs of AMD such as "drusen" and thickened Bruch's membrane, by five weeks (Maeda, A., et al., *Retinopathy in mice induced by disrupted all-trans-retinal clearance*. J Biol Chem, 2008. 283(39): p. 26684-93).

Example 7

Figure 17A:
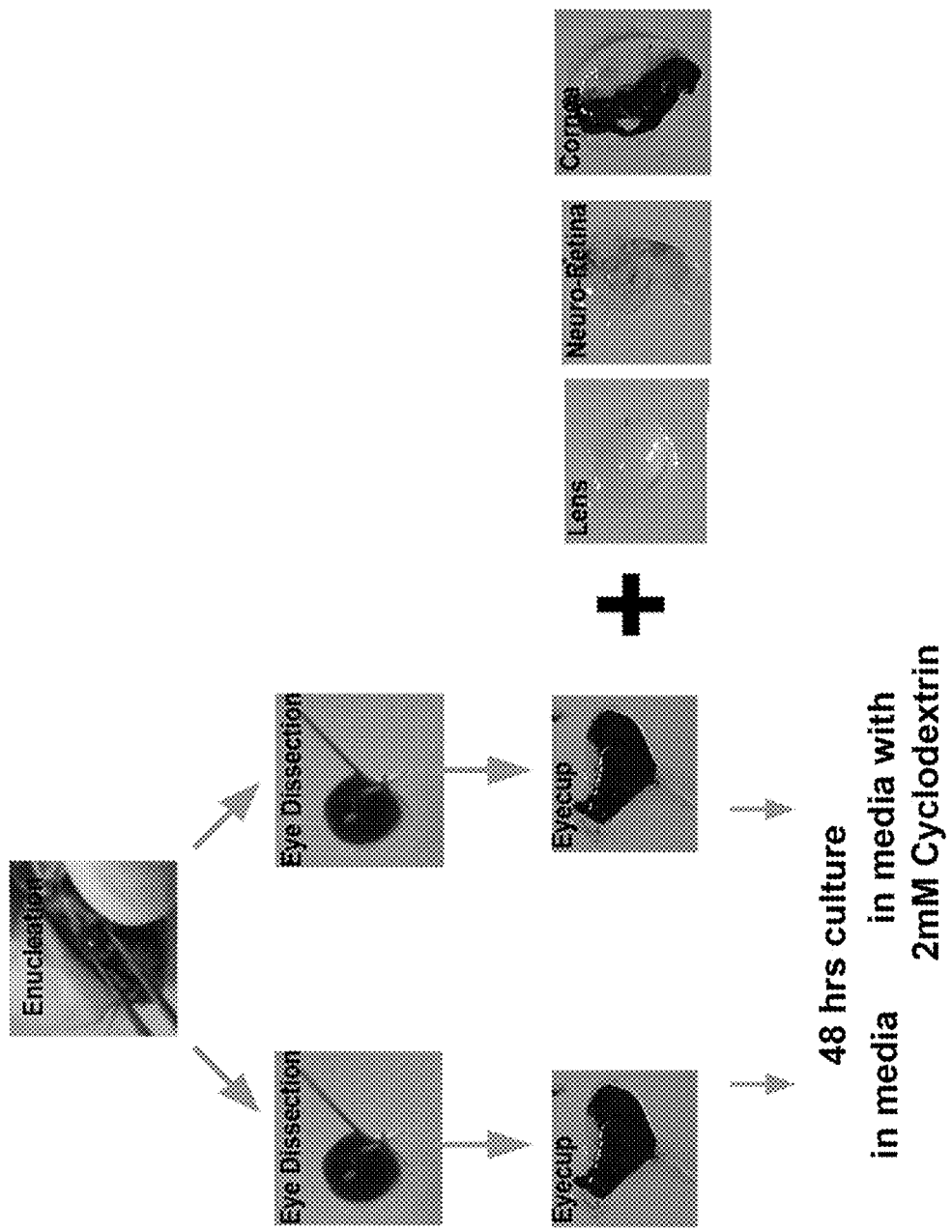
FIGS. 17A, 17B.
Figure 17B:
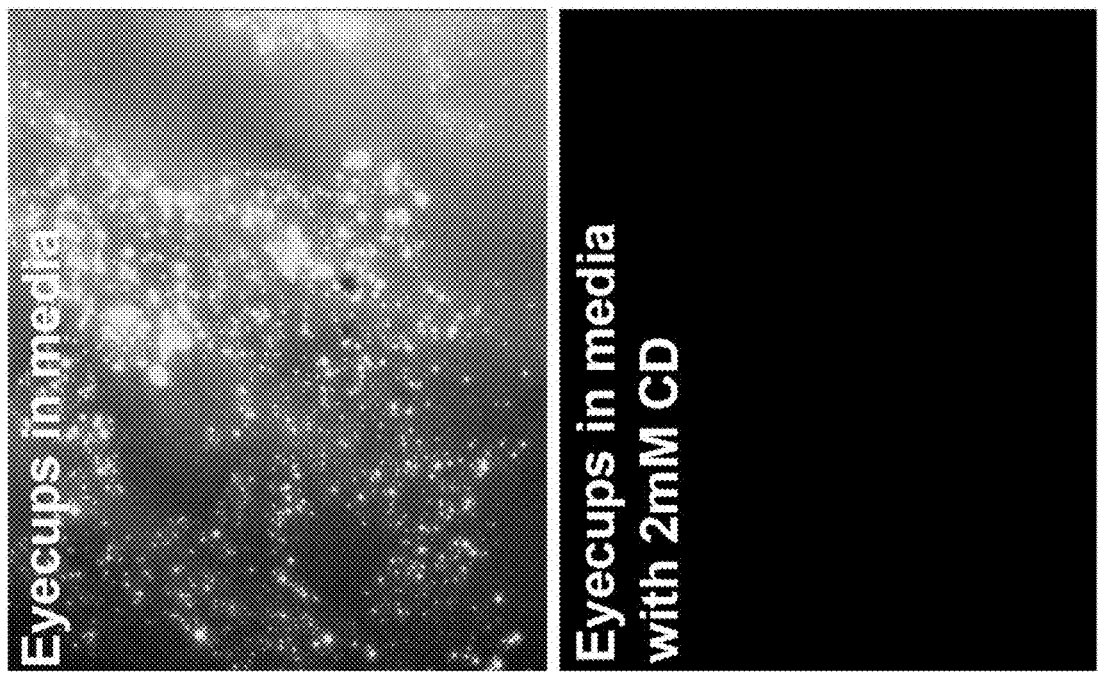

"In Vitro" Assay Showing that Cyclodextrins Effectively Clean Bisretinoids from the Eye of DKO Mice As indicated in FIG. 17A, eyes from DKO mice were enucleated and dissected to separate cornea, lens, iris and neuroretina from the posterior part of the eye (eyecups). Eyecups comprise the dark pigmented RPE, choriocapillaries, as well as the grayish sclera. Eyecups were incubated in complete media containing, or not, 2 mM cyclodextrins. After 36 hours of culture, eyecups were flat mounted on glasses and fluorescence was analyzed in the microscope. The lack of fluorescence in eyecups incubated with methyl beta-cyclodextrin is indicative of the ability of CDs to remove bisretinoids from the eye's RPE.

A fundus camera or retinal camera is a specialized low power microscope with an attached camera designed to photograph the interior surface of the eye, including the retina, optic disc, macula, and posterior pole (i.e. the fundus). Fundus cameras are used by optometrists, ophthalmologists, and trained medical professionals for monitoring progression or diagnosis of a retinal disease. A typical camera views 30 to 50 degrees of retinal area, with a magnification of 2.5×.

Color fundus examination is performed when the retina is illuminated by white light and the resulting image is consequently full colored. It permits detection of the extracellular deposits, called drusen, underneath the RPE that are among the earliest signs of retinal dysfunction.

Autofluorescence fundus is performed when the retina is illuminated by blue light of about 430 nm. The intensity of the resulting green fluorescence permits semi-quantitative assessment of the amount of bisretinoids accumulated in the RPE of the eye.

Figure 16A:
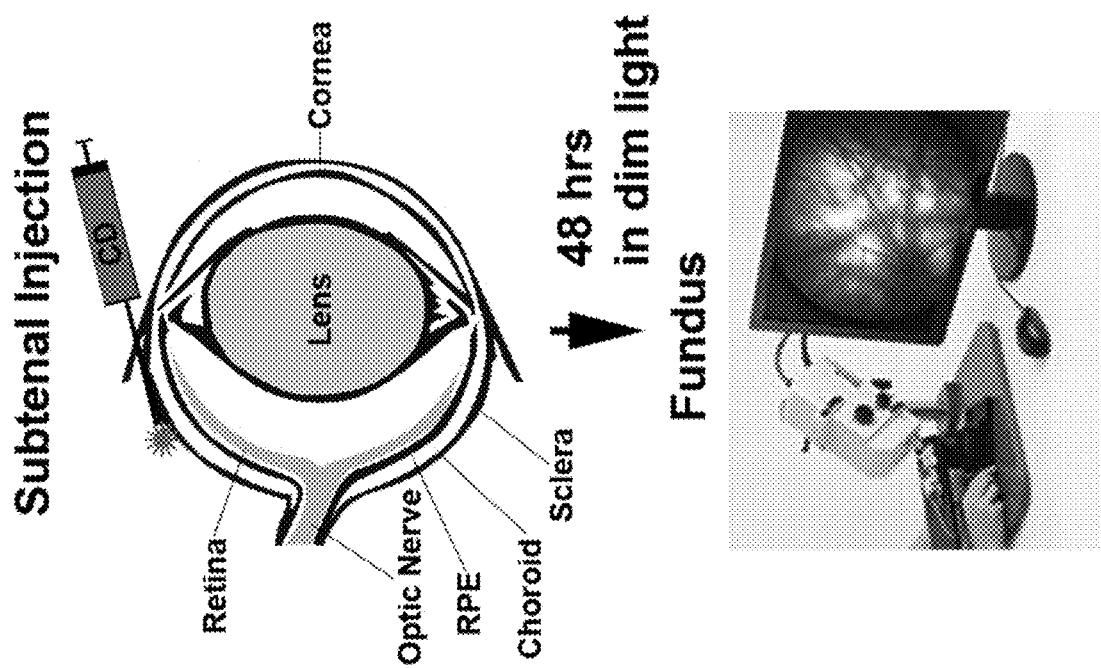
FIGS. 16A, 16B. CD-treatment of DKO mice reduces fundus, drusen and autofluorescence.
Figure 16B:
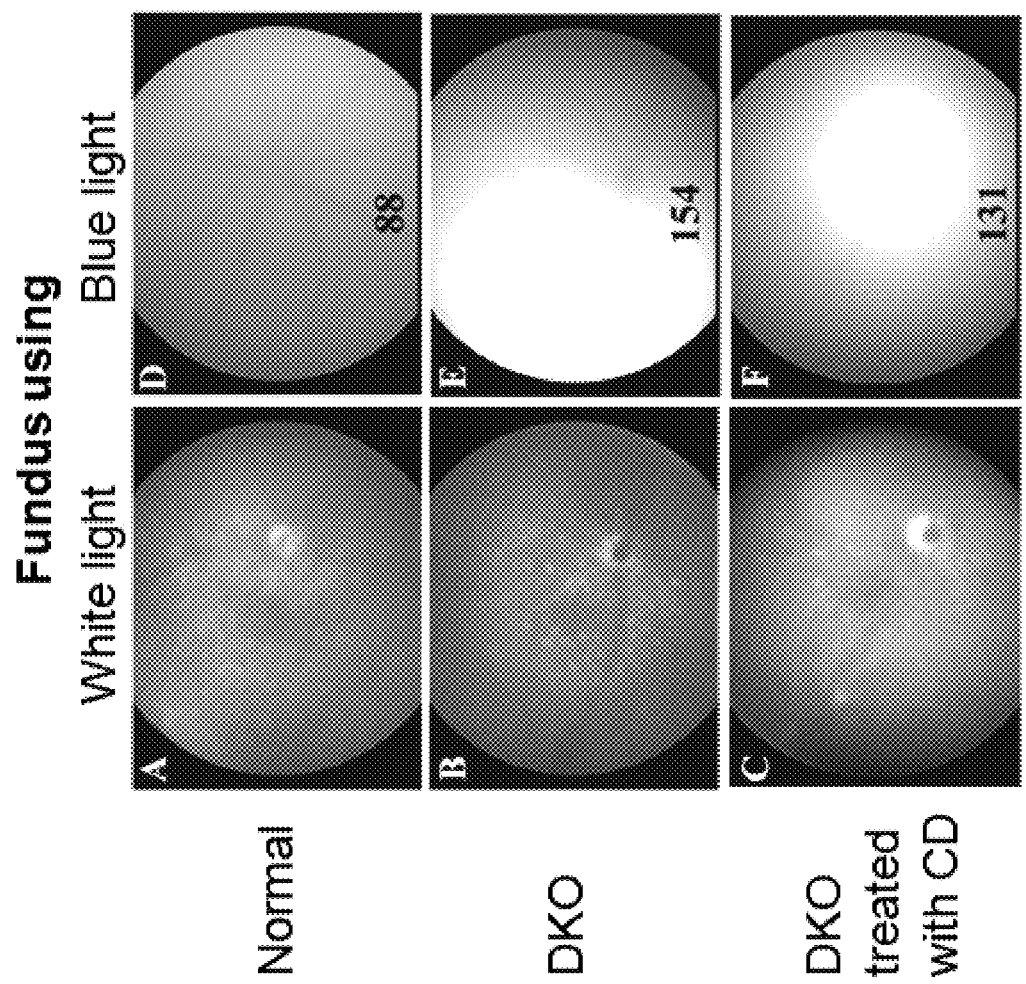

FIG. 16B shows fundus images obtained from eight month old WT control (A), DKO (B) and CD-treated DKO (C) mice. The clear dots (drusen) in color fundus of DKO are notably reduced by CD treatment (compare D, E, and F). The right panels display the autofluorescence fundus images from WT control (D), DKO (E), and CD-treated DKO (F) mice. The numbers indicate total amount of auto-fluorescence per mouse retina, which is a direct readout of the content of bisretinoids in RPE. Immunofluorescence examination of cryosected retinas show the effectiveness of the treatment with cyclodextrins. Briefly, subtenon treatment with methyl beta-cyclodextrin reduced the amount of autofluorescence in the RPE layer as well as the retinal detachment (compare untreated (b) with treated (c)). Thus, FIG. 16 shows that CD treatment of DKO mice reduces fundus, drusen, and autofluorescence.

Example 8

Measurement of the Strength of the Interaction Between CDs and A2E

The fluorescence of A2E changes upon inclusion in the CD cavity, and the magnitude of this shift is related to the degree of binding. Therefore, using this information the dissociation constant ($K_d$) can be determined for the complexes of A2E with the different cyclodextrins by using the Benesi-Hildebrand plot and calculations. Accordingly, the $K_d$ is the ratio of the intersect/slope of the double reciprocal plot, $1/(F-F_0)$ vs. $1/[CD]$ (see FIG. 6), where $F_0$ is the fluorescence intensity of A2E in water, and F is the fluorescence intensity of A2E in a particular CD solution. The $K_d$ data for the CD compounds in FIG. 7 are tabulated in FIG. 6.

Example 9

Microscopic Views of Retinas of DKO Mice with and without CD Treatment

Figure 18:
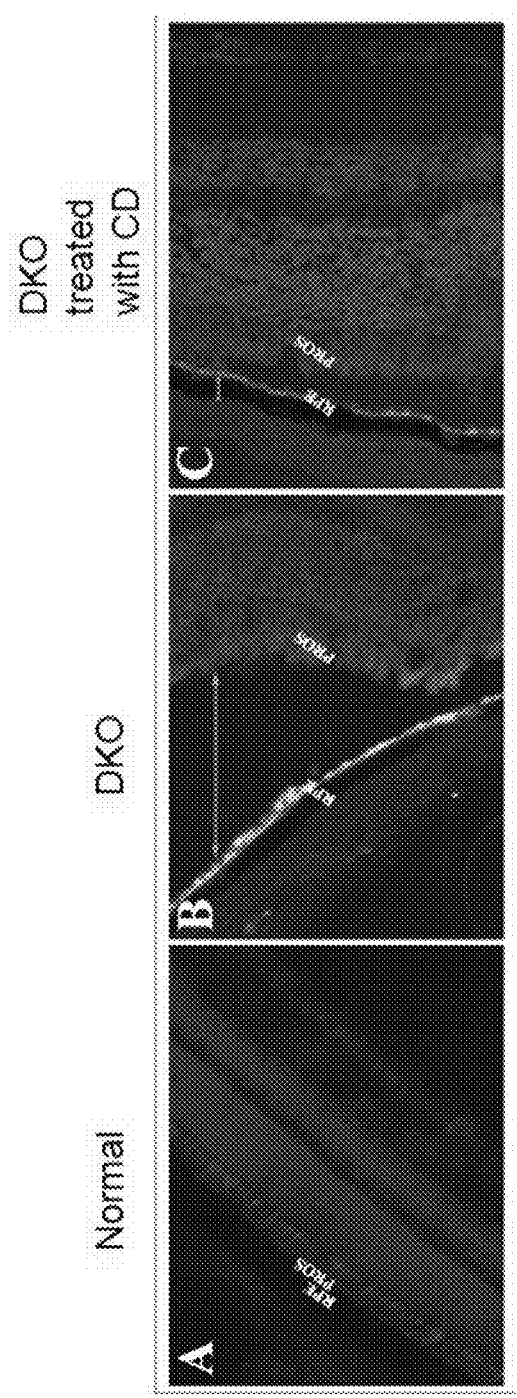
FIG. 18. Micrographs showing the fluorescence of cryosected retinas of 8-months old WT and DKO mice. The micrographs obtained from (A) a normal mouse, (B) DKO animals not treated with methyl beta-CD, and (C) DKO animals treated with methyl beta-CD. The DKO animals have strong autofluorescence in the RPE layer compared with WT as well as retinal detachment (size shown by arrow). Single subtenon administration of methyl Beta CD (4000 mg/kg) reduced both RPE autofluorescence and retinal detachment.

The retinas of wild type and DKO animals were analyzed by fluorescence microscopy with the following procedure. Briefly wild type and DKO animals were mock-treated or treated with a single subtenon injection with either vehicle or with methyl beta-cyclodextrin (4000 mg/kg). After 48 hours the eyes were enucleated, fixed, and cryosected. For viewing, 10-micron thick sections were blocked and stained with the red-fluorescently labeled lectin PNA to identify cones in the photoreceptor outer segments (PROS), and blue DAPI nuclear stain to identify the nuclei. In the gray scale micrograph of FIG. 18 (Panel A), the red and blue stains are not distinguishable, so the red fluorescence is labeled PROS and the lighter autofluorescent RPE is also labeled. (The blue nuclei are unlabeled, but are the dotted lighter region to the right of the PROS.) The retina from the mock treated DKO (panel B) mouse retina displays both retinal detachment, depicted by the arrow, and substantial RPE autofluoresence due to bisretinoids. Panel C shows the retina from the DKO mouse treated with methyl beta-cyclodextrin, which displays reduced detachment and bisretinoid autofluorescence.

While there have been shown and described what are at present considered the preferred embodiments of the invention, those skilled in the art may make various changes and modifications which remain within the scope of the invention defined by the appended claims.

What is claimed is:

1. A method for treating a subject suffering from a disorder characterized by the intracellular accumulation of lipofuscin bisretinoid lipids in retinal pigment epithelial (RPE) cells, the method comprising administering to said subject a therapeutically-effective amount of a (2-hydroxypropyl)-beta-cyclodextrin that targets retinal pigment epithelium cells and has an available binding cavity that is not complexed with a guest molecule when administered and that complexes lipofuscin bisretinoid lipids in said retinal pigment epithelium cells, wherein said disorder is selected from Stargardt disease, Best disease, retinitis pigmentosa, and cone-rod dystrophy.

2. The method of claim 1, wherein the method prevents lipofuscin-associated retinal damage from worsening in said subject suffering from lipofuscin-associated retinal damage.

3. The method of claim 1, wherein the method reverses symptoms of said disorder associated with lipofuscin-associated retinal damage.

4. The method of claim 1, wherein the method stops, mitigates, or reverses accumulation of lipofuscin in retinal pigment epithelium cells.

5. The method of claim 1, wherein said lipofuscin bisretinoid lipid is selected from N-retinylidene-N-retinylethanolamine (A2E), an A2E isomer, an oxidized derivative of A2E, and all-trans-retinal dimers.

6. The method of claim 1, wherein said (2-hydroxypropyl)-beta-cyclodextrin is coupled to an agent that targets retinal pigment epithelium cells.

7. The method of claim 6, wherein said agent targets endosomes or lysosomes in said retinal pigment epithelium cells.

8. The method of claim 6, wherein said agent is mannose 6-phosphate.

9. The method of claim 1, wherein the (2-hydroxypropyl)-beta-cyclodextrin is administered by topical, intravitreous, subretinal, or subscleral administration.

10. The method of claim 9, wherein said subscleral administration is achieved by implanting in said subject a slow-release subscleral implant.

11. The method of claim 1, wherein said disease or condition is Stargardt disease.

* * * * *